US012653882B2

(12) United States Patent
van der Ley et al.

(10) Patent No.: US 12,653,882 B2
(45) Date of Patent: Jun. 16, 2026

(54) CLICK OUTER MEMBRANE VESICLES

(71) Applicant: Intravacc B.V., Bilthoven (NL)

(72) Inventors: Peter André van der Ley, Utrecht (NL); Afshin Zariri, Velp (NL); Coen Peter Phielix, Soest (NL); Cornelia Pia Kruiswijk, Vinkeveen (NL)

(73) Assignee: Intravacc B.V., Bilthoven (NL)

( * ) Notice: Subject to any disclaimer, the term of this patent is extended or adjusted under 35 U.S.C. 154(b) by 735 days.

(21) Appl. No.: 17/923,257

(22) PCT Filed: May 7, 2021

(86) PCT No.: PCT/EP2021/062092
§ 371 (c)(1),
(2) Date: Nov. 4, 2022

(87) PCT Pub. No.: WO2021/224439
PCT Pub. Date: Nov. 11, 2021

(65) Prior Publication Data
US 2023/0270849 A1      Aug. 31, 2023

(30) Foreign Application Priority Data

May 8, 2020      (EP) .................................... 20173663

(51) Int. Cl.
| | |
|---|---|
| *A61K 39/39* | (2006.01) |
| *A61K 39/00* | (2006.01) |
| *A61K 39/215* | (2006.01) |
| *A61P 37/04* | (2006.01) |

(52) U.S. Cl.
CPC .......... *A61K 39/39* (2013.01); *A61K 39/0011* (2013.01); *A61K 39/215* (2013.01); *A61P 37/04* (2018.01); *A61K 2039/55516* (2013.01); *A61K 2039/55594* (2013.01)

(58) Field of Classification Search
None
See application file for complete search history.

(56) References Cited

U.S. PATENT DOCUMENTS

| | | | |
|---|---|---|---|
| 2003/0022829 A1* | 1/2003 | Maury | A61P 31/12 |
| | | | 530/324 |
| 2010/0260793 A1 | 10/2010 | Kwak et al. | |

FOREIGN PATENT DOCUMENTS

| | | |
|---|---|---|
| WO | 2016193370 A1 | 12/2016 |
| WO | 2018167061 A1 | 9/2018 |

OTHER PUBLICATIONS

Yifeng Li. Protein Expression and Purification 87 (2013) 72-7.*
Huan et al. Front. Microbiol., Oct. 16, 2020, vol. 11, article 582779, pp. 1-21.*
Durr et al. Biochimica et Biophysica Acta 1758 (2006) 1408-1425.*
Kosciuczuk et al. Molecular Biology Reports (2012) 39:10957-10970.*
An, L.L., Yang, Y.H., Ma, X.T., Lin, Y.M., Li, G., Song, Y.H. and Wu, K.F., 2005. LL-37 enhances adaptive antitumor immune response in a murine model when genetically fused with M-CSFRJ6-1 DNA vaccine. Leukemia research, 29(5), pp. 535-543.
Davidson, D.J. and Currie, A.J., 2005. Letting the CAThelicidin out of the bag, as a therapeutic modulator of the adaptive immune system. Leukemia Research, 29(5), pp. 477-479.
Van der Pol, L., Stork, M. and van der Ley, P., 2015. Outer membrane vesicles as platform vaccine technology. Biotechnology journal, 10(11), pp. 1689-1706.
Mishra, N.M., Briers, Y., Lamberigts, C., Steenackers, H., Robijns, S., Landuyt, B., Vanderleyden, J., Schoofs, L., Lavigne, R., Luyten, W. and Van der Eycken, E.V., 2015. Evaluation of the antibacterial and antibiofilm activities of novel CRAMP-vancomycin conjugates with diverse linkers. Organic & Biomolecular Chemistry, 13(27), pp. 7477-7486.

* cited by examiner

*Primary Examiner* — Oluwatosin A Ogunbiyi
(74) *Attorney, Agent, or Firm* — Ipsilon USA-NLO

(57) ABSTRACT
The specification pertains to a complex of an outer membrane vesicle (OMV), a vertebrate antimicrobial peptide (AMP) and an antigen, wherein the AMP is non-covalently complexed with the OMV and wherein the antigen is conjugated to the AMP. Preferably, the antigen is covalently linked to the AMP. The specification further concerns the induction of an immune response using the complex of the invention as well as a method for producing the complex of the invention.

19 Claims, 8 Drawing Sheets

Figure 1A:
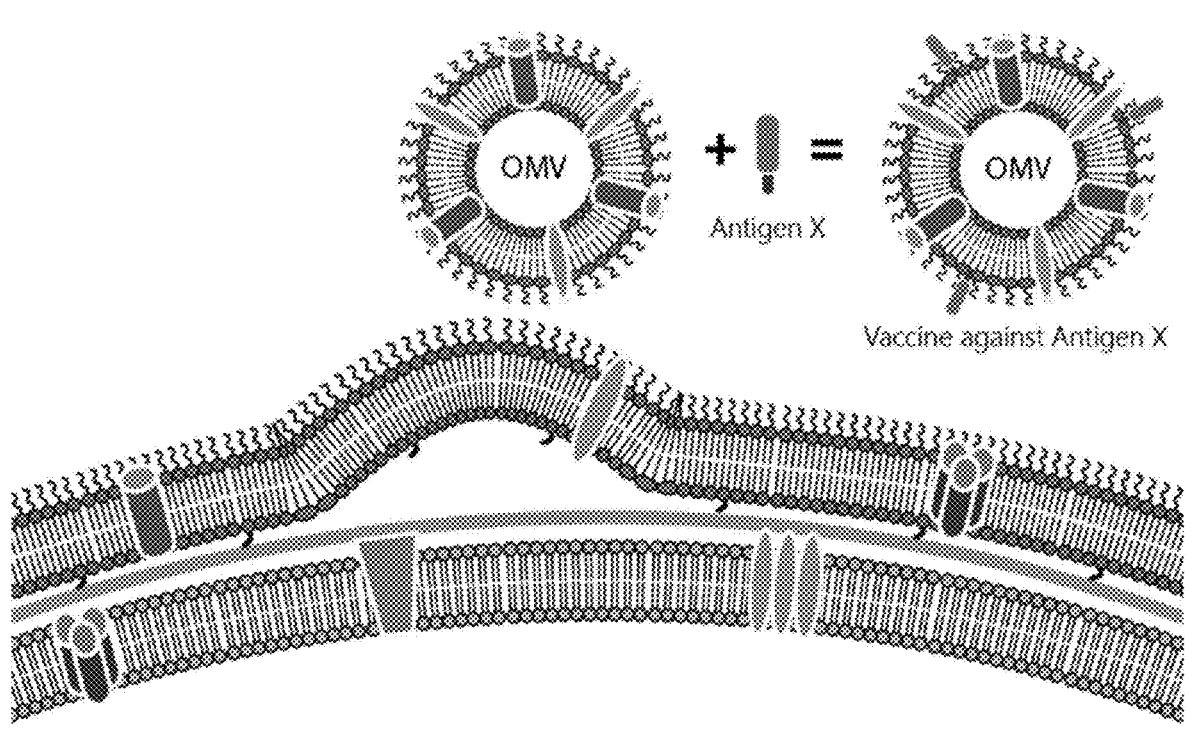

Specification includes a Sequence Listing.

CLICK OUTER MEMBRANE VESICLES

FIELD OF THE INVENTION

The present invention is in the field of vaccinology. The invention pertains to a platform technology, using modified outer membrane vesicles (OMV) for inducing or augmenting an immune response against an antigen, wherein the antigen is non-covalently attached to the OMV. The invention further pertains to a method for producing the OMVs of the invention.

BACKGROUND

Outer Membrane Vesicles (OMVs) are non-replicating structures released by Gram-negative bacteria that contain many crucial bacterial surface components, in combination with pathogen associated molecular patterns (PAMPs) that trigger innate immune responses and thereby work as internal adjuvants. Such PAMPs preferably activate at least one of TLR2 and TLR4. OMVs are spherical nanostructures (50-250 nm) mainly composed of lipids, LPS and outer membrane proteins, which efficiently present antigens to the immune system generating strong Ig and CD4+ T cell responses. OMVs from *Neisseria meningitidis* have a long history of use as experimental vaccines against meningococcal disease. The use of OMVs has been proven to be save and e.g. OMV containing MenB vaccines are currently on the market.

A next-generation OMV concept based on engineered hypervesiculating strains with genetically detoxified LPS has been developed, which obviates the need to use detergent extraction for LPS removal. These native (n)OMVs are straightforward to produce and retain many loosely attached surface antigens, making them more immunogenic. Heterologous non-meningococcal antigens can be made more immunogenic by capitalizing on the nOMV presentation form. To this end there have been methods developed in the art for heterologous surface display, based on endogenous expression of antigens, which are subsequently transported to the outer membrane of OMVs. This method was used to express heterologous OspA on meningococcal OMVs. When mice were immunized with this set of OMVs, OspA-specific antibody responses were elicited by OMVs with surface-exposed OspA (Salverda, Vaccine 34:1025-1033, 2016).

The OMV carrier is a proven and safe vaccine component. The OMV production process is scalable, gives high yields, uses chemically defined media, and is GMP compatible. A step of detergent extraction can be incorporated in the production process to remove LPS and increase vesicle release. A drawback of detergent-extraction is the removal of potential protective antigens from the outer membrane, such as the more loosely attached surface-exposed lipoproteins, and a reduction of the long-term stability of the OMV vaccine. Instead of detergent extraction, other techniques are known in the art to obtain OMVs, such as e.g. the use of chelating agents such as EDTA or genetic modifications that loosens the outer membrane, leading to increased OMV release.

In conjunction, to manipulate the immune response and optimize safety, the intrinsic adjuvant lipopolysaccharide (LPS) can be genetically detoxified. Such modifications can e.g. be the production of penta-acylated lipid A species that exhibit strong adjuvant activity, and reduced endotoxic activity (Zariri, Sci Rep 6:36575, 2016).

OMVs have excellent intrinsic immunostimulatory properties and can act as pathogen-mimetic adjuvants. Heterologous antigens can be made more immunogenic by capitalizing on the OMV presentation form. In particular, OMVs are highly efficient in stimulating their uptake and processing by antigen-presenting cells due to their size and their content of various PAMPs. However, it is important that the co-delivered antigens are taken up simultaneously, otherwise the antigen-presenting cells will become activated and migratory before efficient antigen uptake has taken place. For this reason coupling of the antigen to the OMVs is desired to generate an optimal immune response. This requires methods for heterologous surface display. However, the application of endogenous expression is limited by the need to obtain efficient expression and OMV incorporation of the antigen of choice, which can be difficult to obtain in many instances. The requirement for compatibility with the bacterial outer membrane (OM) biogenesis machinery limits the efficient expression of many heterologous antigens.

Therefore, there is still a strong need in the art for a versatile OMV platform for antigen display. There is in particular a need for an OMV platform that can be used for the display of a wide variety of known and/or new antigens, without requiring the need of expressing the antigen in the OMV producing cell.

SUMMARY

In an aspect, the invention pertains to a complex of an Outer Membrane Vesicle (OMV) a vertebrate antimicrobial peptide (AMP) and an antigen, wherein the AMP is non-covalently complexed with the OMV and wherein the antigen is conjugated to the AMP.

Preferably, the antigen is covalently linked to the AMP in a fusion protein comprising the antigen and the AMP in a single polypeptide chain.

Preferably, the AMP is a cathelicidin, preferably a non-human cathelicidin, more preferably mCRAMP.

Preferably, the antigen is an antigen that is associated with an infectious disease and/or a tumour.

Preferably, the OMV is not a detergent-extracted OMV, wherein preferably the OMV is a spontaneous OMV or a native OMV, preferably a native OMV.

Preferably, the OMV comprises at least partially detoxified LPS.

Preferably, the OMV is obtainable from a Gram-negative bacterium and wherein the Gram-negative bacterium preferably comprises at least one of:

a) a genetic modification causing the bacterium to produce an LPS with reduced toxicity, wherein preferably the genetic modification reduces or eliminates expression of at least one of a lpxL1, lpxL2, lpxA, lpxD and lpxK gene or a homologue thereof and/or increases the expression of at least one of an lpxP, lpxE, lpxF and pagL gene; and b) a genetic modification that increases vesicle formation, wherein preferably, the genetic modification reduces or eliminates expression of an ompA gene or a homologue thereof, more preferably a rmpM gene or a homologue thereof.

Preferably, the OMV is obtainable from a Gram-negative bacterium that belongs to a genus selected from the group consisting of *Neisseria, Bordetella, Escherichia* and *Salmonella*, preferably the bacterium belongs to a species selected from the group consisting of *Neisseria meningitidis, Bordetella pertussis, Escherichia coli* and *Salmonella enterica.*

The invention further concerns a pharmaceutical composition comprising a complex as defined herein and a pharmaceutically accepted excipient.

The invention also relates to a complex as defined herein or a pharmaceutical composition as defined herein for use as a medicament.

The invention further pertains to a complex as defined herein or a pharmaceutical composition as defined herein for use in a treatment comprising inducing or stimulating an immune response in a subject against the antigen.

The invention concerns an antigen conjugated to an AMP as defined herein, wherein preferably the antigen conjugated to the AMP is a fusion protein as defined herein.

The invention pertains to a nucleic acid encoding a fusion protein as defined herein.

The invention also concerns a host cell expressing a fusion protein as defined herein, wherein preferably the host cell comprises a nucleic acid as defined herein.

The invention relates to a method for producing a complex as defined herein, wherein the method comprises the steps of:

i) culturing a population of Gram-negative bacteria as defined herein under conditions conducive for the production of OMV;

ii) recovering the OMV produced in i);

iii) contacting the OMV recovered in ii) with the AMP conjugated to the antigen as defined herein, under conditions conducive to the formation of a non-covalent complex between the AMP and the OMV; and vi) optionally, recovery of the complex.

Definitions

Various terms relating to the methods, compositions, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

Methods of carrying out the conventional techniques used in methods of the invention will be evident to the skilled worker. The practice of conventional techniques in molecular biology, biochemistry, computational chemistry, cell culture, recombinant DNA, bioinformatics, genomics, sequencing and related fields are well-known to those of skill in the art and are discussed, for example, in the following literature references: Sambrook et al. Molecular Cloning. A Laboratory Manual, 2nd Edition, Cold Spring Harbor Laboratory Press, Cold Spring Harbor, N. Y., 1989; Ausubel et al. Current Protocols in Molecular Biology, John Wiley & Sons, New York, 1987 and periodic updates; and the series Methods in Enzymology, Academic Press, San Diego.

"A", "an," and "the": these singular form terms include plural referents unless the content clearly dictates otherwise. Thus, for example, reference to "a cell" includes a combination of two or more cells, and the like.

As used herein, the term "about" is used to describe and account for small variations. For example, the term can refer to less than or equal to ±10%, such as less than or equal to ±5%, less than or equal to ±4%, less than or equal to ±3%, less than or equal to ±2%, less than or equal to ±1%, less than or equal to ±0.5%, less than or equal to ±0.1%, or less than or equal to ±0.05%. Additionally, amounts, ratios, and other numerical values are sometimes presented herein in a range format. It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth.

"And/or": the term "and/or" refers to a situation wherein one or more of the stated cases may occur, alone or in combination with at least one of the stated cases, up to with all of the stated cases.

"Comprising": this term is construed as being inclusive and open ended, and not exclusive. Specifically, the term and variations thereof mean the specified features, steps or components are included. These terms are not to be interpreted to exclude the presence of other features, steps or components.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, CA 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blosum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at http://www.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, aspartate-glutamate and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; arg to lys; asn to gln or his; asp to glu; cys to ser or ala; gln to asn; glu to asp; gly to pro; his to asn or gln; ile to leu or val; leu to ile or val; lys to arg; gln or glu; met to leu or ile; phe to met, leu or tyr; ser to thr; thr to ser; trp to tyr; tyr to trp or phe; and, val to ile or leu.

As used herein, the term "selectively hybridizing", "hybridizes selectively" and similar terms are intended to describe conditions for hybridization and washing under which nucleotide sequences at least 66%, at least 70%, at least 75%, at least 80%, more preferably at least 85%, even more preferably at least 90%, preferably at least 95%, more preferably at least 98% or more preferably at least 99% homologous to each other typically remain hybridized to each other. That is to say, such hybridizing sequences may share at least 45%, at least 50%, at least 55%, at least 60%, at least 65, at least 70%, at least 75%, at least 80%, more preferably at least 85%, even more preferably at least 90%, more preferably at least 95%, more preferably at least 98% or more preferably at least 99% sequence identity.

A preferred, non-limiting example of such hybridization conditions is hybridization in 6× sodium chloride/sodium citrate (SSC) at about 45° C., followed by one or more washes in 1×SSC, 0.1% SDS at about 50° C., preferably at about 55° C., preferably at about 60° C. and even more preferably at about 65° C.

Highly stringent conditions include, for example, hybridization at about 68° C. in 5×SSC/5×Denhardt's solution/ 1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), Sambrook and Russell (2001) "Molecular Cloning: A Laboratory Manual (3rd edition), Cold Spring Harbor Laboratory, Cold Spring Harbor Laboratory Press, New York 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly(A) stretch or the complement thereof (e.g., practically any double-stranded cDNA clone).

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most cells, preferably bacterial cells, under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The term "peptide" as used herein is defined as a chain of amino acid residues, usually having a defined sequence, but without reference to a specific mode of action, size, 3-dimensional structure or origin. As used herein the term peptide is interchangeable with the terms "polypeptide" and "protein". In the context of the present invention, the term "peptide" is defined as being any peptide or protein comprising at least two amino acids linked by a modified or unmodified peptide bond. The term "peptide" refers to short-chain molecules such as oligopeptides or oligomers or to long-chain molecules such as proteins.

A protein/peptide can be linear, branched or cyclic. The peptide can include D amino acids, L amino acids, or a combination thereof. A peptide according to the present invention can comprise modified amino acids. Thus, the peptide of the present invention can also be modified by natural processes such as post-transcriptional modifications or by a chemical process. Some examples of these modifications are: acetylation, acylation, ADP-ribosylation, amidation, covalent bonding with flavine, covalent bonding with a heme, covalent bonding with a nucleotide or a nucleotide derivative, covalent bonding to a modified or unmodified carbohydrate moiety, bonding with a lipid or a lipid derivative, covalent bonding with a phosphotidylinositol, cross-linking, cyclization, disulfide bond formation, demethylation, cysteine molecule formation, pyroglutamate formation, formylation, gamma-carboxylation, hydroxylation, iodination, methylation, oxidation, phosphorylation, racemization, etc. Thus, any modification of the peptide which does not have the effect of eliminating the immunogenicity of the peptide, is covered within the scope of the present invention.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but e.g. have been obtained from another cell or synthetically or recombinantly produced. Generally, though not necessarily, such nucleic acids encode proteins, i.e. exogenous proteins, that are not normally produced by the cell in which the DNA is transcribed or expressed. Similarly exogenous RNA may encode for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The term "immune response" as used herein refers to the production of antibodies and/or cells (such as T lymphocytes) that are directed against, and/or assist in the decomposition and/or inhibition of, a particular antigenic entity, carrying and/or expressing or presenting antigens and/or antigenic epitopes at its surface. The phrases "an effective immunoprotective response", "immunoprotection", and like terms, for purposes of the present invention, mean an immune response that is directed against one or more antigenic epitopes of a pathogen, a pathogen-infected cell or a cancer cell so as to protect against infection by the pathogen or against cancer in a vaccinated subject. For purposes of the present invention, protection against infection by a pathogen or protection against cancer includes not only the absolute prevention of infection or cancer, but also any detectable reduction in the degree or rate of infection by a pathogen or of the cancer, or any detectable reduction in the severity of the disease or any symptom or condition resulting from infection by the pathogen or cancer in the vaccinated subject, for example as compared to an unvaccinated infected subject. An effective immunoprotective response in the case of cancer also includes clearing up the cancer cells, thereby reducing the size of cancer or even abolishing the cancer. Vaccination in order to achieve this is also called therapeutic vaccination. Alternatively, an effective immunoprotective response can be induced in subjects that have not previously been infected with the pathogen and/or are not infected with the pathogen or do not yet suffer from cancer at the time of vaccination, such vaccination can be referred to as prophylactic vaccination.

According to the present invention, the general use herein of the term "antigen" refers to any molecule that binds specifically to an antibody. The term also refers to any molecule or molecular fragment that can be bound by an MHC molecule and presented to a T-cell receptor. Antigens can be e.g. proteinaceous molecules, i.e. polyaminoacid sequences, optionally comprising non-protein groups such as carbohydrate moieties and/or lipid moieties or antigens can be e.g. molecules that are not proteinaceous such as carbohydrates. An antigen can be e.g. any portion of a protein (peptide, partial protein, full-length protein), wherein the protein is naturally occurring or synthetically derived, a cellular composition (whole cell, cell lysate or disrupted cells), an organism (whole organism, lysate or disrupted cells) or a carbohydrate or other molecule, or a portion thereof, that is able to elicit an antigen-specific immune response (humoral and/or cellular immune response) in a particular subject, which immune response preferably is measurable via an assay or method.

The term "antigen" is herein understood as a structural substance which serves as a target for the receptors of an adaptive immune response. An antigen thus serves as target for a TCR (T-cell receptor) or a BCR (B-cell receptor) or the secreted form of a BCR, i.e. an antibody. The antigen can thus be a protein, peptide, carbohydrate or other hapten that is usually part of a larger structure, such as e.g. a cell or a virion. The antigen may originate from within the body ("self") or from the external environment ("non-self"). The immune system is usually non-reactive against "self" antigens under normal conditions due to negative selection of T cells in the thymus and is supposed to identify and attack only "non-self" invaders from the outside world or modified/harmful substances present in the body under e.g. disease conditions. Antigen structures that are the target of a cellular immune response are presented by antigen presenting cells (APC) in the form of processed antigenic peptides to the T cells of the adaptive immune system via a histocompatibility molecule. Depending on the antigen presented and the type of the histocompatibility molecule, several types of T cells can become activated. For T-Cell Receptor (TCR) recognition, the antigen is processed into small peptide fragments inside the cell and presented to a T-cell receptor by major histocompatibility complex (MHC).

The term "immunogen" is used herein to describe an entity that comprises or encodes at least one epitope of an antigen such that when administered to a subject, preferably together with an appropriate adjuvant, elicits a specific humoral and/or cellular immune response in the subject against the epitope and antigen comprising the epitope. An immunogen can be identical to the antigen or at least comprises a part of the antigen, e.g. a part comprising an epitope of the antigen. Therefore, to vaccinate a subject against a particular antigen means, in one embodiment, that an immune response is elicited against the antigen or immunogenic portion thereof, as a result of administration of an immunogen comprising at least one epitope of the antigen. Vaccination preferably results in a protective or therapeutic effect, wherein subsequent exposure to the antigen (or a source of the antigen) elicits an immune response against the antigen (or source) that reduces or prevents a disease or condition in the subject. The concept of vaccination is well-known in the art. The immune response that is elicited by administration of a prophylactic or therapeutic composition of the present invention can be any detectable change in any facet of the immune status (e.g., cellular response, humoral response, cytokine production), as compared to in the absence of the administration of the vaccine.

An "epitope" is defined herein as a single immunogenic site within a given antigen that is sufficient to elicit an immune response in a subject. Those of skill in the art will recognize that T cell epitopes are different in size and composition from B cell epitopes, and that T cell epitopes presented through the Class I MHC pathway differ from epitopes presented through the Class II MHC pathway. Epitopes can be linear sequences or conformational epitopes (conserved binding regions) depending on the type of immune response. An antigen can be as small as a single epitope, or larger, and can include multiple epitopes. As such, the size of an antigen can be as small as about 5-12 amino acids (e.g., a peptide) and as large as a full length protein, including multimeric proteins, protein complexes, virions, particles, whole cells, whole microorganisms, or portions thereof (e.g., lysates of whole cells or extracts of microorganisms).

An adjuvant is herein understood to be an entity, that, when administered in combination with an antigen to a human or an animal subject to raise an immune response against the antigen in the subject, stimulates the immune system, thereby provoking, enhancing or facilitating the immune response against the antigen, preferably without necessarily generating a specific immune response to the adjuvant itself. A preferred adjuvant enhances the immune response against a given antigen by at least a factor of 1.5, 2, 2.5, 5, 10 or 20, as compared to the immune response generated against the antigen under the same conditions but in the absence of the adjuvant. Tests for determining the statistical average enhancement of the immune response against a given antigen as produced by an adjuvant in a group of animal or human subjects over a corresponding control group are available in the art. The adjuvant preferably is capable of enhancing the immune response against at least two different antigens.

OMV (also referred to as "blebs") are bi-layered membrane structures, usually spherical, with a diameter in the range of 20-250 nm (sometimes 10-500 nm), that are pinched off from the outer membrane of gram-negative bacteria. The OMV membrane contains phospholipids (PL) on the inside and lipopolysaccharides (LPS) and PL on the outside, mixed with membrane proteins in various positions, largely reflecting the structure of the bacterial outer membrane from which they pinched off. The lumen of the OMV may contain various compounds from the periplasm or cytoplasm, such as proteins, RNA/DNA, and peptidoglycan (PG), however, unlike bacterial cells, OMV lack the ability to self-replicate. In the context of the present invention three type of OMV can be distinguished depending on the method of their production. sOMV are spontaneous or natural OMV that are purified and concentrated from culture supernatant, by separating intact cells from the already formed OMVs. Detergent OMV, dOMV, are extracted from cells with detergent, such as deoxycholate, which also reduces the content of reactogenic LPS. After detergent extraction dOMV are separated from cells and cellular debris and further purified and concentrated. Finally, the term native nOMV is used herein for OMV that are generated from concentrated dead cells with non-detergent cell disruption techniques, or that are extracted from cells with other (non-disruptive) detergent-free methods (e.g. using chelating agents such EDTA), to be able to clearly distinguish them from the wild-type spontaneous OMVs and from the detergent-extracted dOMV.

Any reference to nucleotide or amino acid sequences accessible in public sequence databases herein refers to the version of the sequence entry as available on the filing date of this document.

DETAILED DESCRIPTION

The inventors developed a method to straightforwardly display known and newly identified antigens e.g. from emerging pathogens on the well-established and immunogenic OMV platform. OMVs can be stockpiled in advance, new target antigens e.g. identified through bioinformatics can be produced and attached using the method of the invention, thus providing for a rapid response platform.

Figure 1B:
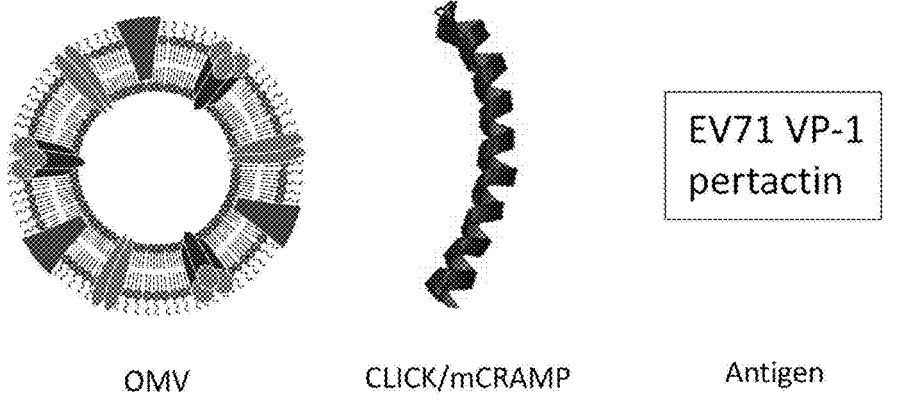

Using this technology, the OMV platform can e.g. be rapidly deployed in case of epidemics. A strength of the platform of the invention is the two component strategy, the OMV and the antigens. The antigens and OMV are produced separately and the antigens are non-covalently attached to the OMV upon simply mixing the antigens and the OMVs. To this end, the antigens contain an antimicrobial peptide (AMP) as a "tag" or "anchor" to facilitate attachment to the OMV. An exemplary embodiment of the invention is depicted in FIG. 1.

In a first aspect, the invention therefore pertains to a complex of an Outer Membrane Vesicle (OMV), an antimicrobial peptide (AMP) and an antigen. Preferably, the AMP is non-covalently complexed with the OMV and the antigen is conjugated to the AMP. In the complex of the invention, the AMP interacts with the membrane of OMV. Preferably, the AMP is inserted in the lipid layer of the OMV. The antigen that is conjugated to the AMP remains at least partly exposed to the surface of the OMV. It is understood herein that the AMP thus functions as an anchoring moiety, i.e. anchoring the antigen to the surface of the OMV.

Antimicrobial Peptide (AMP)

Preferably, the AMP is a vertebrate AMP. AMPs are part of the innate immune system of vertebrates, and are known to have a broad spectrum of antimicrobial activity against bacteria, enveloped viruses and fungi (Kosciuczuk et al, Mol Biol Rep (2012) 39:10957-10970). An AMP is capable of permeating or "puncturing" the negatively charged membrane of a pathogen. To this end, the AMP for use in the invention preferably has several positively charged residues, e.g. provided by arginine, lysine or, in acidic environments, histidine, and preferably comprises a large proportion (e.g. >50%) of hydrophobic residues.

The AMP may be unstructured in free solution, and fold into the final configuration upon partitioning into the membrane of the OMV. It may contain hydrophilic amino acid residues aligned along one side and hydrophobic amino acid residues aligned along the opposite side of e.g. a helical molecule. The amphipathicity of the antimicrobial peptides allows them to partition into the membrane lipid bilayer. The AMP for use in the invention is preferably a cationic peptide with amphipathic properties and is capable of penetrating the membrane of an OMV. Preferably, the AMP remains within the OMV membrane, i.e. does not partly or fully cross the OMV membrane. The AMP preferably does not, or does not significantly, disrupt the formed OMVs.

Preferably, the AMP for use in the invention is a mammalian AMP. Preferably, the AMP is the active form of at least one of a cathelicidin, an alpha-defensin, a beta-defensin and a regIII peptide. Preferably, the AMP is the active form of a cathelicidin. It is understood herein that protein names, such as the terms "cathelicidin", "alpha-defensin", "beta-defensin" and "regIII peptide" are not limited to human peptides, but also includes orthologues peptides in other vertebrates, preferably in other mammals. As a non-limiting example, the term "cathelicidin" includes the human cathelicidin LL-37 as well as orthologous "cathelicidin-related" peptide mCRAMP in mice.

The AMP may be produced in an inactive form, which becomes activated upon cleavage. For example, mammalian cathelicidins are composed of three domains, a signal peptide, a cathelin domain, and an antimicrobial domain. The signal peptide is required for intracellular targeting into granules and is cleaved off by a signal peptidase. The conserved cathelin domain, of which the function is poorly understood, remains attached to the antimicrobial domain during granule storage. Cleavage between the cathelin and antimicrobial domains releases the biologically active antimicrobial peptide. It is understood herein that the term AMP refers to the active form, i.e. the biologically active antimicrobial peptide.

The AMP for use in the invention can be a naturally occurring peptide, a recombinant peptide or a chemically synthesized peptide. The recombinant, or synthetic, AMP may be identical to a naturally occurring AMP. Alternatively, a recombinant (or synthetic) AMP for use in the invention can comprise one or more amino acid alterations as compared to the amino acid sequence of its naturally occurring counterpart. The amino acid alteration is preferably at least one of a deletion, addition or substitution of one or more amino acid residues An AMP of the invention may comprise one or more amino acid residue deletions as compared to its naturally occurring counterpart, preferably as compared to a naturally occurring cathelicidin. The AMP may comprise a deletion of at least 1, 2, 3, 4, 5 or 10 amino acid residues. Preferably, the AMP comprising one or more amino acid deletions maintains the ability to non-covalently bind to (or complex with) the OMV. Preferably, said ability to non-covalently bind to the OMV is equal to, or preferably higher than, the ability of its naturally occurring counterpart to bind to the OMV.

Alternatively or in addition, the AMP may comprise one or more amino acid residue additions as compared to its naturally occurring counterpart, preferably as compared to a naturally occurring cathelicidin. The AMP may comprise an addition of at least 1, 2, 3, 4, 5 or 10 amino acid residues. Preferably, the AMP comprising one or more amino acid additions maintains the ability to non-covalently bind to (or complex with) the OMV. Preferably, said ability to non-covalently bind to the OMV is equal to, or preferably higher than, the ability of its naturally occurring counterpart to bind to the OMV.

Alternatively or in addition, the AMP may comprise one or more amino acid residue substitutions as compared to its naturally occurring counterpart, preferably as compared to a naturally occurring cathelicidin. The AMP may comprise a substitutions of at least 1, 2, 3, 4, 5, 10, or 20 amino acid residues. Preferably, the AMP comprises one or more conservative amino acid substitutions, preferably one or more conservative amino acid substitutions as defined herein. Preferably, the recombinant AMP comprises at least 1, 2, 3, 4, 5, 10, 15 or 20 conservative amino acid substitutions. Preferably, the AMP comprising one or more amino acid substitutions maintains the ability to non-covalently bind to (or complex with) the OMV. Preferably, said ability to non-covalently bind to the OMV is equal to, or preferably higher than, the ability of its naturally occurring counterpart to bind to the OMV.

The ability of an AMP to bind to (or complex with) an OMV can be determined using any conventional method known in the art. Exemplary methods are provided in the example section below, such as but not limited to, an quantitative dot blot as detailed in example 1. The ability of an AMP to bind to an OMV can e.g. be determined by coupling a PRN peptide, or any other detectable moiety, to the AMP and subsequently combine the AMP with an OMV, e.g. on a dot blot. The PRN peptide, or any other detectable moiety, can subsequently be detected in a quantitative manner, e.g. using a quantitative anti-PRN antibody detection method.

The size of the AMP for use in the invention is preferably about 10-100 amino acid residues, about 12-80 amino acid residues, about 12-50 amino acids, about 12-18 amino acid residues, about 39-80 amino acid residues, about 20-40 amino acid residues or about 23-35 amino acid residues.

AMPs are known in the art to have a poorly conserved amino acid sequence identity. Instead, AMPs mainly are grouped on basis of amino acid properties and/or structures formed upon penetrating the bacterial membrane. In addition, AMPs are known in the art to comprise a wide range of structures. Hence, the skilled person understands that the invention is not limited to any specific AMP sequence or structure. Preferably, the AMP for use in the invention has a net charge from 0 to +7 and hydrophobic percentage between 30-70%.

The AMP may be a linear peptide that folds into an amphipathic α-helix or a small molecule with beta-hairpin structure, and may be stabilized by one, two or more disulphide bonds. Alternatively or in addition, the AMP may comprise repetitive proline motifs forming extended polyproline-type structures. A preferred AMP for use in the invention comprises an amphipathic, helical structure. Preferably, the AMP for use in the invention comprises an amphipathic cationic α-helical peptide.

Preferably, the AMP for use in the invention can be, or can be derived from, a naturally occurring protein, wherein the inactive form of the protein comprises a cathelin domain. Preferably, the cathelin domain is cleaved off, leading to AMP activation.

The AMP for use in the invention can be a cathelicidin, preferably a human cathelicidin or an orthologue thereof. The human cathelicidin LL-37 is a peptide with a wide range of antimicrobial activities, including both direct toxic effects on many different types of microorganisms and local immunomodulatory effects (Xhindoli et al BBA 1858 (2016) 546-566). It carries out its many different activities with a small amphipathic helical structure. It is made as a precursor prepro form by epithelial and immune cells. Its antibacterial effects result from direct interaction with membranes, including the outer membrane of gram-negative bacteria. The first step in this interaction is binding to the lipid A/inner core region of LPS, a major outer membrane lipid A. Since e.g. native OMVs retain their LPS, the inventors discovered that LL-37 can form a suitable tag which can be attached to diverse antigens and thereby direct them to associate with OMVs.

Since LL-37 is a human antigen, the combination with immunostimulatory OMVs could lead to an anti-self immune response. Therefore preferably the AMP is a non-human cathelicidin. The non-human cathelicidin may be derived from a human cathelicidin, e.g. can be a human cathelicidin comprising one or more amino acid alterations. The non-human cathelicidin thus may include a modified version of a human cathelicidin. The non-human cathelicidin is preferably a cathelicidin is derived from a mice, cattle, buffalo, horse, pig, sheep, goat, deer, chicken, fish, rhesus monkey, rats, guinea pigs or a snake. Preferably, the cathelicidin is a mouse or a rat cathelicidin, preferably a mouse cathelicidin. Optionally, the mouse cathelicidin comprises one or more amino acid alterations.

The cathelicidin for use in the invention may be a protein as specified in Table 1 of Kosciuczuk et al (supra), which is incorporated herein by reference, or a cathelicidin as specified in Table 1 of Kosciuczuk et al, supra, and having one or more amino acid alterations.

The AMP for use in the invention may be a protein selected from the group consisting of mCRAMP (CRAMP-1/2), LL-37, FALL-39, RL-37, rCRAMP, CAP-18, CAP-11, PR-39, Prophenin, PMAP-23, PMAP-36, PMAP-37, BMAP-27, BMAP-28, BMAP-34, Bac5, Bac7, cathelicidin-AL, fowlicidin 1, fowlicidin 2, fowlicidin 3, cathelicidin Beta-1, Saha-CATH5, CATH1 and CATH2. Preferably, the AMP is mCRAMP, optionally comprising one or more amino acid alterations.

The sequence of naturally occurring AMPs is highly diverse. Hence, the invention is not limited to any AMP having a specific sequence. The AMP for use in the invention can be cathelicidin having a sequence as disclosed in FIG. 1 of Kosciuczuk et al, supra, preferably a mature peptide sequence as disclosed in FIG. 1 of Kosciuczuk et al, supra. In an embodiment, the sequence of the AMP may have at least about 35%, 40%, 45%, 50%, 55%, 60%, 65%, 70%, 75%, 80%, 85%, 90%, 95%, 96%, 97%, 98%, 99%, or about 100% sequence identity to SEQ ID NO: 1 (mCRAMP). mCRAMP preferably has the sequence of:

```
                                       (SEQ ID NO: 1)
        GLLRKGGEKIGEKLKKIGQKIKNFFQKLVPQPEQ
```

In an embodiment, the sequence of the AMP may have at least about 35%, 40%, 45%, 50%, 55%, 60%, 65%, 70%, 75%, 80%, 85%, 90%, 95%, 96%, 97%, 98%, 99%, or about 100% sequence identity to SEQ ID NO: 13 (LL-37). LL-37 preferably has the sequence of:

```
                                      (SEQ ID NO: 13)
        LLGDFFRKSKEKIGKEFKRIVQRIKDFLRNLVPRTES
```

The AMP is preferably capable of penetrating the membrane of an OMV and non-covalently attaching an antigen, that is conjugated to the AMP, to the OMV.

AMP—Antigen Conjugation

In a preferred embodiment, the AMP is conjugated to an antigen, preferably an antigen as described herein. Conjugation of the antigen to AMP results in a conjugate that allows coupling or "anchoring" the antigen to the OMV when the AMP penetrates the membrane of the OMV.

The antigen can be conjugated to the AMP using any conventional means known in the art. Conjugation includes covalent binding and non-covalent binding. Preferably, the antigen is covalently bound to the AMP.

The antigen can be conjugated to the part of the AMP that remains exposed at the surface of the OMV once the AMP is inserted into the OMV membrane. Preferably, the antigen is conjugated to the AMP in a manner that does not interfere with the ability of the AMP to bind to the OMV. Preferably therefore, the antigen is conjugated to a hydrophilic residue in the AMP, more preferably to a hydrophilic residue that is solvent exposed when the AMP has penetrated a membrane (e.g. of an OMV). The antigen can be conjugated to or in close vicinity of one or more cationic amino acid residues of the AMP. Alternatively or in addition, the antigen is conjugated to the C-terminus or N-terminus of the AMP. Preferably, the antigen is conjugated to the N-terminus of the AMP peptide. In one embodiment more than one antigen molecule is conjugated to a combination of the aforementioned sites on the AMP. These more than one antigen molecule can be the same or different antigen molecules.

The antigen can be conjugated to the AMP using any conventional chemical conjugation process, whereby the, preferably covalent, binding does not (significantly) reduce the ability of the AMP to penetrate the OMV and anchoring the antigen to the OMV. To this end, the AMP and the antigen are first produced separately, followed by, preferably covalent, coupling of the AMP to the antigen. Such covalent coupling can be performed use any conventional means known to the person skilled in the art. This method may be preferred in case the AMP and antigen cannot be expressed as a single polypeptide, e.g. in case the antigen is an oligo- or poly-saccharide and/or in case the antigen requires a chemical modification, such as, but not limited to, circular-ization.

Preferred chemical conjugation methods are amide bond formation (for instance using active esters and free amines), selective N-terminal ligation, native chemical ligation, and biorthogonal ligation. Examples of biorthogonal ligation methods are Michael addition (for instance using a male-imide and a thiol, where the thiol can optionally be intro-duced via Traut's reagent), Diels-Alder cycloaddition, Huis-gen cycloaddition, cycloaddition using tetrazines or azides or transcyclooctenes or strained cyclooctynes or oxonorbor-nadienes. Such methods are widely known (see for instance Bioconjugate Chem. 2015, 26, 2, 176-192; and doi.org/10.1016/j.cbpa.2013.07.031 and doi.org/10.1016/j.chem-biol.2014.09.002) and required reagents are often commer-cially available even in kit form, including instructions for use.

The antigen can be conjugated directly to the AMP, or may be separated by a linker, preferably a linker as defined herein below. When not expressed as a single fusion protein, a linker can be a dedicated sequence of amino acids, a single amino acid, or another moiety such as ahx. The three letter code ahx represents 6-aminohexanoic acid, which is also known as aminocaproic acid, which in turn is abbreviated as Acp. Ahx is considered to be a linker moiety that links two further moieties together. In addition to ahx, other linkers can be used, such as, but not limited to, beta-alanine (also known as beta-aminopropionic acid, bAla), 4-Aminobutyric acid (also known as piperidinic acid, 4Abu), 3-Aminoisobu-tyric acid (bAib), or other linking moieties known in the art. Further examples of linkers are based on ethylene glycol, such as poly(ethylene glycol) (PEG) or oligo(ethylene gly-col). PEG-based linkers are desirable for their good solu-bility in water or other relevant solvents, and their ease of handling. PEG linkers are often used to improve renal clearance of peptides (Lang et al., Bioconjug. Chem. 2011 22(12): 2415-2422. doi: 10.1021/bc200197h) A linker is often defined by its function, which is to connect two further moieties to one another, ensuring their spatial proximity or limiting their respective spatial position. Linkers provide a mechanical bond. A skilled person will be able to select a suitable linker. For example, for N-terminal conjugation to a peptide, an alkyl chain or PEG with a free carboxylic acid moiety is suitable. In such a case, the other terminus of the PEG can for example be a protected amine, or another orthogonally reactive moiety. Non-limiting examples of suitable PEG termini are an amine, a carboxylic acid, a thiol, an alcohol, an aldehyde, an azide, an alkyn, or a protected version of any of these moieties.

Alternatively, the AMP and antigen may be produced as a single polypeptide or "fusion protein", wherein optionally there is a linker present between the AMP and the antigen. Hence preferably, the antigen is covalently linked to the AMP in a fusion protein comprising the antigen and the AMP in a single polypeptide chain. Preferably, N-terminal fusion partner of the fusion protein is the antigen and the C-terminal fusion partner of the fusion protein is the AMP. Preferably, the fusion protein comprises no amino acid residues outside of the AMP and the antigen and an optional the linker as defined later herein.

The invention thus also concerns an OMV comprising a fusion protein, wherein the first, preferably N-terminal, fusion partner is an antigen and the second, preferably C-terminal, fusion partner is an AMP capable of anchoring the antigen to the OMV. Preferably, the OMV and the fusion protein are produced separately, optionally in different (mi-cro-)organisms. The first and second fusion partner may be separated by a linker.

The antigen may be bound to the AMP by means of a linker (or spacer), preferably a flexible linker. Any conven-tional linker known in the art may be used to couple the AMP to the antigen. Preferably, the linker does not, or does not substantially interfere with the ability of the AMP to penetrate the OMV membrane. In addition or alternatively, the linker does not, or does not substantially, interfere with the ability of the antigen to elicit an immune response.

The linker can be a rigid linker or a flexible linker. The linker is preferably a flexible linker. The linker can first be conjugated, preferably covalently bound, to the AMP fol-lowed by conjugating, preferably covalently binding, the antigen to the linker. Alternatively, the linker can first be conjugated, preferably covalently bound, to the antigen followed by conjugating, preferably covalently binding, the AMP to the linker. Alternatively, part of the linker can be conjugated, preferably covalently bound, to the AMP and another part of the linker can be conjugated, preferably covalently bound, to the antigen, followed by conjugating, preferably covalently binding, of both parts of the linker together. Alternatively, the linker can be produced as part of the fusion protein.

Preferably, the linker is a peptide linker. The linker can be a glycine-rich flexible linker. Preferably, the length of the linker is between 2-50, 3-40, 4-30 or 5-20 amino acid residues. The linker can be a linker as specified in table 1 of Chichili et al (Protein Sci. 2013 February; 22(2): 153-167), which is incorporated herein by reference.

The linker can have a Gly-Ser sequence. The skilled person knows how to select the linker, dependent on the AMP and antigen. The linker may be e.g. a very flexible linker in the form GGGSGGGSGGGS (SEQ ID NO: 12), (GGGGS)n (SEQ ID NO: 10), (GGS)n, (GS)n and (G)n to more rigid linkers of the form (EAAAK)n (SEQ ID NO: 11), (SPKKKRKVEAS)n (SEQ ID NO: 2), or (SGSETPGTS-ESATPES)n (SEQ ID NO: 3), or (KSGSETPGTSESAT-PES)n (SEQ ID NO: 4), or any variant thereof, wherein n preferably is between 1 and 10, i.e. 1, 2, 3, 4, 5, 6, 7, 8, 9 or 10.

Optionally there are additional amino acid residues located between the antigen and the AMP, such as, but not limited to one or more tags and/or protease cleavage sites.

Optionally, a his tag and/or a Twin strep tag is present in between the antigen and the AMP. Alternatively or in addition, there is a protease cleave site, such as a HRV 3C recognition site, located in between the antigen and the AMP.

In another embodiment, there are no tags and/or protease cleavage site(s) located in between the antigen and the AMP.

Antigen

The invention is not limited to any specific antigen. The antigen for use in the invention is preferably suitable for conjugation to an AMP and subsequent display on the surface of the OMV. The antigen could be at least one of a saccharide or a peptide. The saccharide can be e.g. an oligosaccharide or a polysaccharide. Similarly, the peptide can be e.g. an oligopeptide or a long-chain molecule, such as a protein. Preferably, the antigen is a peptide.

The antigenic peptide can be a naturally occurring protein or a fragment thereof, preferably an antigenic fragment thereof. The antigenic peptide may comprise one or more modifications. As a non-limiting example, the antigenic peptide may comprise an N-terminal or C-terminal cysteine.

The antigen may comprise one or more epitopes retrieved from the epitope database iedb.org (Vita et al, Nucleic Acids Res. 2015; 43 (Database issue): D405-D412 and periodic updates) or any other, e.g. newly discovered, antigen. Preferably, the antigen comprises one or more epitopes from antigens associated with an infectious disease or a tumor. For example, the antigen fused to the AMP may comprise one or more epitopes derived from antigens from pathogens and infectious agents such as viruses, bacteria, fungi and protozoa.

Some examples of pathogenic viruses causing infections or tumours from which epitopes from antigens may be derived include: hepatitis (A, B, or C), herpes virus (e.g., VZV, HSV-I, HAV-6, HSV-II, and CMV, Epstein Barr virus), adenovirus, SV40 virus (causing mesothelioma), influenza virus, flaviviruses, ebola virus, echovirus, rhinovirus, coxsackie virus, coronavirus, respiratory syncytial virus (RSV), mumps virus, rotavirus, measles virus, rubella virus, parvovirus, vaccinia virus, HTLV virus, dengue virus, molluscum virus, poliovirus, rabies virus, JC virus, arboviral encephalitis virus, and human immunodeficiency virus (HIV virus; e.g., type I and II), human papilloma virus (HPV). Preferably, the antigen for use in the invention comprises one or more epitopes from a coronavirus or an enterovirus. Preferably, the antigen for use in the invention comprises one or more epitopes of a coranovirus. The coronavirus can be of the genus alpha coronavirus or beta coronavirus, preferably of the genus beta coronavirus. The subgenenus is preferably sarbecovirus or merbecovirus. Preferably, the antigen for use in the invention comprises one or more epitopes from a coronavirus selected from the group consisting of COVID-19 (SARS-CoV-2), SARS-CoV, MERS-CoV, HCoV-OC43 and HCoV-HKU1, HCoV-229E and HCoV-NL63. The antigen for use in the invention may comprise one or more epitopes from an enterovirus. The enterovirus is preferably at least one of a poliovirus, a coxsackievirus, an echovirus and a rhinovirus. Preferably, the enterovirus is a enterovirus 71 (EV71), preferably the epitope is from an enterovirus VP1 or VP2.

Some examples of pathogenic bacteria causing infections from which epitopes from antigens may be derived include: *Bordetella, Neisseria, Acinetobacter, Borrelia, Listeria, Escherichia, Chlamydia, Coxiella,* Rickettsial bacteria, Mycobacteria, Staphylococci, Streptococci, Pneumonococci, Meningococci, Gonococci, *Klebsiella, Proteus, Serratia, Pseudomonas, Legionella, Diphtheria, Salmonella,*

Bacilli, bacteria causing Cholera, Tetanus, Botulism, Anthrax, Plague, Leptospirosis, Whooping cough and Lymes disease. A preferred *Bordetella* antigen can be a Pertactin protein, or an antigenic fragment thereof, wherein the Pertactin protein preferably has at least about 35%, 40%, 45%, 50%, 55%, 60%, 65%, 70%, 75%, 80%, 85%, 90%, 95%, 96%, 97%, 98%, 99%, or about 100% sequence identity to SEQ ID NO: 18.

Some examples of pathogenic fungi causing infections from which epitopes from antigens may be derived include: *Candida* (e.g., *albicans, krusei, glabrata, tropicalis*), *Cryptococcus neoformans, Aspergillus* (e.g., *fumigatus, niger*), fungi of the genus *Mucorales* (*Mucor, Absidia, Rhizopus*), *Sporothrix schenkii, Blastomyces dermatitidis, Paracoccidioides brasiliensis, Coccidioides immitis* and *Histoplasma capsulatum.*

Some examples of pathogenic parasites causing infections from which epitopes from antigens may be derived include: *Entamoeba histolytica, Balantidium coli, Naegleria, Fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii* and *Plasmodium falciparis.*

In addition or alternatively, the antigen for use in the invention can comprise one or more epitopes from a wide range of tumour antigens, including e.g. MAGE, BAGE, RAGE, GAGE, SSX-2, NY-ESO-1, CT-antigen, CEA, PSA, p53, XAGE and PRAME but also virally induced malignancies, comprising Human papilloma virus (HPV), Kaposi sarcoma herpes virus (KSHV), Epstein Bar virus induced lymphoma's (EBV). Other examples of tumour antigens from which epitopes for use in the present invention may be derived are various ubiquitously expressed self-antigens that are known to be associated with cancer, which include e.g. p53, MDM-2, HDM2 and other proteins playing a role in p53 pathway, molecules such as surviving, telomerase, cytochrome P450 isoform 1B1, Her-2/neu, and CD19 and all so-called house hold proteins. Cancers that may be treated or prevented in accordance with the present invention are selected among the following list: lung, colon, esophagus, ovary, pancreas, skin, gastric, head and neck, bladder, sarcoma, prostate, hepatocellular, brain, adrenal, breast, endometrial, mesothelioma, renal, thyroid, hematological, carcinoid, melanoma, parathyroid, cervix, neuroblastoma, Wilms, testes, pituitary and pheochromocytoma cancers.

The antigen conjugated to the AMP may comprise or consists of one or more surface exposed epitopes from a proteinaceous antigen of an infectious agent or tumour. The antigen conjugated to the AMP can e.g. comprises or consists of an extracellular and/or surface exposed domain of the proteinaceous antigen of an infectious agent or tumour.

Preferably, the antigen coupled to the AMP comprises or consists of one or more epitopes from a surface exposed domain of a surface exposed viral protein or lipoprotein. Preferably, the one or more epitopes are from the surface exposed domain of a surface exposed viral protein or lipoprotein from a coronavirus or an enterovirus, preferably from COVID-19 or EV71, such as but not limited to a surface glycoprotein or "spike" of COVID-19 or the EV71 viral protein VP1 or VP2.

The antigen may comprise one or more epitopes from a viral spike protein. The antigen may be a viral spike protein, or an antigenic fragment thereof. A preferred spike protein, or an antigenic fragment thereof, is obtained from a coronavirus, preferably a coronavirus selected from the group consisting of COVID-19 (SARS-CoV-2), SARS-CoV, MERS-CoV, HCoV-0043 and HCoV-HKU1, HCoV-229E and HCoV-NL63. A preferred spike protein, or an antigenic fragment thereof, is obtained or derived from COVID-19.

The spike protein, preferably the SARS-CoV-2 spike protein, that may be used as an antigen in the complex of the invention may be in a prefusion or postfusion conformation. Preferably, the spike protein is in the prefusion conformation. The spike protein used as the antigen in the complex of the invention may be a native protein or a modified protein, e.g. modified to increase its stability. The spike protein used as an antigen in the complex of the invention may be a native of modified spike protein obtained or derived from any of the SARS-CoV-2 strains, preferably the spike protein is a native of modified spike protein obtained or derived from the SARS-CoV-2 strain Wuhan-Hu-1, GenBank MN908947.

Preferably, the spike protein is a modified protein having one or more amino acid substitutions. Preferably, the spike protein is a modified protein having one or more proline substitutions. Preferably, the spike protein is a modified protein in prefusion conformation and comprises 2, 3, 4, 5 or 6 proline substitutions. Preferably, the antigen in the complex of the invention comprises one or more epitopes from the spike protein as disclosed in Hsieh et al (Science. 2020 Sep. 18; 369(6510):1501-1505). Preferably, the antigen in the complex of the invention comprises or consists of the spike protein as disclosed in Hsieh et al (supra).

Preferably, the antigen in the complex of the invention is a SARS-CoV-2 spike protein having at least about 50%, 55%, 60%, 65%, 70%, 75%, 80%, 85%, 90%, 95%, 96%, 97%, 98%, 99% or 100% sequence identity with SEQ ID NO: 41. Preferably, the SARS-CoV-2 spike protein is encoded by a sequence having at least at least about 50%, 55%, 60%, 65%, 70%, 75%, 80%, 85%, 90%, 95%, 96%, 97%, 98%, 99% or 100% sequence identity with SEQ ID NO: 46. The spike protein may comprise one or more substitutions. Preferably, the spike protein may comprise a substitutions at a position selected from the group consisting of F816, A891, A898 and A941. Preferably, the spike protein comprises a substitution selected from the group consisting of F816P, A891P, A898P and A941P. Preferably, the spike protein comprises the substitutions F816P, A891P, A898P and A941P.

Preferably, the antigen in the complex of the invention is a SARS-CoV-2 spike protein having at least about 50%, 55%, 60%, 65%, 70%, 75%, 80%, 85%, 90%, 95%, 96%, 97%, 98%, 99% or 100% sequence identity with SEQ ID NO: 44. Preferably, the antigen in the complex of the invention is a SARS-CoV-2 spike protein encoded by a nucleotide sequence having at least about 50%, 55%, 60%, 65%, 70%, 75%, 80%, 85%, 90%, 95%, 96%, 97%, 98%, 99% or 100% sequence identity with SEQ ID NO: 49.

The spike protein is preferably conjugated to an AMP as defined herein, wherein preferably the AMP is a cathelicidin as defined herein. The spike protein is preferably conjugated to an mCRAMP as defined herein. Preferably the spike protein is conjugated to mCRAMP using a linker, preferably the linker GGGSGGGSGGGS (SEQ ID NO: 12).

In addition or alternatively, the amino acid sequence of the spike protein may be preceded or followed by a tag sequence and/or a protease cleavage site. The spike protein may be conjugated to at least one of a HRV 3C protease recognition site, a His tag and a Twin strep tag. The spike protein conjugated to one or more tags and a protease recognition site may have at least about 50%, 55%, 60%, 65%, 70%, 75%, 80%, 85%, 90%, 95%, 96%, 97%, 98%, 99% or 100% sequence identity with SEQ ID NO: 43. The spike protein conjugated to one or more tags and a protease recognition site is preferably encoded by a sequence having at least about 50%, 55%, 60%, 65%, 70%, 75%, 80%, 85%, 90%, 95%, 96%, 97%, 98%, 99% or 100% sequence identity with SEQ ID NO: 48.

The sequence of the protein conjugated to (optionally a linker and) the AMP preferably has at least about 50%, 55%, 60%, 65%, 70%, 75%, 80%, 85%, 90%, 95%, 96%, 97%, 98%, 99% or 100% sequence identity with SEQ ID NO: 44.

A preferred conjugate of the invention is a conjugation between a SARS-CoV-2 spike protein and mCRAMP. Preferably, the conjugate comprises a linker in between the spike protein and mCRAMP. Optionally, the conjugate further comprises one or more tags, such as a His-tag and a Twin strep tag. In addition or alternatively the conjugate comprises one or more protease cleavage sites, such as one or more HRV 3C recognition sites. A preferred conjugate of the invention has at least about 50%, 55%, 60%, 65%, 70%, 75%, 80%, 85%, 90%, 95%, 96%, 97%, 98%, 99% or 100% sequence identity with SEQ ID NO: 42. A preferred conjugate of the invention is encoded by a nucleotide sequence having at least about 50%, 55%, 60%, 65%, 70%, 75%, 80%, 85%, 90%, 95%, 96%, 97%, 98%, 99% or 100% sequence identity with SEQ ID NO: 47.

Preferably, the conjugate of the invention does not comprise a tag and/or a protease recognition site. The conjugate may comprise or consist of an antigen as defined herein, a linker and an AMP. Preferably, the linker is GGGSGGGSGGGS (SEQ ID NO: 12). Preferably, the spike protein has SEQ ID NO: 44. Preferably, the AMP is mCRAMP having SEQ ID NO: 1. A preferred conjugate of the invention has at least about 50%, 55%, 60%, 65%, 70%, 75%, 80%, 85%, 90%, 95%, 96%, 97%, 98%, 99% or 100% sequence identity with SEQ ID NO: 45. A preferred conjugate of the invention is encoded by a nucleotide sequence having at least about 50%, 55%, 60%, 65%, 70%, 75%, 80%, 85%, 90%, 95%, 96%, 97%, 98%, 99% or 100% sequence identity with SEQ ID NO: 50.

The EV71 VP1 protein can have at least about 35%, 40%, 45%, 50%, 55%, 60%, 65%, 70%, 75%, 80%, 85%, 90%, 95%, 96%, 97%, 98%, 99%, or about 100% sequence identity with SEQ ID NO: 14 (EV71 VP1). A preferred, preferably antigenic, fragment of VP1 or VP2 has at least about 35%, 40%, 45%, 50%, 55%, 60%, 65%, 70%, 75%, 80%, 85%, 90%, 95%, 96%, 97%, 98%, 99%, or about 100% sequence identity to at least one of SEQ ID NO: 15, 16 and 17.

The antigen coupled to the AMP may comprise or consists of one or more epitopes from a surface exposed domain of a surface exposed bacterial protein or lipoprotein. Preferably the surface exposed domain of a surface exposed protein or lipoprotein from a bacterium selected from a genus consisting of *Bordetella, Neisseria, Acinetobacter, Borrelia, Coxiella* and any of the other pathogenic bacterial genera mentioned above.

AMP—Antigen Production

The antigen and the AMP may be produced separately and conjugated after production. The antigen and/or the AMP may be produced using a cell-free system. Such cell-free system can be an in vitro peptide synthesis, such as but not limited to, Liquid phase peptide synthesis (LPPS) or solid phase peptide synthesis (SPPS). Alternatively or in addition, the AMP and/or antigen may be purified from a cell, tissue or bodily fluid that naturally comprises said antigen or said AMP. Alternatively or in addition, the antigen and/or AMP may be produced in a recombinant cell, modified to express or overexpress the antigen and/or the AMP. The AMP is preferably an AMP as defined herein above. Preferably, the AMP has a sequence having at least about 35%, 40%, 45%, 50%, 55%, 60%, 65%, 70%, 75%, 80%, 85%, 90%, 95%, 96%, 97%, 98%, 99%, or about 100% sequence identity to SEQ ID NO: 1.

Alternatively, the AMP and antigen may be produced as a single polypeptide, i.e. as a fusion protein comprising a first fusion partner and a second fusion partner, wherein the first fusion partner is an AMP and the second fusion partner is an antigen. Optionally, the fusion partners are separated by a linker. It is understood herein that the terms "first" and "second" do not particularly specify the N-terminal or C-terminal location of the respective fusion partners within the fusion protein. The terms "first" and 'second" are solely intended to indicate that the fusion protein comprises at least two fusion partners, i.e. an AMP and an antigen. Preferably the fusion protein comprises in an N-terminal to C-terminal direction an AMP, an optional linker, and an antigen. Alternatively, the fusion protein comprises in an N-terminal to C-terminal direction an antigen, an optional linker, and an AMP. The AMP of the fusion protein is preferably an AMP as defined herein above. Preferably, the fusion protein comprises an AMP having a sequence having at least about 35%, 40%, 45%, 50%, 55%, 60%, 65%, 70%, 75%, 80%, 85%, 90%, 95%, 96%, 97%, 98%, 99%, or about 100% sequence identity to SEQ ID NO: 1.

The fusion protein may be produced using a cell-free system. Such cell-free system can be in vitro peptide synthesis, such as but not limited to, Liquid phase peptide synthesis (LPPS) or solid phase peptide synthesis (SPPS). Alternatively or in addition, the fusion protein may be produced in a recombinant cell. A recombinant cell or "host cell" expressing at least one of the AMP, antigen or fusion protein as described herein can be any suitable host cell. It is understood herein that the cell expressing the AMP may be a different cell, i.e. derived from a different organism or from a different cell type, than the cell expressing the antigen. The host cell may be transformed, transfected, transducted, and the like with a nucleic acid construct encoding an AMP, an antigen or a fusion protein as defined herein. Hence, the term "host cell" means any cell type that is susceptible to transformation, transfection, transduction, and the like with said nucleic acid construct.

Alternatively or in addition, the genome of the host cell may be modified to express or overexpress an endogenously encoded AMP or antigen. Alternatively or in addition, the genome of the host cell may be modified to express or overexpress a mutated version of an endogenously encoded AMP or antigen, e.g. using site-specific editing technologies such as, but limited to, CRISR-Cas technology. The term "host cell" further encompasses any progeny of a parent cell that is not identical to the parent cell due to mutations that occur during replication.

The choice of a host cell may depend upon the type of AMP, antigen and/or fusion protein. The host cell may be any cell useful in the recombinant production of an AMP, antigen and/or fusion protein, e.g., a prokaryote or a eukaryote cell.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Neisseria, Bordetella, E. coli, Pseudomonas, Campylobacter, Flavobacterium, Fusobacterium, Helicobacter, Ilyobacter, Salmonella*, and *Ureaplasma*. A preferred gram-negative bacterium is a *Neisseria*, a *Bordetella* or an *E. coli*. A preferred *Neisseria* is at least one of a *Neisseria meningitidis, Neisseria gonorrhoeae* or *Neisseria lactamica*. A preferred *Bordetella* is at least one of a *Bordetella pertussis, Bordetella parapertussis* and *Bordetella bronchiseptica*. A preferred prokaryotic host cell is *E. coli*.

A preferred eukaryotic host cell is an animal cell, preferably a vertebrate cell, preferably a mammalian cell, preferably a human cell. Preferably, the cell is a cell from a cell line, preferably an immortalized cell line.

The host cell may be transformed, transfected, transducted, and the like with a nucleic acid construct encoding at least one of the antigen, AMP and fusion protein. Preferably, the nucleic acid construct comprises one or more regulatory elements controlling the expression of at least one of the AMP, antigen and fusion protein. Preferably, the regulatory elements comprise at least a promoter sequence. The skilled person understands that any promoter sequence suitable for expression in the selected host cell can be used. Preferably, the promoter is at least one of a constitutively active promoter or an inducible promoter. In case the host cell is a bacterial host cell used for expression of at least one of an AMP and a fusion protein, the promoter is an inducible promoter, such as but not limited to a chemically inducible promoter.

The produced AMP, antigen and/or fusion protein may be purified using any conventional means, such as, but not limited to one or more dialysis, filtration or purification steps.

OMV

The antigen conjugated to the AMP can form a complex with any suitable OMV. An OMV is a spherical budding of the outer membrane (OM) that are spontaneously produced by Gram-negative bacteria.

OMVs (also known as "blebs") for use in vaccines have traditionally been prepared by detergent extraction (a dOMV purification process), wherein detergents such deoxycholate are used to remove LPS and increase vesicle release. The LPS of most Gram-negative bacteria, such as *N. meningitidis* is highly toxic, yet residual amounts (approx. 1%) are needed in OMV to maintain vesicle structure and for adjuvant activity. A presumed initial step in the interaction between the AMP and the OMV is the binding of the AMP to the lipid A/inner core region of LPS. Hence it is preferred that the OMV maintains at least part of its LPS. An OMV in the complex as defined herein is therefore preferably is not a detergent-extracted OMV. It is understood however, that a process for preparing an OMV that is not a detergent-extracted OMV does not exclude the use of any detergents. The use of low concentration of detergent and/or the use of mild detergents are not excluded as long as the AMP is still capable of anchoring the antigen to the extracted OMV, e.g. at least about 50, 60, 70, 80, 90, 95 or 99% of the AMP-conjugated antigens are complexed with the extracted OMV as compared to the amount of AMP-conjugated antigens that are complexed with a spontaneous or supernatant OMV.

Preferably, the OMV that forms a complex with the antigen and AMP is a spontaneous OMV or a native OMV. The OMV is preferably a native OMV. The production of native OMV is well-known in the art, and has e.g. been described in Saunders et al. (1999, Infect Immun, 67, 113-119), van de Waterbeemd et al. (2012, Vaccine, 30: 3683-3690) and in WO2013006055. Methods for preparing sOMV are e.g. described in van de Waterbeemd et al. (2013, PLoS ONE, 8(1): e54314. doi:10.1371/journal- .pone.0054314) and in Lee et al. (2007, Proteomics, 7: 3143-3153), all of which are incorporated herein by reference.

The LPS of the OMV as described herein may comprise at least partly detoxified LPS. For example, the LPS may have a modified oligosaccharide structure so as to remove possible epitopes that are suspected to provoke autoimmune responses, and/or to increase binding to dendritic cells and adjuvant activity. In addition or alternatively, the LPS may have a modified Lipid A moiety, wherein e.g. one or more acyl chains are shortened or absent as compared to the wild type Lipid A moiety.

The OMV in the complex of the invention is preferably obtainable from a Gram-negative bacterium that has a genetic modification selected from the group consisting of: (i) a genetic modification that alters the lipopolysaccharide (LPS) biosynthesis pathway, preferably in order to obtain less endotoxic and reactogenic variants; (ii) a genetic modification that increases OMV production by removing outer membrane anchor proteins; and (iii) a genetic modification that removes immune-modulating components which may trigger an undesired type of immune response. In addition or alternatively, the Gram-negative bacterium may comprise at least one of (iv) a genetic modification that causes outer membrane retention of normally secreted antigens; and, (v) a genetic modification that introduces expression of heterologous antigens from other pathogens than the host OMV producing strain.

Preferably, the OMV is obtainable from a Gram-negative bacterium, wherein the Gram-negative bacterium comprises one or more genetic mutations, causing the bacterium to produce an LPS having a reduced (endo)toxicity. Preferably, the LPS retains at least part of its adjuvant activity. Preferably, the modification reduces or eliminates the expression of at least one of an lpxL1, lpxL2, lpxA, lpxD and lpxK gene or a homologue thereof. Preferably, the modification reduces or eliminates the expression of at least one of an endogenous lpxL1, lpxL2, lpxA, lpxD and lpxK gene or a homologue thereof.

Preferably, the Gram-negative bacterium has a genetic modification reduces or eliminates expression of an lpxL1 gene or a homologue thereof, wherein the lpxL1 gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 5.

In addition or alternatively, the OMV is obtainable from a Gram-negative bacterium, wherein the Gram-negative bacterium comprises one or more genetic mutations causing the bacterium to produce an LPS having a reduced (endo) toxicity and wherein preferably, the modification increases the expression of at least one of a, lpxP, lpxA, lpxD, lpxE, lpxF and pagL gene, or a homologue thereof. Preferably, the modification increases the expression of at least one of a heterologous lpxP, lpxA, lpxD, lpxE, lpxF and PagL gene.

Preferably, the Gram-negative bacterium has a genetic modification that introduces or increases the expression of an lpxP gene or a homologue thereof, wherein the lpxP gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 6.

Preferably, the Gram-negative bacterium has a genetic modification that introduces or increases the expression of an lpxA gene or a homologue thereof, wherein the lpxA gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 7.

Preferably, the Gram-negative bacterium has a genetic modification that introduces or increases the expression of an lpxD gene or a homologue thereof, wherein the lpxD gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 8.

Optionally, the modified Gram-negative bacterium is modified to reduce or eliminate the expression of at least one of an endogenous lpxP, lpxA, lpxD, lpxE, lpxF and pagL gene.

The Gram-negative bacterium, from which the OMV of the complex of the invention is obtainable, may comprise a genetic modification that reduces or eliminates expression of a gene encoding an anchor protein between outer membrane and peptidoglycan in order to increase vesicle formation and thereby increase OMV yield.

A suitable genetic modification for this purpose e.g. reduces or eliminates expression of an OmpA homologue, which are commonly found in Gram-negative bacteria, e.g. the RmpM protein in *Neisseria* (Steeghs et al., 2002 Cell Microbiol, 4:599-611; van de Waterbeemd et al., 2010 Vaccine, 28:4810-4816). Thus preferably, the genetic modification reduces or eliminates expression of an ompA gene or a homologue thereof, more preferably a rmpM gene or a homologue thereof. Preferably, the Gram-negative bacterium has a genetic modification that reduces or eliminates expression of an rmpM gene or a homologue thereof, wherein the rmpM gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 9. Eliminating the RmpM expression preferably increases the OMV release.

In an embodiment, the Gram-negative bacterium for the production of an OMV for a complex as defined herein comprises a mutation that results in the retention of a Prn93 (93 kDa Pertactin) in the outer membrane.

A Gram-negative bacterial host cell for producing the OMV of the complex of the invention can further have one or more genetic modifications that reduce or eliminate the expression of a gene selected from the group consisting of cps, ctrA, ctrB, ctrC, ctrD, exbB, exbD, frpB, galE, htrB, msbB, lpbB, lpxK, lpxL1, nmb0033, opA, opC, rmpM, phoP, pi/C, pmrE, pmrF, porA, porB, siaA, siaB, siaC, siaD, synA, synB, sync, tbpA and tbpB, or homologues thereof, preferably cps and porB or homologues thereof. Many of these mutations are reviewed in WO02/09746.

A reduction of expression is preferably a reduction in the expression as compared to an otherwise identical bacterial host cell not comprising the genetic modification. Preferably a genetic modification as defined herein reduces the expression at least about 10%, 20%, 30%, 40%, 50%, 60%, 70%, 80%, 90%, 95%, 98% or 100%. A 100% reduction is understood herein as the elimination of expression.

The Gram-negative bacterium may comprise a genetic modification in a cps locus, preferably reducing or eliminating the expression of a gene located in the cps locus, e.g. a gene as specified in Table 2 and 3 of Harrison et al (Emerg Infect Dis. 2013 April; 19(4): 566-573), which is incorporated herein by reference. Preferably the genetic modification in the cps locus results in at least a reduction or elimination of siaD expression.

Preferably, the Gram-negative bacterial host cell for producing the OMV of the complex of the invention can have one or more genetic modifications that reduce or eliminate the expression of a gene selected from the group consisting of lpxL1, porA, porB, rmpM, and siaD. Preferably, the Gram-negative bacterial host cell for producing the OMV of the complex of the invention has one or more genetic modifications that reduce or eliminate the expression of a gene selected from the group consisting of lpxL1, porA, rmpM and siaD.

Preferably, the Gram-negative bacterium has a genetic modification that reduces or eliminates expression of an siaD gene or a homologue thereof, wherein the siaD gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 38. The reduction, preferably the deletion, of siaD expression preferably results in the removal of the capsular polysaccharide, which reduces the invasiveness of the bacteria.

Preferably, the Gram-negative bacterium has a genetic modification that reduces or eliminates expression of an porA gene or a homologue thereof, wherein the porA gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 39.

Preferably, the Gram-negative bacterium has a genetic modification reduces or eliminates expression of an porB gene or a homologue thereof, wherein the porB gene or homologue thereof preferably encodes a protein having at least 35%, 40%, 45%, 50%, 55%, 60%, 65%, 70%, 75%, 80%, 85%, 90%, 95%, 96%, 97%, 98%, 99% or 100% sequence identity with the amino acid sequence of SEQ ID NO: 40.

In addition or alternatively, the Gram-negative bacterium for the production of an OMV may comprise a mutation that reduces or eliminates Pertussis toxin (Ptx) toxicity.

A Gram-negative bacterium for producing the OMV that forms part of a complex as defined herein preferably belongs to a genus selected from the group consisting of *Neisseria*, *Bordetella*, *Escherichia* and *Salmonella*. A preferred *Neisseria* is at least one of a *Neisseria meningitidis*, *Neisseria gonorrhoeae* or *Neisseria lactamica*. A preferred *Bordetella* is at least one of a *Bordetella pertussis*, *Bordetella parapertussis* and *Bordetella bronchiseptica*. Preferably is bacterial host cell that belongs to a species selected from the group consisting of *Neisseria meningitidis*, *Bordetella pertussis*, *Escherichia coli* and *Salmonella enterica*. A preferred *Neisseria meningitidis* serotype is serotype A, B, C, W135, X, and Y, preferably serotype B. A preferred *Neisseria meningitidis* strain is H44/76.

A preferred Gram-negative bacterial cell for OMV production is a *Neisseria* or *Bordetella* cell as specified herein in the example section.

Preferably, the OMV-producing cell is a *Neisseria meningitidis* having a mutation in at least one of a porB, rmpM and lpxL1 gene. Preferably, the OMV-producing cell is a *Neisseria meningitidis* having a mutation in at least one of a porA, rmpM and lpxL1 gene. Preferably, the OMV-producing cell is a *Neisseria meningitidis* having a mutation in at least one of a porB, rmpM, lpxL1 and cps gene. Preferably, the OMV-producing cell is a *Neisseria menin-*

*gitidis* having a mutation in at least one of a porA, rmpM, lpxL1 and cps gene. Preferably, the OMV-producing cell is a *Neisseria meningitidis* having a mutation in at least one of a porA, rmpM, lpxL1 and siaD gene. Preferably, the OMV-producing cell is a *Neisseria meningitidis* having a mutation in at least one of a porB, rmpM, LpxL 1 and siaD gene.

In a further aspect, the invention relates to a pharmaceutical composition comprising a complex as defined herein and a pharmaceutically accepted excipient. The composition preferably comprises a pharmaceutically acceptable carrier, medium or delivery vehicle as are conventionally known in the art (see e.g. "Handbook of Pharmaceutical Excipients", Rowe et al eds. 7th edition, 2012, www.pharmpress.com). Pharmaceutically acceptable stabilizing agents, osmotic agents, buffering agents, dispersing agents, and the like may also be incorporated into the pharmaceutical compositions. The preferred form depends on the intended mode of administration and therapeutic application. The pharmaceutical carrier can be any compatible, non-toxic substance suitable to deliver the active ingredients, i.e. the complex of the invention to the patient. Pharmaceutically acceptable carriers for parenteral delivery are exemplified by sterile buffered 0.9% NaCl or 5% glucose optionally supplemented with a 20% albumin. Alternatively, the OMV comprising the AMP-antigen conjugate can be suspended in Phosphate buffer saline (PBS). Preparations for parental administration must be sterile. The parental route for administration of the OMV complex of the invention is in accord with known methods, e.g. injection or infusion by intravenous, intraperitoneal, intramuscular, intranasal, intraarterial or intralesional routes.

The OMV complex is preferably administered intranasally. In this embodiment, a pharmaceutical composition comprising the OMV complex is preferably suitable for intranasal administration. Nasal, or intranasal, administration is herein understood as a route of administration in which the formulation is preferably insufflated through the nose. The composition comprising the OMV complex of the invention may be sprayed or dripped in at least one nostril, preferably into both nostrils. The composition may be administered using a nose dropper as defined herein below.

The complex or pharmaceutical composition may be administrated continuously by infusion or by bolus injection. A typical pharmaceutical composition for intramuscular injection would be made up to contain, for example, 1-10 ml of phosphate buffered saline comprising the effective dosages of the OMV complex of the invention. Methods for preparing parenterally administrable compositions are well known in the art and described in more detail in various sources, including, for example, "Remington: The Science and Practice of Pharmacy" (Ed. Allen, L. V. 22nd edition, 2012, www.pharmpress.com). The pharmaceutical composition is preferably a vaccine, preferably an a-cellular vaccine.

The composition may comprise one or more additional adjuvants e.g. to further boost an immune response. The adjuvant may be an organic or inorganic adjuvant. A preferred inorganic adjuvant is an aluminium salt, such as, but not limited to aluminium phosphate and aluminium hydroxide. A preferred organic adjuvant may be a modified LPS, preferably modified Neisserial or *Bordetella* LPS, modified LOS, squalene, QS21, or monophosphoryl lipid A (MPL). The adjuvant may be selected from the group consisting of alum, aluminum hydroxide, aluminum phosphate, calcium phosphate hydroxide, paraffin oil, squalene, detergents (e.g. Quil A), (plant) saponins, cytokine (e.g. IL-1, IL-2, or IL-12), Freund's complete adjuvant and Freund's incomplete adjuvant. The use of specific adjuvants, the relative and absolute amounts of substances in the compositions and the doses regimen for the administration are known or may be determined by the skilled person and may be adapted for the circumstances such as the particular pathogenic infection or the status of the particular subject to be treated. The doses regimen may comprise a single dose but may also comprise multiple doses, for instance booster doses, and may preferably be administered orally, intranasally or parenterally, preferably intranasally or intramuscularly. Various doses regimens for vaccination purposes are known in the art and may be suitably adapted by the skilled person.

In an aspect the invention pertains to a complex as defined herein or a pharmaceutical composition as defined herein for use as a medicament. Put differently, the invention thus pertains to the use as medicament of at least one of a complex and a pharmaceutical composition of the invention. The invention further concerns a method of treatment using at least one of an OMV complex and a pharmaceutical composition as defined herein.

In another aspect, the invention pertains to a complex of the invention or a pharmaceutical composition comprising said complex for the prevention or treatment of a disease, preferably an infectious disease, or tumour associated with an antigen as herein defined above. In this aspect, the invention thus relates to a method for vaccination against, or for prophylaxis or therapy of a disease, preferably an infectious disease, or tumour by administration of a therapeutically or prophylactically effective amount of (a pharmaceutical composition comprising) a complex of the invention, to a subject in need of prophylaxis or therapy. The invention also relates to a complex or pharmaceutical composition use as a medicament, preferably a medicament for vaccination against, or for prophylaxis or therapy of a disease, preferably an infectious disease, or tumour. In a further aspect, the invention concerns a complex as defined herein or a pharmaceutical composition as defined herein for use in a treatment comprising inducing or stimulating an immune response in a subject against the antigen. Preferably the treatment is for preventing or treating an infectious disease or tumour associated with the antigen present in the complex of the invention, wherein the antigen preferably is an antigen as herein defined above.

In an aspect, the invention relates to a complex as defined herein for use in an immunotherapy. Preferably, the immunotherapy is an immunotherapy of a cancer or of a neurodegenerative disease, including e.g. Alzheimer's disease or Parkinson's disease.

In an aspect, the complex of the invention is for use in preventing and/or reducing the spread of an infection, such as a bacterial or viral infection. The complex of the invention may be used as a vaccine, such as, but not limited to a vaccine against SARS-CoV-2.

In a further aspect, the invention pertains to an AMP as defined herein conjugated to an antigen as defined herein. Preferably, the AMP is covalently linked to the antigen, optionally using a linker. The linker can a linker as defined herein. The AMP conjugated to the antigen is preferably a single polypeptide. The invention therefore also pertains to a fusion protein, wherein a first fusion partner is an AMP, preferably an AMP as defined herein, and a second fusion partner, wherein the second fusion partner is preferably an antigen, preferably an antigen as defined herein.

The invention further concerns a recombinant host cell expressing an AMP as defined herein. The same host cell may further express an antigen, preferably an antigen as defined herein. The host cell may be a host cell as defined herein above. The AMP and the antigen may be part of a single fusion protein as defined herein.

The invention further relates to a combination of a nucleic acid encoding an AMP and a nucleic acid encoding an antigen. Said combination of nucleic acids may be part of a single nucleic acid construct. The nucleic acid may further comprise one or more regulatory elements to control the expression of the AMP and the antigen. The AMP and antigen may be part of a single fusion protein as defined herein. Means and methods for constructing expression constructs for expression of the protein in a host cell as defined herein are generally well-known in the art.

The invention also concerns a method for producing a complex as defined herein. Preferably, the method comprise the steps of: culturing a population of Gram-negative bacteria as defined herein under conditions conducive for the production of OMV; ii) recovering the OMV produced in i); iii) contacting the OMV recovered in ii) with an AMP conjugated to an antigen as defined herein, under conditions conducive to the formation of a non-covalent complex between the AMP and the OMV; and vi) optionally, recovery of the complex. The production and purifying/extraction of OMV can be performed using any suitable method known in the art. Similarly, the production and purifying/extraction of AMP/antigen/fusion protein can be performed using any suitable method known in the art. The method for producing OMV of the complex of the invention is further preferably, a detergent-free method as herein defined and described above.

In an aspect, the invention concerns a combination of an OMV and an AMP, wherein the AMP is conjugated to an antigen.

In a further aspect, the invention concerns a kit of parts, wherein one vial comprises an OMV, preferably an OMV as defined herein and an AMP conjugated to an antigen, preferably as defined herein above. The kit may comprise a second vial with e.g. a pharmaceutical buffer. Alternatively or in addition, the kit of parts may comprise one vial comprising an OMV, preferably an OMV as defined herein, and a second vial comprising an AMP conjugated to an antigen, preferably as defined herein above. Alternatively in addition, the kit of parts may comprise one vial comprising an OMV, preferably an OMV as defined herein, one vial comprising an AMP, preferably an AMP as defined herein and one vial comprising an antigen, preferably an antigen as defined herein.

Preferably, the volume of any of the vials within the kit do not exceed 100 mL, 50 mL, 20 mL, 10 mL, 5 mL, 4 mL, 3 mL, 2 mL or 1 mL.

The reagents may be present in lyophilized form, or in an appropriate buffer. The kit may also contain any other component necessary for carrying out the present invention, such as buffers, pipettes, microtiter plates, injection needles and/or written instructions. Such other components for the kits of the invention are known to the skilled person.

It is further understood that the use of the composition in treatments of medical conditions as specified herein also includes the use of the compositions for the manufacture of a medicament for the corresponding medical treatments, as well as, methods for treating a subject suffering from such medical conditions by administering an effective amount of the compositions to the subject.

In a further aspect, the invention pertains to a nasal dropper bottle comprising a container comprising the composition of the invention. The nasal dropper bottle can be any nasal dropper bottle described in the art. Typically, the nasal dropper bottle may comprise a pipette (open at both ends), a compressible bulb, a container for containing liquids and a bottle cap. One end of the pipette is preferably placed into the container and the compressible bulb is preferably mounted on the other end of the pipette. When the free end of the pipette is held into the container comprising the composition of the invention and the compressible bulb is compressed, the air inside the bulb will be expelled from into the container. When the pressure on the compressible bulb is subsequently released, The elasticity of the bulb allows it to return to its initial volume, creating a vacuum in the bulb which allows the pipet to be filled with the composition of the invention. Compressing the bulb anew will preferably release the composition in drops from the pipet. The pipette is usually affixed to the bottle cap, usually mounted in the center of the cap in a sealed relationship. The bottle cap comprising the pipette can be screwed onto the container, thereby creating an air tight liquid container that will prevent spilling of the liquid.

In yet another aspect, the invention provides for a nasal spray comprising a bottle or equivalent receptacle comprising the composition of the invention. The nasal spray can be any nasal spray described in the prior art. Typically, the nasal spray comprises of a bottle containing the composition of the invention. The bottle is further preferably provided with a part for dispensing the composition into the nostril. The solution can then be squirted into the nostril by any suitable means, for instance by means of a pump, by deformation of the bottle or by using a suitable propellant. In one embodiment.

In this document and in its claims, the verb "to comprise" and its conjugations is used in its non-limiting sense to mean that items following the word are included, but items not specifically mentioned are not excluded.

All patent and literature references cited in the present specification are hereby incorporated by reference in their entirety.

The following examples are offered for illustrative purposes only, and are not intended to limit the scope of the present invention in any way.

FIGURE LEGEND

FIG. 1. Exemplary schematic representation of an embodiment of the invention. A) OMVs and antigens are prepared separately and tagged together using an AMP, B) OMV, mCRAMP and an exemplary antigen (EV71 VP1 or pertactin).

Figure 2A:
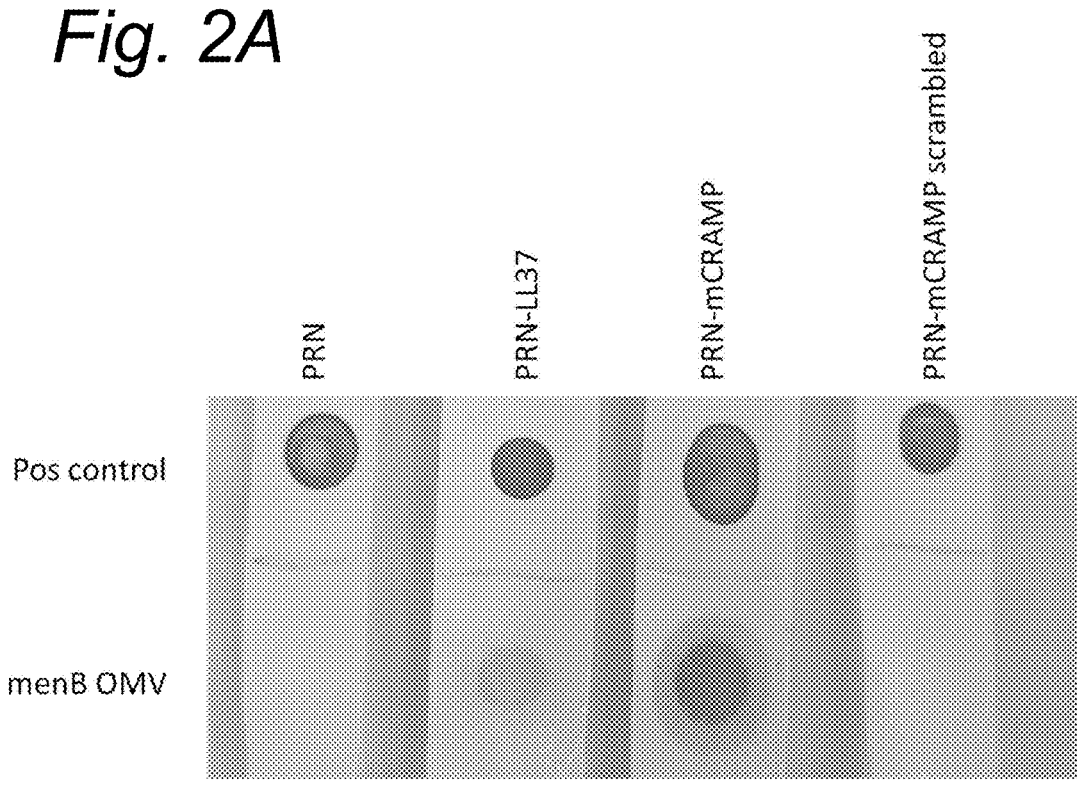
Figure 2B:
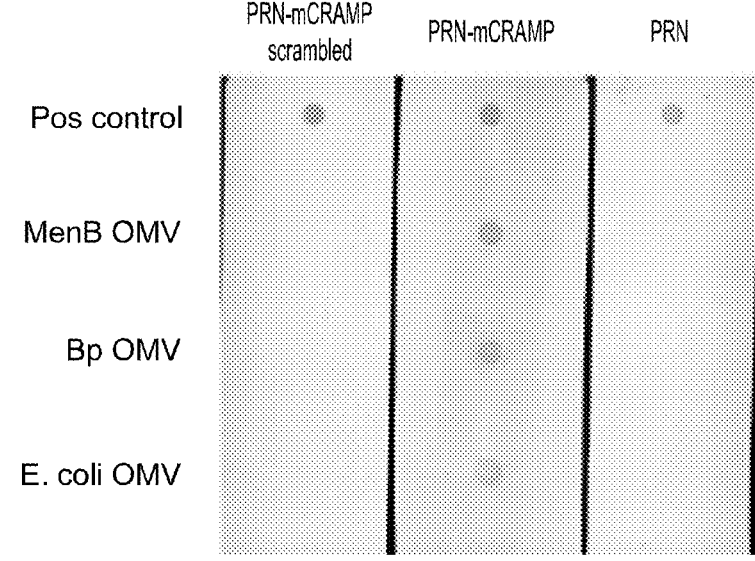

FIG. 2. A) Dot blot: Association of pertactin to OMVs through linker mCRAMP or LL37. B. Dot blot: PRN binding to OMVs from 3 different bacteria using an mCRAMP linker. C. Quantitative analysis of PRN binding to OMVs.

Figures 2C, 3:
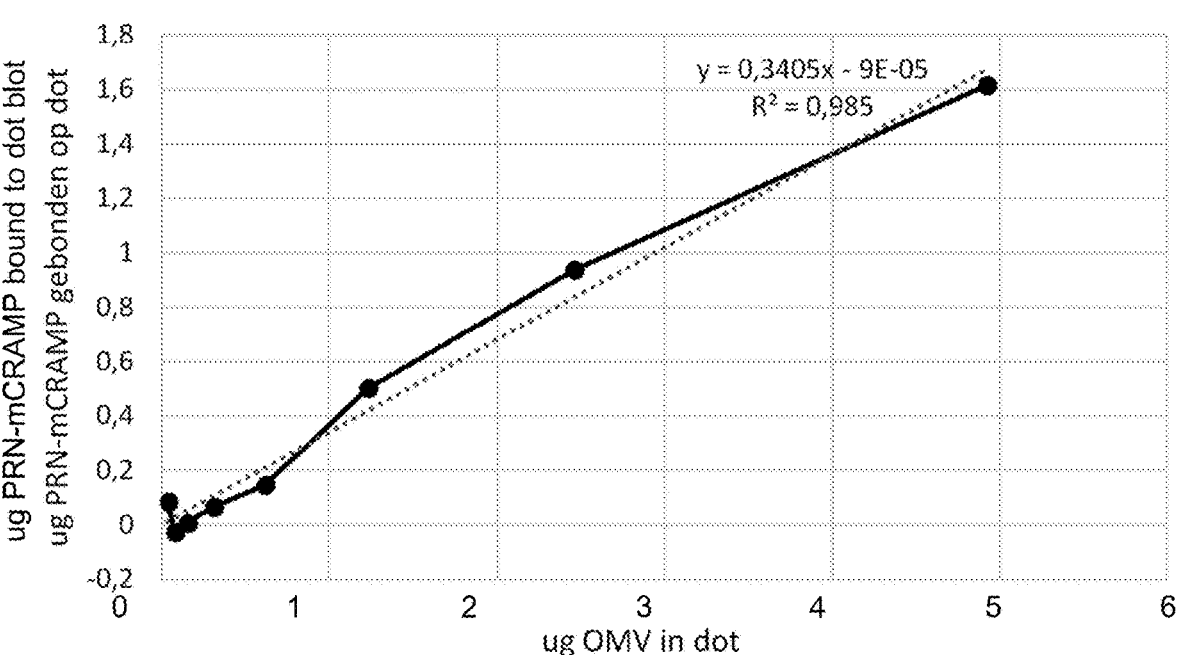

FIG. 3. Total IgG antibody titers against EV71 VP1 protein. Mice were immunized at day 0 and day 28 with peptide and protein based vaccine candidates. At day 42 sera were collected and tested for the presence of IgG antibodies against EV71 VP1 protein. The depicted symbols represent antibody titers from the serum of an individual mouse.

Figure 4A:
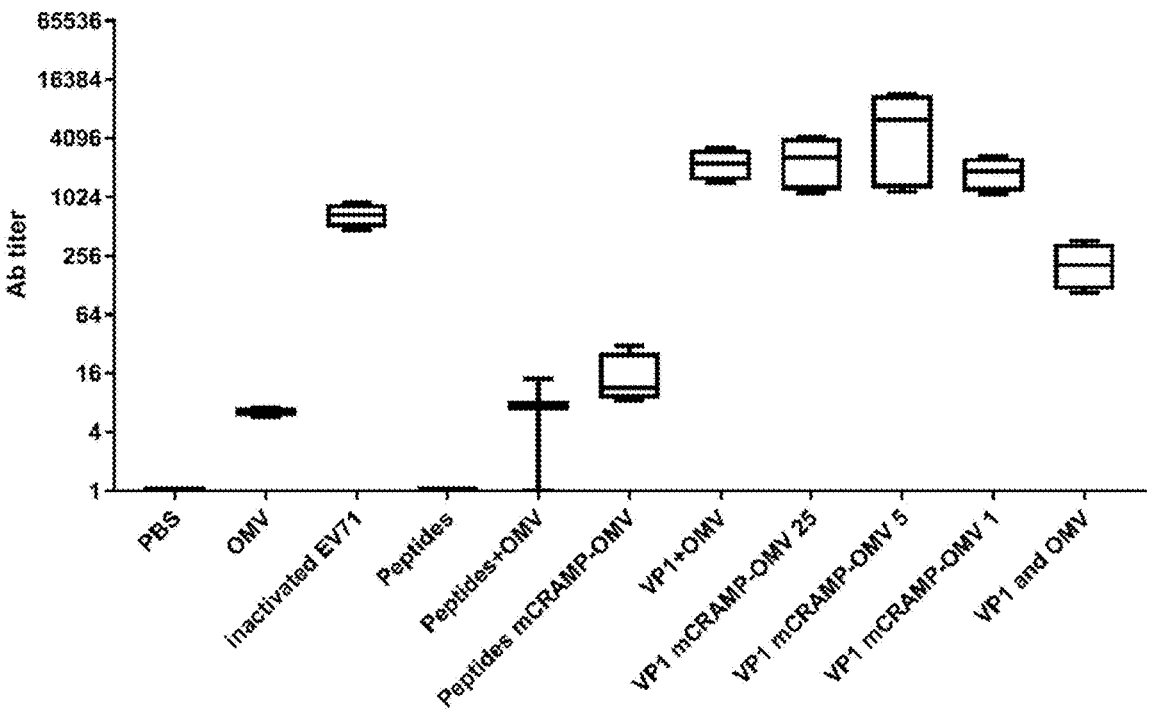
Figure 4B:
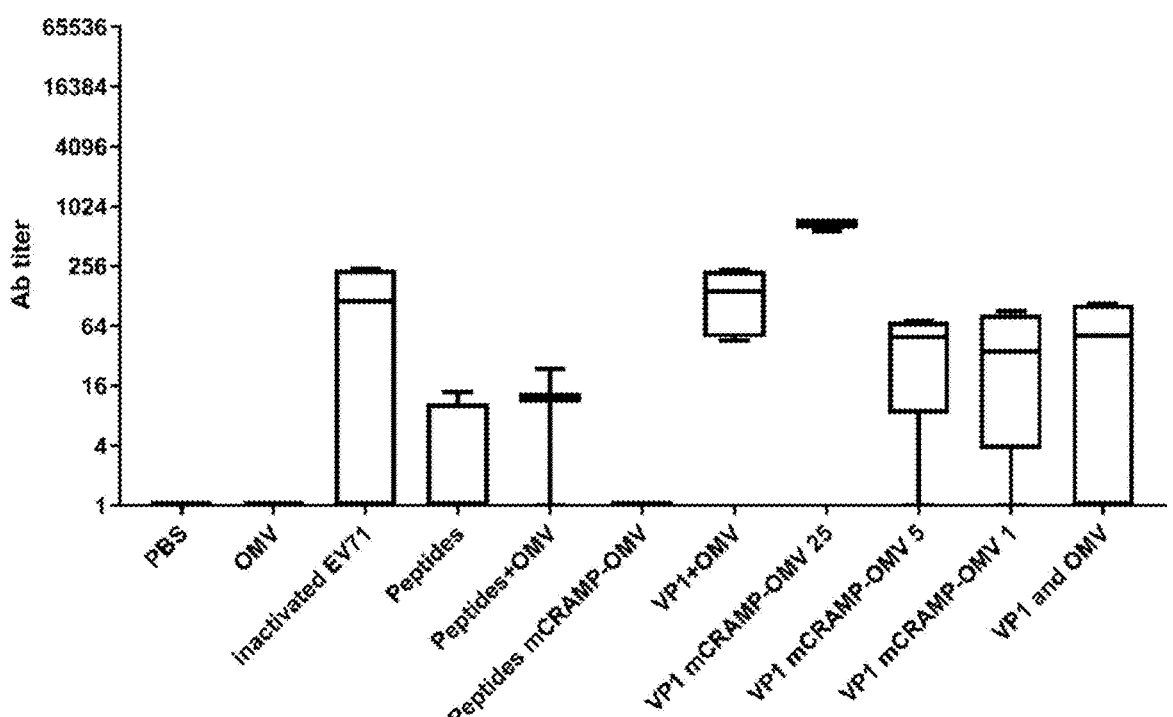

FIG. 4. Antibody responses of mice after immunization with EV71 vaccine candidates. Mice were immunized at day 0 and day 28 with peptide and protein based vaccine candidates. At day 42 sera were collected and tested for the presence of (A) IgG1 and (B) IgG2A antibodies against EV71 VP1 protein. Sera of five mice were pooled from a total of 10 mice per group. Data expressed as the mean±SD. Results are from two pooled sera per group and duplicates.

Figure 5:
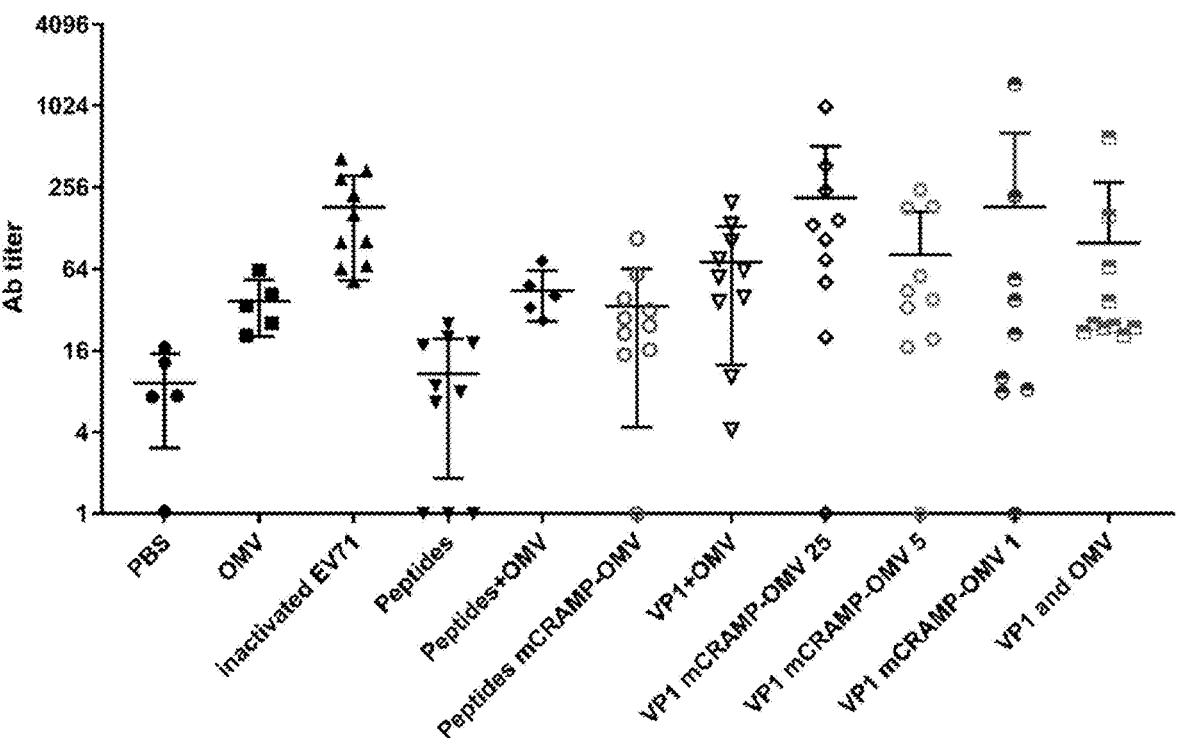

FIG. 5. Total IgG antibody titers against EV71 virus C4 genotype. Mice were immunized at day 0 and day 28 with peptide and protein based vaccine candidates. At day 42 sera were collected and tested for the presence of IgG antibodies against EV71 virus. The depicted symbols represent antibody titers from the serum of an individual mouse.

Figure 6:
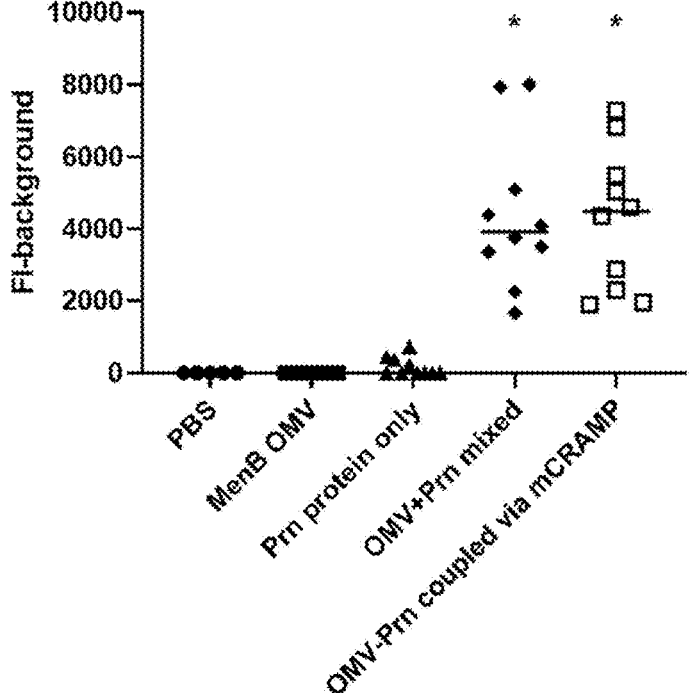

FIG. 6. Anti-Prn antibody titers in serum. Individual titers and the mean±standard deviation are depicted. *=statistically significant difference with placebo treated group.

Figure 7A:
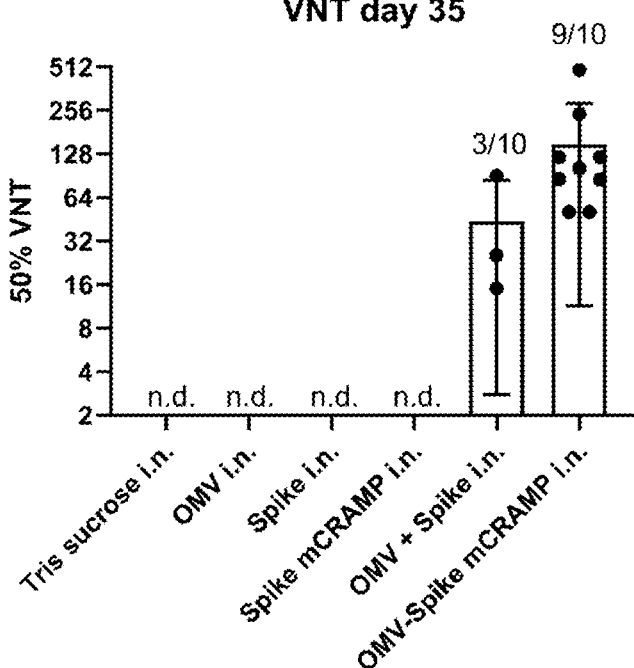
Figure 7B:
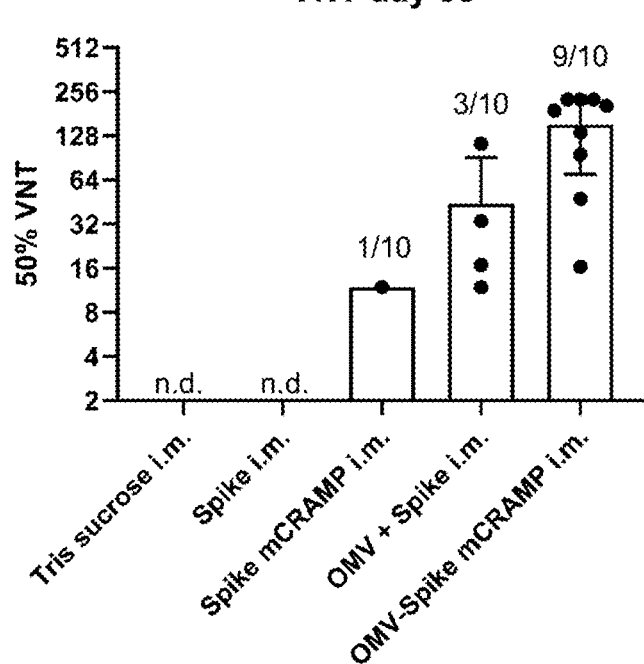

FIG. 7. Intranasal (A) and intramuscular (B) vaccination with OMV-Spike strongly induces the capacity of mouse serum to neutralize SARS-CoV2. VNT=virus neutralisation titre, i.n.=intranasal and i.m.=intramuscular.

Figure 8A:
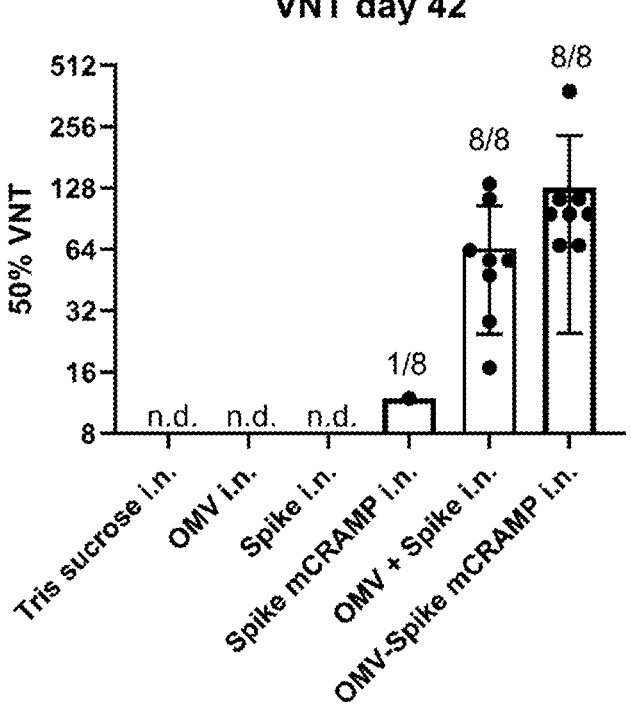
Figure 8B:
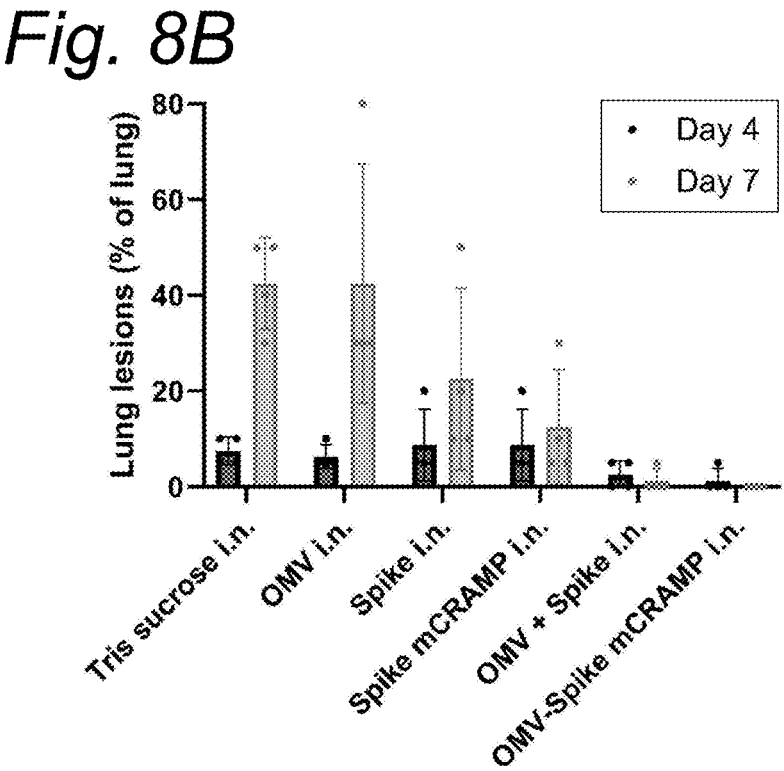

FIG. 8. A) Intranasal vaccination with OMV-Spike strongly induces the capacity of hamster serum to neutralize SARS-CoV2 and B) vaccinated hamsters develop almost no lung lesions after challenge with SARS-CoV2.

Figure 9A:
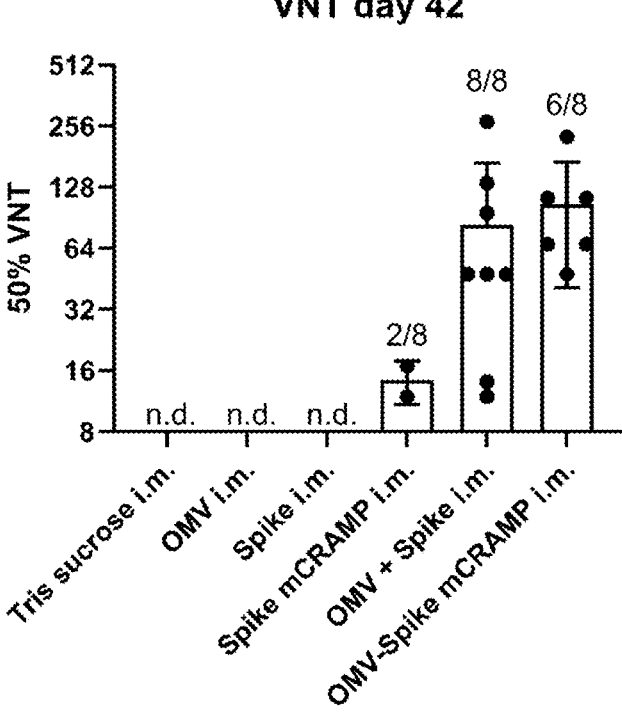
Figure 9B:
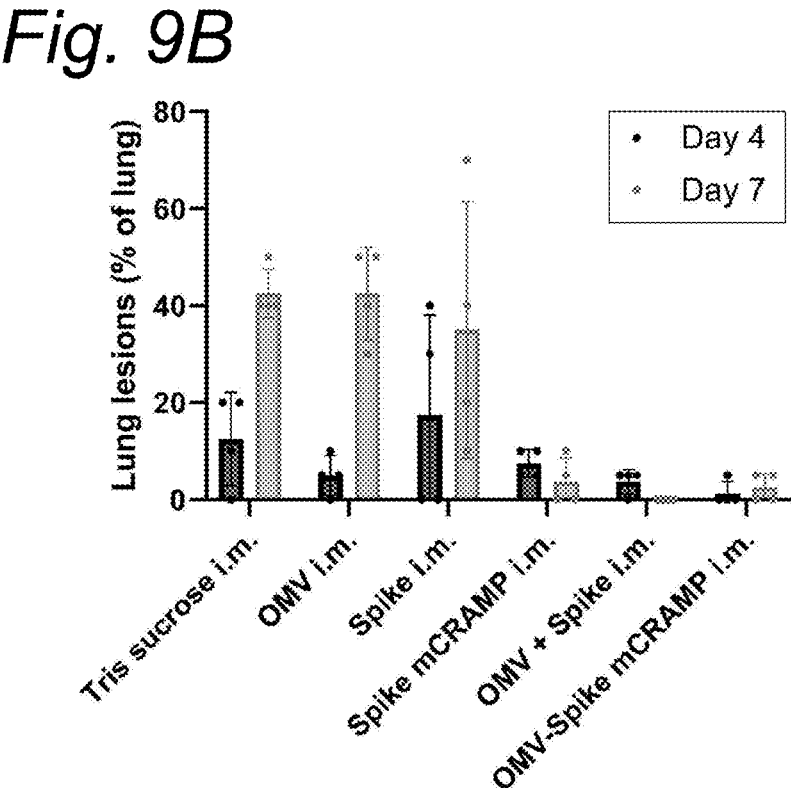

FIG. 9. A) Intramuscular (i.m.) vaccination with OMV-Spike induces the capacity of hamster serum to neutralize SARS-CoV2, although not as efficiently as intranasal (i.n.) vaccination, and B) vaccinated hamsters develop almost no lung lesions after challenge with SARS-CoV2

EXAMPLES

Example 1

The virulence factor Pertactin (PRN), from *Bordetella pertussis*, was coupled to human antimicrobial peptide LL-37 (SEQ ID NO: 22), or the murine variant thereof, called mCRAMP (SEQ ID NO: 20). It is expected that the coupled peptide will cause PRN to bind to OMVs after simply mixing them. As control proteins, PRN on its own (SEQ ID NO; 19) and PRN are linked to a scrambled version of mCRAMP (SEQ ID NO: 21), which should not bind to OMVs, were used. All proteins are provided with a His tag and produced as a recombinant protein. The OMVs used are from *Neisseria meningitidis* (ΔPorB ΔRmpM ΔlpxL1 Δcps).

Materials and Methods

Dot Blot Stocks

| | |
|---|---|
| p69 | 0.35 mg/ml |
| P69 mCRAMP | 0.54 mg/ml |
| p69 mCRAMP scambled | 1.19 mg/ml |
| OMV (MenB) | 1.23 mg/ml |

Dot Blot

Two 1.5 µl dots were placed on cut-out pieces of nitrocellulose. One dot of PRN, PRN-LL37, PRN-mCRAMP or PRN-scrambled mCRAMP and one dot of OMV. Subsequently, the nitrocellulose pieces were washed with three times with 1 ml of Wst buffer (0.1 M Tris, 1.54 M NaCl, 5% Tween-80, pH=7.4) for five minutes. Next, the nictrocellulose pieces were incubated with 5 µl of the same protein as in the first dot. The staining procedure consisted of: washing with Wst buffer, incubation with anti-his Ab in Wst buffer, washing with Wst buffer, incubation with anti-mouse IgG-AP in wst-0.5%, washing with Wst buffer, washing with MiliQ, incubation with AP mix and wash again with MiliQ. The amount of bound protein was determined using CLIQS software, optionally in combination with a Bio-Rad Dot blot apparatus. To determine the amount of OMV-bound protein, the intensity of the stained dots was compared with dilution series of control protein and OMVs using standard procedures.

Results

A dot blot was used to demonstrate binding of other mCRAMP/LL-37 fusion proteins. FIGS. 2A and B show that PRN linked to LL-37 or mCRAMP does bind to OMVs, but only PRN or linked to scrambled mCRAMP does not bind to the OMVs. FIG. 2C shows the strong correlation between the amount of OMV present on the dot blot and the amount of bound PRN-mCRAMP.

Example 2

The inventors have assessed the induction of (neutralizing) antibodies in response to antigens derived from enterovirus-71 attached to OMVs. The antigen was produced with the C-terminal tag LL-37 or the mouse ortholog of the human antimicrobial peptide LL-37 (mCRAMP). These proteins or peptides were individually combined with purified OMVs to form OMV-antigen complexes.

Materials and Methods

Outer Membrane Vesicle (Nonamen)

A native meningococcal OMV vaccine has been developed in the past by the Dutch Vaccine Institute (NVI)/Institute for translational vaccinology (Intravacc), which consists of OMVs from 3 meningococcal strains engineered for high blebbing (rmpM mutation), detoxified LPS (lpxL1 mutation), loss of capsule (deletion of entire locus) and PorB (gene deletion), and expression of three different porA genes per strain. OMVs from one strain (expressing PorA subtypes 14, 1 and 3) were used as carrier in our experiments.

Antigenic Target

The EV71 virus was evaluated as a first candidate and linear epitopes of viral proteins of EV71 (VP1 and VP2) are well described in literature. EV71 is the main cause of hand-foot-mouth disease (HFMD) and a major problem in Asia. EV71 particles are composed of a single RNA molecule protected by four viral capsid proteins, VP1 to VP4, of which the VP1 contains many neutralization epitopes and behaves as major immunogenic capsid protein, EV71-VP1 is thus an ideal target for vaccine development.

EV71 Viral Protein 1

In this study the complete VP1 protein of EV71-C4 (NCBI acces. #JN256062) was coupled to OMVs to investigate the feasibility of using OMVs as platform for virus vaccine development. VP1 is N-terminally linked to a 6×HIS tag for purification (SEQ ID NO: 23) and the antimicrobial peptide of human (LL-37) or mouse (mCRAMP) was attached to the C-terminus. The sequences of the recombinant proteins are depicted in respectively SEQ ID NO: 24 (VP1-mCRAMP) and SEQ ID NO: 25 (VP1-LL37). The complete protein is believed to associates with the OMV via the C-terminally linked LL-37 or mCRAMP. The expression of the protein was evaluated in 293 cells (mammalian expression) and E. coli bacteria.

The HIS-VP1-LL-37 protein is successfully produced by the 293-6E cells. The estimated molecular weight of ~50 kDa was detected by Western blot analysis under reducing conditions in cell culture supernatant and cell debris (data not shown). The expression level of LL-37 was ~0.1~0.5 mg/L. Higher yields of the HIS-VP1-LL37 protein was achieved by expression in E. Coli. Protein was obtained from inclusion bodies after denaturing followed by one-step purification using an Ni column. Around 0.14-0.20 mg/ml of 70-85% pure protein was recovered from 1 liter scale.

Peptides

In multiple papers linear peptide epitope (1-3,5) from VP1 and VP2 of EV71 are described that induce antibodies after immunization in mice. Antibodies that recognize a selection of these peptides are able to also neutralize the virus in vitro. As several genotypes of EV71 are known, the inventors made a selection. To this end, the C4 and B4 genotypes are the most prevalent in the outbreaks that have occurred in last 10 years. The variance in the peptide sequences between the C4 and B4 genotypes of the linear epitopes, along with the peptides employed in this study are presented in Table 1.

TABLE 1

Overview of the EV71 related peptides.

| SEQ ID NO | Sequence | MW (Da) |
|---|---|---|
| 26 | YPTFGEHKQEKDLEYGAC | 2156.5 |
| 27 | DTGEVPALQAAEIGA | 1482.7 |
| 28 | AGGTGTEDSHPPYKQ | 1585.8 |
| 29 | DTGEVPALQAAEIGAGGGSGGGSGGGS <u>GLLRKGGEKIGEKLKKIGQKIKNFFQKLVPQPEQ</u> | 6118.1 |
| 30 | YPTFGEHKQEKDLEYGACGGGSGGGSGGGS <u>GLLRKGGEKIGEKLKKIGQKIKNFFQKLVPQPEQ</u> | 6791.9 |
| 31 | AGGTGTEDSHPPYKQGGGSGGGSGGGS <u>GLLRKGGEKIGEKLKKIGQKIKNFFQKLVPQPEQ</u> | 6221.1 |
| 32 | HHHHHHDTGEVPALQAAEIGA <u>GLLRKGGEKIGEKLKKIGQKIKNFFQKLVPQPEQ</u> | 6166.3 |
| 33 | HHHHHHYPTFGEHKQEKDLEYGAC <u>GLLRKGGEKIGEKLKKIGQKIKNFFQKLVPQPEQ</u> | 6840.0 |
| 34 | HHHHHHAGGTGTEDSHPPYKQ <u>GLLRKGGEKIGEKLKKIGQKIKNFFQKLVPQPEQ</u> | 6269.3 |
| 35 | DTGEVPALQAAEIGA <u>GLLRKGGEKIGEKLKKIGQKIKNFFQKLVPQPEQ</u> | 5343.4 |
| 36 | YPTFGEHKQEKDLEYGAC <u>GLLRKGGEKIGEKLKKIGQKIKNFFQKLVPQPEQ</u> | 6017.2 |
| 37 | AGGTGTEDSHPPYKQ <u>GLLRKGGEKIGEKLKKIGQKIKNFFQKLVPQPEQ</u> | 5446.4 |

Antigenic peptide is indicated in bold, the AMP is underlined

Different forms of these peptides in combination with a terminal cysteine, GS-linker, His tag, mCRAMP and/or LL37 were developed. All peptides (Table 1) were synthesized using in vitro synthesis (Pepscan, Lelystad, The Netherlands).

The peptides were associated to OMVs via the LL37 (or mCRAMP) sequence. The ability of the peptides and the VP1 protein to induce neutralizing antibodies (in combination or absence of OMV) after two immunizations was evaluated in mice.

Murine Model

AC57BL/6 mice were immunized with the panel of Click-OMV vaccines. For each group, 10 mice were vaccinated two times with each of the constructed vaccines and a positive control group was immunized with inactivated EV71 virus. The vaccines (except positive control) were mixed in PBS and kept at 37° C. overnight. The next day (~18 h) all the mice were immunized. This immunization was repeated after 4 weeks. Two weeks after the second immunization the mice were sacrificed and sera was collected from all the mice. See table 2 for the vaccination scheme and experimental setup.

TABLE 2

Animal groups used in the vaccination scheme.

| Vaccine | Number of mice | Day 0 | Day 28 | Day 42 |
|---|---|---|---|---|
| PBS (formulation buffer) | 5 | 0.2 ml s.c. right | 0.2 ml s.c. right | Sacrificed |
| OMV [25 µg] | 5 | 0.2 ml s.c. right | 0.2 ml s.c. right | Sacrificed |
| Inactivated EV71 [7 ng] (positive control) | 10 | 0.2 ml s.c. right | 0.2 ml s.c. right | Sacrificed |
| EV71: 3 linear peptides [5.4 µg] | 10 | 0.2 ml s.c. right | 0.2 ml s.c. right | Sacrificed |
| EV71: 3 linear peptides [5.4 µg] + OMV [25 µg] | 10 | 0.2 ml s.c. right | 0.2 ml s.c. right | Sacrificed |
| OMV-EV71 peptides coupled with mCRAMP [25 µg OMV – 5.4 µg peptide pool] | 10 | 0.2 ml s.c. right | 0.2 ml s.c. right | Sacrificed |
| EV71 VP1 protein [5 µg] + OMV [25 µg] | 10 | 0.2 ml s.c. right | 0.2 ml s.c. right | Sacrificed |
| EV71 VP1 mCRAMP protein [5 µg] – OMV [25 µg] (linked) | 10 | 0.2 ml s.c. right | 0.2 ml s.c. right | Sacrificed |
| EV71 VP1 mCRAMP protein [5 µg] – OMV [5 µg] (linked) | 10 | 0.2 ml s.c. right | 0.2 ml s.c. right | Sacrificed |
| EV71 VP1 mCRAMP protein [5 µg] – OMV [1 µg] (linked) | 10 | 0.2 ml s.c. right | 0.2 ml s.c. right | Sacrificed |
| EV71 protein [5 µg] and OMV [25 µg], injected separately. | 10 | 0.1 ml OMV en 0.1 ml protein s.c. right | 0.1 ml OMV en 0.1 ml protein s.c. right | Sacrificed |

Results

Levels of Antibody Against EV71 VP1 Protein

To determine whether the immunized mice produced antibodies against the antigen, an initial ELISA was performed on pooled sera against the EV71 VP1 protein and OMVs present in the vaccines. High IgG titers were detected against OMVs only in the groups that had been immunized with OMVs (data not shown). Antibodies against EV71 VP1 protein could also be detected (data not shown). The ELISA with EV71 VP1 protein coating was repeated with individual mice sera (FIG. 3). The total IgG responses against EV71 VP1 protein showed that the negative groups (PBS and OMV) did not produce IgG antibodies towards EV71. The positive group (inactivated EV71) clearly induced IgG antibodies. Linking the protein to OMVs by the presence of mCRAMP showed an increase in VP1 specific antibody production compared to the unlinked protein-OMV mixture. This increase was reduced when mice were immunized with lower amounts of OMVs linked to protein ratios.

The levels of specific IgG subclasses, IgG1 and IgG2A, against VP1 were determined in an ELISA for more insight on the type of immune response elicited. Typically a shift in IgG2A to IgG1 ratio represents a shift towards a more Th1-like response. For most of the groups, there was no shift in the antibody titers of the subclasses except for the mice immunized with VP1 protein linked to OMVs by mCRAMP. In these groups we observed an increased IgG2A:IgG1 ratio (FIG. 4A+B) ratio.

34

Levels of Antibody Against EV71 Virus (C4 Genotype)

An ELISA was done in which the ELISA plates were coated with complete EV71 virus to determine the amount of virus specific antibodies in the sera. From the results depicted in FIG. 5 it is confirmed that antibodies are produced against the virus and the same overall pattern of antibody responses was found. The highest titers were induced by the VP1 mCRAMP protein-OMV vaccines. Thus increased antibody responses can be induced in mice against EV71 virus by protein or peptide Click-OMV vaccines.

Conclusions

Peptides or proteins attached to OMVs increase antibody responses in mice.

VP1 (EV71) protein attached to OMVs through mCRAMP induces skewing towards a Th1 response.

This animal study thus demonstrates that coupling EV71 antigens to an OMV platform increases the antibody responses against the EV71 antigen and virus. VP1 protein linked through the antimicrobial peptide mCRAMP increased the production of antibodies against VP1 protein and live virus compared to unbound VP1-OMV vaccine.

Example 3

The inventors investigated whether the immunogenicity of Prn could be enhanced by attaching them to OMVs via a linker peptide. Mice were immunized twice with the antigen alone, antigen mixed with OMVs, or antigen coupled to the OMVs. Subsequently, antibody levels against the antigen was measured in serum. For Prn coupled to *N. meningitidis* OMVs two different coupling-peptides were used, the murine mCRAMP and the human LL-37 peptide.

Materials and Methods

Administration of Study Substances

The vaccine was administered to the mice via s.c. injection into the inguinal area (total volume 200 µL). Both vaccinations were given on the right hand side, using a needle and syringe.

Blood Sampling

On day 42, during euthanasia, blood was collected via the retinal artery in individually labelled tubes. Blood samples were left at room temperature for at least 30 min (but no longer than 24 hours) and subsequently centrifuged in an Eppendorf centrifuge at 3500 rpm at room temperature or 15 min in SL 40R centrifuge at 3000 rpm at room temper, depending on the size of the tubes. The serum was transferred to individually labelled tubes and stored below –20° C. until analysis.

Analysis of Anti-Prn Antibody Titers Serum levels of anti-Prn antibodies were measured using a multiplex flow-cytometric immunoassay.

Statistical Analysis of Results

Tests for statistical significance between groups were performed on the anti-Prn antibody titers. To detect possible differences between groups, the experimental groups were compared to the placebo treated group using a Kruskal-Wallis test and Dunn's test to determine significant differences between the means. To detect possible differences between the groups treated with OMVs mixed with antigen and treated with OMVs coupled to antigen a Mann Whitney U test was used and the resulting p-values were corrected for multiple testing using the Benjamini-Hochberg method. No statistical analysis was performed on the FACS data. All results were considered significant when p<0.05.

Results

Anti-Prn Titers in Serum

Administration of the Prn protein without OMVs did not result in the induction of anti-Prn IgG (FIG. 6). When Prn protein was administered either mixed with OMVs or coupled to OMVs via mCRAMP, anti-Prn IgG levels increased significantly, indicating that the coupling method does not affect the immunogenicity of the antigen.

Conclusions

Mice were immunized with a *B. pertussis* antigen either alone, mixed with OMVs or coupled to the OMVs. Administration of Prn protein together with OMVs already induced the production of anti-Prn IgG. Coupling of Prn to the OMVs via mCRAMP did not result in an additional increase in anti-Prn antibody levels, compared to Prn mixed with OMVs. This indicates that addition of *N. meningitidis* OMVs to Prn by itself already increases immunogenicity of Prn. It also shows that the coupling method does not negatively interfere with the immunogenicity of the antigen.

Example 4

As an antigen, the SARS-CoV-2 spike protein in a pre-fusion state with 6 proline substitutions was used, which is based on the HexaPro spike protein from the paper by Hsieh et al (2020). An mCRAMP sequence was added at the C-terminus. The mCRAMP sequence enables the spontaneous association of the spike protein to the OMVs once mixed together. We have tested the immunogenicity of this SARS-CoV-2 vaccine concept in a mouse model after administration via the intranasal route, and for comparison also the intramuscular route. The mouse model provides for a good read-out on immunogenicity of these OMV vaccines. For measuring protection, a Syrian hamster model was used. Different animal models to study SARS-CoV-2 infection have been tested previously, including Syrian hamsters. Results from SARS-CoV-2 model development studies were used to define the challenge infection protocol in the current study with regards to challenge route, dose and follow up after challenge and defined the choice of the Syrian hamster model to establish efficacy of our novel SARS-CoV-2 vaccine candidate. Again, both the intranasal and intramuscular routes were compared.

Methods (Mouse Study)

Immunisation

BALB/c mice were immunised on day 0 and 21 via the intranasal (i.n.) or intramuscular (i.m.) route. On day 0, 21 and 35, blood was collected for assessment of induction of SARS-CoV-2 specific neutralising antibodies. Groups consisted of 10 mice each.

The following groups were included:
1. Tris sucrose i.n.
2. OMV i.n.
3. Spike i.n.
4. Spike mCRAMP i.n.
5. OMV+Spike i.n.
6. OMV+Spike mCRAMP i.n.
7. Tris sucrose i.m.
8. Spike i.m.
9. Spike mCRAMP i.m.
10. OMV+Spike i.m.
11. OMV+Spike mCRAMP i.m.

For intranasal immunization, a 20 µl inoculum was divided over both nostrils using a pipet. For intramuscular immunization, a 50 µl inoculum was injected into the outer thigh.

The OMV dose used was 15 µg protein per immunisation. The Spike and Spike mCRAMP dose used was also 15 µg protein per immunisation OMVs were isolated by EDTA extraction as described by van de Waterbeemd et al (2013). Spike protein was expressed in ExpiCHO-S cells and purified with a Twin-Strep column.

Serological Analysis

The virus neutralisation (VN) assay was performed on samples collected during the study as follows. In short, samples are heat inactivated for 30 minutes at 56 degrees. Subsequently, serial two-fold dilutions of the samples are made in infection medium in triplicate in 96-wells plates starting with a dilution of 1:5. The sample dilutions are then incubated with a fixed amount of virus (200 TCID50/well or 4000 TCID50/ml) for 1 hour at 37 degrees leading to a starting dilution of the serum in the assay of 1:10. Next, the virus-antibody mixtures are transferred to plates with Vero E6 cell culture monolayers, followed by an incubation period of 5-6 days at 37 degrees. Subsequently, plates are scored using the vitality marker WST8.

Results (Mouse Study)

Virus neutralisation titers were only detected in the groups receiving OMVs combined with either Spike or Spike-mCRAMP protein, with the latter group showing the highest titers and highest number of responders. No titers were detected in the groups receiving Spike or Spike-mCRAMP alone. The overall results were similar after i.n. and i.m. routes of immunization (FIG. 7).

Methods (Hamster Study)

Immunisation

Syrian hamsters were immunised on day 0 and 21 via the intranasal (i.n.) or intramuscular route (i.m). During the study, animals were weighed and blood was collected for assessment of induction of SARS-CoV-2 specific neutralising antibodies. Three weeks after the second immunisation (day 42), all animals were challenged intranasally with 10^4.0 TCID50 SARS-CoV-2, strain BetaCoV/Munich/BavPat1/2020.

The following groups were included:
1. Tris sucrose i.n.
2. OMV i.n.
3. Spike i.n.
4. Spike mCRAMP i.n.
5. OMV+Spike i.n.
6. OMV+Spike mCRAMP i.n.
7. Tris sucrose i.m.
8. OMV i.m.
9. Spike i.m.
10. Spike mCRAMP i.m.
11. OMV+Spike i.m.
12. OMV+Spike mCRAMP i.m.

On day 4 post challenge half of the animals per group were sacrificed by exsanguination under isoflurane anesthesia and necropsy was performed, with the remaining half of the animals following on day 7 post challenge.

Pathology

At the time of necropsy gross pathology was performed. All lung lobes were inspected, the percentage affected lung tissue estimated from the dorsal side, a gross pathological diagnosis described and the left lung lobe inflated with and preserved in 10% formalin. Trachea and nasal turbinates were macroscopically evaluated and sampled for virology and histopathology. Relative lung weight was calculated. Histopathological analysis from selected tissues was performed for all animals. After fixation with 10% formalin, sections from left lung and left nasal turbinate, and gastrointestinal tract tissue were embedded in paraffin and the tissue sections stained for histological examination. Histopathological assessment included aspects like congestion, emphysema, presence of foreign body, haemorrhage, bronchioloalveolar hyperplasia and inflammation and oedema. Quadruplicate 10-fold serial dilutions were used to determine the virus titers in confluent layers of Vero E6 cells. To this end, serial dilutions of the samples (throat swabs and tissue homogenates) were made and incubated on Vero E6 monolayers for 1 hour at 37 degrees. The monolayers were washed and incubated for 5 or 6 days at 37 degrees, and scored for CPE using the vitality marker WST8. Throat swabs and homogenised tissue samples were used to detect viral RNA by PCR. Virus neutralisation titers were determined as described above for the mouse sera.

Results (Hamster Study)

Virus neutralisation titers were mainly detected in the groups receiving OMVs combined with either Spike or Spike-mCRAMP protein. The group receiving OMV+Spike mCRAMP gave higher titers that OMV+Spike. No titers were detected in the groups receiving OMV or Spike alone, and only low titers in some mice in the Spike mCRAMP without OMV group. After challenge with SARS-CoV-2, almost no lung lesions were detected in the OMV+Spike and OMV+Spike mCRAMP groups. The overall results were similar after i.n. and i.m. routes of immunization (FIGS. 8 and 9).

Conclusions

In both the mouse and hamster model, virus-neutralising antibodies are induced when the Spike protein is combined with OMVs. In the hamster model, almost no lung lesions are found after challenge when vaccination was done with Spike protein combined with OMVs. Adding a C-terminal mCRAMP tag increases the protective response in both models. Overall these data show that (i) *Neisseria* OMVs are an effective adjuvant/delivery system for the Covid-19 Spike protein, and (ii) increasing OMV association by an mCRAMP tag improves the protective response.

REFERENCES

1. Fan Gao, Yi-Ping Wang, Qun-Ying Mao, Xin Yao, Shuang Liu, Feng-Xiang Li, Feng-Cai Zhu, Jing-Yu Yang, Zheng-Lun Liang, Feng-Min Lu and Jun-Zhi Wang. Enterovirus 71 viral capsid protein linear epitopes: Identification and characterization.
2. Damian Guang Wei Foo, Sylvie Alonso, Meng Chee Phoon, N. P. Ramachandran, Vincent Tak Kwong Chow, Chit Laa Poh. Identification of neutralizing linear epitopes from the VP1 capsid protein of Enterovirus 71 using synthetic peptides.
3. Chia-Chyi Liu, Ai-Hsiang Choua, Shu-Pei Liena, Hsiao-Yu Lina, Shih-Jen Liva,b, Jui-Yuan Changa, Meng-Shin Guoa, Yen-Hung Chowa, Wun-Syue Yanga, Kate Hsuen-Wen Changa, Charles Sia a, Pele Chonga,b. Identification and characterization of a cross-neutralization epitope of Enterovirus 71.
4. Kuan-Ying Arthur Huang, Mei-Feng Chen, Yhu-Chering Huang, Shin-Ru Shih, Cheng-Hsun Chiu, Jainn-Jim Lin, Jen-Ren Wang, Kuo-Chien Tsao & Tzou-Yien Lin. Epitope-associated and specificity-focused features of EV71-neutralizing antibody repertoires from plasmablasts of infected children.
5. Zhiqiang Ku, Xiaohua Ye, Jinping Shi, Xiaoli Wang, Qingwei Liu and Zhong Huang. Single Neutralizing Monoclonal Antibodies Targeting the VP1 GH Loop of Enterovirus 71 Inhibit both Virus Attachment and Internalization during Viral Entry.
6. Longfa Xu, Delei He, Zhiqun Li, Jun Zheng, Lisheng Yang, Miao Yu, Hai Yu, Yixin Chen, Yuqiong Que, James Wai Kuo Shih, Gang Liu, Jun Zhang, Qinjian Zhao, Tong Cheng, and Protection against Lethal Enterovirus 71 Challenge in Mice by a Recombinant Vaccine Candidate Containing a Broadly Cross-Neutralizing Epitope within the VP2 EF Loop. Ningshao Xia Theranostics 2014, 4, 498-513.
7. For more info on CLIPS, please refer to https://www.pepscan.com/custom-peptide-synthesis/clips-constrained-peptides
8. Wang T T, Tan G S, Hai R, Pica N, Ngai L, Ekiert D C, Wilson I A, Garcia-Sastre A, Moran T M, Palese P. Vaccination with a synthetic peptide from the influenza virus hemagglutinin provides protection against distinct viral subtypes. Proc Natl Acad Sci USA. 2010 Nov. 2; 107(44):18979-84. doi: 10.1073/pnas.1013387107. Epub 2010 Oct. 18.
9. van de Waterbeemd B, Zomer G, Kaaijk P, Ruiterkamp N, Wijffels R H, van den Dobbelsteen G P J M, Leo A. van der Pol, L A. Improved Production Process for Native Outer Membrane Vesicle Vaccine against *Neisseria meningitidis*. PLOS One Volume 8, Issue 5, e65157 (2013)
10. Ching-Lin Hsieh, Jory A. Goldsmith, Jeffrey M. Schaub, Andrea M. DiVenere, Hung-Che Kuo, Kamyab Javanmardi, Kevin C. Le, Daniel Wrapp, Alison G. Lee, Yutong Liu, Chia-Wei Chou, Patrick O. Byrne, Christy K. Hjorth, Nicole V. Johnson, John Ludes-Meyers, Annalee W. Nguyen, Juyeon Park, Nianshuang Wang, Dzifa Amengor, Jason J. Lavinder, Gregory C. Ippolito, Jennifer A. Maynard, Ilya J. Finkelstein, Jason S. McLellan. Structure-based design of prefusion-stabilized SARS-CoV-2 spikes. Science September 2020:Vol. 369, Issue 6510, pp. 1501-1505

---

The invention claimed is:

1. A complex of an Outer Membrane Vesicle (OMV), a vertebrate antimicrobial peptide (AMP) and an antigen, wherein the AMP is non-covalently complexed with the OMV and wherein the antigen is conjugated to the AMP, and wherein the AMP is a cathelicidin.

2. The complex according to claim 1, wherein the antigen is covalently linked to the AMP in a fusion protein comprising the antigen and the AMP in a single polypeptide chain.

3. The complex according to claim 1, wherein the antigen is an antigen that is associated with an infectious disease and/or a tumour.

4. The complex according to claim 1, wherein the OMV is not a detergent-extracted OMV.

5. The complex according to claim 1, wherein the OMV comprises at least partially detoxified LPS.

6. The complex according to claim 1, wherein the OMV is obtainable from a Gram-negative bacterium.

7. The complex according to claim 6, wherein the Gram-negative bacterium belongs to a genus selected from the group consisting of *Neisseria, Bordetella, Escherichia* and *Salmonella.*

8. A pharmaceutical composition comprising a complex according to claim 1 and a pharmaceutically accepted excipient.

9. A medicament comprising the complex according to claim 1.

10. A method of treatment comprising administering the complex according to claim 1 to induce or stimulate an immune response in a subject against the antigen.

11. The method according to claim 10, wherein the method comprises administering the complex intranasally or intramuscularly.

12. A method for producing a complex of an Outer Membrane Vesicle (OMV), a vertebrate antimicrobial peptide (AMP) and an antigen, wherein the AMP is non-covalently complexed with the OMV wherein the antigen is conjugated to the AMP, and wherein the AMP is a cathelicidin, wherein the method comprises the steps of:

i) culturing a population of Gram-negative bacteria as defined in claim 6 under conditions conducive for the production of OMV;

ii) recovering the OMV produced in i);

iii) contacting the OMV recovered in ii) with the AMP conjugated to the antigen, under conditions conducive to the formation of a non-covalent complex between the AMP and the OMV; and vi) optionally, recovery of the complex.

13. The complex according to claim 6, wherein the Gram-negative bacterium comprises at least one of:

a) a genetic modification causing the bacterium to produce an LPS with reduced toxicity; and b) a genetic modification that increases vesicle formation.

14. The complex according to claim 1, wherein the cathelicidin is a non-human cathelicidin.

15. The complex according to claim 1, wherein the cathelicidin is a mouse cathelicidin-related antimicrobial peptide (mCRAMP).

16. The method according to claim 12, wherein the cathelicidin is a non-human cathelicidin.

17. The method according to claim 12, wherein the cathelicidin is a mouse cathelicidin-related antimicrobial peptide (mCRAMP).

18. The complex according to claim 13, and wherein at least one of:

the genetic modification in a) reduces or eliminates expression of at least one of a lpxL1, lpxL2, lpxA, lpxD, and lpxK gene or a homologue thereof and/or increases the expression of at least one of a lpxP, lpxE, lpxF and pagL gene; and the genetic modification in b) reduces or eliminates expression of an ompA gene or a homologue thereof.

19. The complex according to claim 13, wherein the genetic modification in step b) reduces or eliminates expression of a rmpM gene or a homologue thereof.

* * * * *

SEQUENCE LISTING

<160> NUMBER OF SEQ ID NOS: 50

<210> SEQ ID NO 1
<211> LENGTH: 34
<212> TYPE: PRT
<213> ORGANISM: Mus musculus

<400> SEQUENCE: 1

```
Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 2
<211> LENGTH: 11
<212> TYPE: PRT
<213> ORGANISM: artificial sequence
<220> FEATURE:
<223> OTHER INFORMATION: linker

<400> SEQUENCE: 2

Ser Pro Lys Lys Lys Arg Lys Val Glu Ala Ser
1               5                   10

<210> SEQ ID NO 3
<211> LENGTH: 16
<212> TYPE: PRT
<213> ORGANISM: artificial sequence
<220> FEATURE:
<223> OTHER INFORMATION: linker

<400> SEQUENCE: 3

Ser Gly Ser Glu Thr Pro Gly Thr Ser Glu Ser Ala Thr Pro Glu Ser
1               5                   10                  15

<210> SEQ ID NO 4
<211> LENGTH: 17
<212> TYPE: PRT
<213> ORGANISM: artificial sequence
<220> FEATURE:
<223> OTHER INFORMATION: linker

<400> SEQUENCE: 4

Lys Ser Gly Ser Glu Thr Pro Gly Thr Ser Glu Ser Ala Thr Pro Glu
1               5                   10                  15

Ser

<210> SEQ ID NO 5
<211> LENGTH: 299
<212> TYPE: PRT
<213> ORGANISM: Neisseria meningitidis

<400> SEQUENCE: 5

Met Pro Ser Glu Lys Lys Met Cys Ile Glu Met Lys Phe Ile Phe Phe
1               5                   10                  15

Val Leu Tyr Val Leu Gln Phe Leu Pro Phe Ala Leu Leu His Lys Ile
            20                  25                  30

Ala Asp Leu Thr Gly Leu Leu Ala Tyr Leu Leu Val Lys Pro Arg Arg
        35                  40                  45

Arg Ile Gly Glu Ile Asn Leu Ala Lys Cys Phe Ser Glu Trp Ser Glu
    50                  55                  60

Glu Lys Arg Lys Thr Val Leu Lys Gln His Phe Lys His Met Ala Lys
65                  70                  75                  80

Leu Met Leu Glu Tyr Gly Leu Tyr Trp Tyr Ala Pro Ala Gly Arg Leu
                85                  90                  95

Lys Ser Leu Val Arg Tyr Arg Asn Lys His Tyr Leu Asp Asp Ala Leu
            100                 105                 110

Ala Ala Gly Glu Lys Val Ile Ile Leu Tyr Pro His Phe Thr Ala Phe
```

```
                115                    120                    125

Glu Met Ala Val Tyr Ala Leu Asn Gln Asp Ile Pro Leu Ile Ser Met
    130                    135                    140

Tyr Ser His Gln Lys Asn Lys Ile Leu Asp Glu Gln Ile Leu Lys Gly
145                    150                    155                    160

Arg Asn Arg Tyr His Asn Val Phe Leu Ile Gly Arg Thr Glu Gly Leu
                   165                    170                    175

Arg Ala Leu Val Lys Gln Phe Arg Lys Ser Ser Ala Pro Phe Leu Tyr
                   180                    185                    190

Leu Pro Asp Gln Asp Phe Gly Arg Asn Asp Ser Val Phe Val Asp Phe
                   195                    200                    205

Phe Gly Ile Gln Thr Ala Thr Ile Thr Gly Leu Ser Arg Ile Ala Ala
                   210                    215                    220

Leu Ala Asn Ala Lys Val Ile Pro Ala Ile Pro Val Arg Glu Ala Asp
225                    230                    235                    240

Asn Thr Val Thr Leu His Phe Tyr Pro Ala Trp Lys Ser Phe Pro Gly
                   245                    250                    255

Glu Asp Ala Lys Ala Asp Ala Gln Arg Met Asn Arg Phe Ile Glu Asp
                   260                    265                    270

Arg Val Arg Glu His Pro Glu Gln Tyr Phe Trp Leu His Lys Arg Phe
                   275                    280                    285

Lys Thr Arg Pro Glu Gly Ser Pro Asp Phe Tyr
    290                    295

<210> SEQ ID NO 6
<211> LENGTH: 306
<212> TYPE: PRT
<213> ORGANISM: Escherichia coli

<400> SEQUENCE: 6

Met Phe Pro Gln Cys Lys Phe Ser Arg Glu Phe Leu His Pro Arg Tyr
1               5                   10                   15

Trp Leu Thr Trp Phe Gly Leu Gly Val Leu Trp Leu Trp Val Gln Leu
               20                   25                   30

Pro Tyr Pro Val Leu Cys Phe Leu Gly Thr Arg Ile Gly Ala Met Ala
           35                   40                   45

Arg Pro Phe Leu Lys Arg Arg Glu Ser Ile Ala Arg Lys Asn Leu Glu
    50                   55                   60

Leu Cys Phe Pro Gln His Ser Ala Glu Glu Arg Glu Lys Met Ile Ala
65                   70                   75                   80

Glu Asn Phe Arg Ser Leu Gly Met Ala Leu Val Glu Thr Gly Met Ala
               85                   90                   95

Trp Phe Trp Pro Asp Ser Arg Val Arg Lys Trp Phe Asp Val Glu Gly
           100                  105                  110

Leu Asp Asn Leu Lys Arg Ala Gln Met Gln Asn Arg Gly Val Met Val
           115                  120                  125

Val Gly Val His Phe Met Ser Leu Glu Leu Gly Gly Arg Val Met Gly
    130                  135                  140

Leu Cys Gln Pro Met Met Ala Thr Tyr Arg Pro His Asn Asn Gln Leu
145                  150                  155                  160

Met Glu Trp Val Gln Thr Arg Gly Arg Met Arg Ser Asn Lys Ala Met
               165                  170                  175

Ile Gly Arg Asn Asn Leu Arg Gly Ile Val Gly Ala Leu Lys Lys Gly
           180                  185                  190
```

-continued

```
Glu Ala Val Trp Phe Ala Pro Asp Gln Asp Tyr Gly Arg Lys Gly Ser
        195                 200                 205

Ser Phe Ala Pro Phe Phe Ala Val Glu Asn Val Ala Thr Thr Asn Gly
    210                 215                 220

Thr Tyr Val Leu Ser Arg Leu Ser Gly Ala Ala Met Leu Thr Val Thr
225                 230                 235                 240

Met Val Arg Lys Ala Asp Tyr Ser Gly Tyr Arg Leu Phe Ile Thr Pro
                245                 250                 255

Glu Met Glu Gly Tyr Pro Thr Asp Glu Asn Gln Ala Ala Ala Tyr Met
                260                 265                 270

Asn Lys Ile Ile Glu Lys Glu Ile Met Arg Ala Pro Glu Gln Tyr Leu
            275                 280                 285

Trp Ile His Arg Arg Phe Lys Thr Arg Pro Val Gly Glu Ser Ser Leu
    290                 295                 300

Tyr Ile
305

<210> SEQ ID NO 7
<211> LENGTH: 258
<212> TYPE: PRT
<213> ORGANISM: Pseudomonas aeruginosa

<400> SEQUENCE: 7

Met Ser Leu Ile Asp Pro Arg Ala Ile Ile Asp Pro Ser Ala Arg Leu
1               5                   10                  15

Ala Ala Asp Val Gln Val Gly Pro Trp Ser Ile Val Gly Ala Glu Val
            20                  25                  30

Glu Ile Gly Glu Gly Thr Val Ile Gly Pro His Val Val Leu Lys Gly
        35                  40                  45

Pro Thr Lys Ile Gly Lys His Asn Arg Ile Tyr Gln Phe Ser Ser Val
    50                  55                  60

Gly Glu Asp Thr Pro Asp Leu Lys Tyr Lys Gly Glu Pro Thr Arg Leu
65                  70                  75                  80

Val Ile Gly Asp His Asn Val Ile Arg Glu Gly Val Thr Ile His Arg
                85                  90                  95

Gly Thr Val Gln Asp Arg Ala Glu Thr Thr Ile Gly Asp His Asn Leu
            100                 105                 110

Ile Met Ala Tyr Ala His Ile Gly His Asp Ser Val Ile Gly Asn His
        115                 120                 125

Cys Ile Leu Val Asn Asn Thr Ala Leu Ala Gly His Val His Val Asp
    130                 135                 140

Asp Trp Ala Ile Leu Ser Gly Tyr Thr Leu Val His Gln Tyr Cys Arg
145                 150                 155                 160

Ile Gly Ala His Ser Phe Ser Gly Met Gly Ser Ala Ile Gly Lys Asp
                165                 170                 175

Val Pro Ala Tyr Val Thr Val Phe Gly Asn Pro Ala Glu Ala Arg Ser
            180                 185                 190

Met Asn Phe Glu Gly Met Arg Arg Arg Gly Phe Ser Ser Glu Ala Ile
        195                 200                 205

His Ala Leu Arg Arg Ala Tyr Lys Val Val Tyr Arg Gln Gly His Thr
    210                 215                 220

Val Glu Glu Ala Leu Ala Glu Leu Ala Glu Ser Ala Ala Gln Phe Pro
225                 230                 235                 240

Glu Val Ala Val Phe Arg Asp Ser Ile Gln Ser Ala Thr Arg Gly Ile
                245                 250                 255
```

Thr Arg

<210> SEQ ID NO 8
<211> LENGTH: 353
<212> TYPE: PRT
<213> ORGANISM: Pseudomonas aeruginosa

<400> SEQUENCE: 8

```
Met Met Ser Thr Leu Ser Tyr Thr Leu Gly Gln Leu Ala Ala His Val
1               5                   10                  15

Gly Ala Glu Val Arg Gly Asp Ala Asp Leu Pro Ile Gln Gly Leu Ala
                20                  25                  30

Thr Leu Gln Glu Ala Gly Pro Ala Gln Leu Ser Phe Leu Ala Asn Pro
            35                  40                  45

Gln Tyr Arg Lys Tyr Leu Pro Glu Ser Arg Ala Gly Ala Val Leu Leu
        50                  55                  60

Thr Ala Ala Asp Ala Asp Gly Phe Ala Gly Thr Ala Leu Val Val Ala
65                  70                  75                  80

Asn Pro Tyr Leu Ala Tyr Ala Ser Leu Ser His Leu Phe Asp Arg Lys
                85                  90                  95

Pro Lys Ala Ala Ala Gly Ile His Pro Thr Ala Ile Val Ala Ala Asp
            100                 105                 110

Ala Glu Val Asp Pro Ser Ala Ser Val Gly Ala Tyr Ala Val Ile Glu
        115                 120                 125

Ser Gly Ala Arg Ile Gly Ala Gly Val Ser Ile Gly Ala His Cys Val
    130                 135                 140

Ile Gly Ala Arg Ser Val Ile Gly Glu Gly Gly Trp Leu Ala Pro Arg
145                 150                 155                 160

Val Thr Leu Tyr His Asp Val Thr Ile Gly Ala Arg Val Ser Ile Gln
                165                 170                 175

Ser Gly Ala Val Ile Gly Gly Glu Gly Phe Gly Phe Ala Asn Glu Lys
            180                 185                 190

Gly Val Trp Gln Lys Ile Ala Gln Ile Gly Gly Val Thr Ile Gly Asp
        195                 200                 205

Asp Val Glu Ile Gly Ala Asn Thr Thr Ile Asp Arg Gly Ala Leu Ser
    210                 215                 220

Asp Thr Leu Ile Gly Asn Gly Val Lys Leu Asp Asn Gln Ile Met Ile
225                 230                 235                 240

Ala His Asn Val Gln Ile Gly Asp His Thr Ala Met Ala Ala Cys Val
                245                 250                 255

Gly Ile Ser Gly Ser Ala Lys Ile Gly Arg His Cys Met Leu Ala Gly
            260                 265                 270

Gly Val Gly Leu Val Gly His Ile Glu Ile Cys Asp Asn Val Phe Val
        275                 280                 285

Thr Gly Met Thr Met Val Thr Arg Ser Ile Thr Glu Pro Gly Ser Tyr
    290                 295                 300

Ser Ser Gly Thr Ala Met Gln Pro Ala Ala Glu Trp Lys Lys Ser Ala
305                 310                 315                 320

Ala Arg Ile Arg Gln Leu Asp Asp Met Ala Arg Arg Leu Gln Gln Leu
                325                 330                 335

Glu Lys Arg Leu Ala Ala Val Thr Ser Ser Gly Asp Ala Ser Ser Asp
            340                 345                 350

Ala
```

```
<210> SEQ ID NO 9
<211> LENGTH: 242
<212> TYPE: PRT
<213> ORGANISM: Neisseria meningitidis

<400> SEQUENCE: 9

Met Thr Lys Gln Leu Lys Leu Ser Ala Leu Phe Val Ala Leu Leu Ala
1               5                   10                  15

Ser Gly Thr Ala Val Ala Gly Glu Ala Ser Val Gln Gly Tyr Thr Val
            20                  25                  30

Ser Gly Gln Ser Asn Glu Ile Val Arg Asn Asn Tyr Gly Glu Cys Trp
        35                  40                  45

Lys Asn Ala Tyr Phe Asp Lys Ala Ser Gln Gly Arg Val Glu Cys Gly
    50                  55                  60

Asp Ala Val Ala Ala Pro Glu Pro Glu Pro Glu Pro Ala Pro
65                  70                  75                  80

Ala Pro Val Val Val Val Glu Gln Ala Pro Gln Tyr Val Asp Glu Thr
            85                  90                  95

Ile Ser Leu Ser Ala Lys Thr Leu Phe Gly Phe Asp Lys Asp Ser Leu
            100                 105                 110

Arg Ala Glu Ala Gln Asp Asn Leu Lys Val Leu Ala Gln Arg Leu Ser
        115                 120                 125

Arg Thr Asn Val Gln Ser Val Arg Val Glu Gly His Thr Asp Phe Met
    130                 135                 140

Gly Ser Asp Lys Tyr Asn Gln Ala Leu Ser Glu Arg Arg Ala Tyr Val
145                 150                 155                 160

Val Ala Asn Asn Leu Val Ser Asn Gly Val Pro Val Ser Arg Ile Ser
            165                 170                 175

Ala Val Gly Leu Gly Glu Ser Gln Ala Gln Met Thr Gln Val Cys Glu
            180                 185                 190

Ala Glu Val Ala Lys Leu Gly Ala Lys Val Ser Lys Ala Lys Lys Arg
        195                 200                 205

Glu Ala Leu Ile Ala Cys Ile Glu Pro Asp Arg Arg Val Asp Val Lys
    210                 215                 220

Ile Arg Ser Ile Val Thr Arg Gln Val Val Pro Ala His Asn His His
225                 230                 235                 240

Gln His

<210> SEQ ID NO 10
<211> LENGTH: 5
<212> TYPE: PRT
<213> ORGANISM: artificial sequence
<220> FEATURE:
<223> OTHER INFORMATION: linker

<400> SEQUENCE: 10

Gly Gly Gly Gly Ser
1               5

<210> SEQ ID NO 11
<211> LENGTH: 5
<212> TYPE: PRT
<213> ORGANISM: artificial sequence
<220> FEATURE:
<223> OTHER INFORMATION: linker

<400> SEQUENCE: 11

Glu Ala Ala Ala Lys
```

```
1               5

<210> SEQ ID NO 12
<211> LENGTH: 12
<212> TYPE: PRT
<213> ORGANISM: artificial sequence
<220> FEATURE:
<223> OTHER INFORMATION: linker

<400> SEQUENCE: 12

Gly Gly Gly Ser Gly Gly Gly Ser Gly Gly Gly Ser
1               5                   10

<210> SEQ ID NO 13
<211> LENGTH: 37
<212> TYPE: PRT
<213> ORGANISM: Homo sapiens

<400> SEQUENCE: 13

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 14
<211> LENGTH: 297
<212> TYPE: PRT
<213> ORGANISM: Enterovirus 71

<400> SEQUENCE: 14

Gly Asp Arg Val Ala Asp Val Ile Glu Ser Ser Ile Gly Asp Ser Val
1               5                   10                  15

Ser Arg Ala Leu Thr His Ala Leu Pro Ala Pro Thr Gly Gln Asn Thr
            20                  25                  30

Gln Val Ser Ser His Arg Leu Asp Thr Gly Arg Val Pro Ala Leu Gln
        35                  40                  45

Ala Ala Glu Ile Gly Ala Ser Ser Asn Ala Ser Asp Glu Ser Met Ile
    50                  55                  60

Glu Thr Arg Cys Val Leu Asn Ser His Ser Thr Ala Glu Thr Thr Leu
65                  70                  75                  80

Asp Ser Phe Phe Ser Arg Ala Gly Leu Val Gly Glu Ile Asp Leu Pro
                85                  90                  95

Leu Glu Gly Thr Thr Asn Pro Asn Gly Tyr Ala Asn Trp Asp Ile Asp
            100                 105                 110

Ile Thr Gly Tyr Ala Gln Met Arg Arg Lys Val Glu Leu Phe Thr Tyr
        115                 120                 125

Met Arg Phe Asp Ala Glu Phe Thr Phe Val Ala Cys Thr Pro Thr Gly
    130                 135                 140

Glu Val Val Pro Gln Leu Leu Gln Tyr Met Phe Val Pro Pro Gly Ala
145                 150                 155                 160

Pro Lys Pro Asp Ser Arg Glu Ser Leu Ala Trp Gln Thr Ala Thr Asn
                165                 170                 175

Pro Ser Val Phe Val Lys Leu Ser Asp Pro Pro Ala Gln Val Ser Val
            180                 185                 190

Pro Phe Met Ser Pro Ala Ser Ala Tyr Gln Trp Phe Tyr Asp Gly Tyr
        195                 200                 205
```

```
Pro Thr Phe Gly Glu His Lys Gln Glu Lys Asp Leu Glu Tyr Gly Ala
    210                 215                 220

Cys Pro Asn Asn Met Met Gly Thr Phe Ser Val Arg Thr Val Gly Thr
225                 230                 235                 240

Ser Lys Ser Lys Tyr Pro Leu Val Val Arg Ile Tyr Met Arg Met Lys
                245                 250                 255

His Val Arg Ala Trp Ile Pro Arg Pro Met Arg Asn Gln Asn Tyr Leu
                260                 265                 270

Phe Lys Ala Asn Pro Asn Tyr Ala Gly Asn Ser Ile Lys Pro Thr Gly
                275                 280                 285

Ala Ser Arg Thr Ala Ile Thr Thr Leu
    290                 295
```

```
<210> SEQ ID NO 15
<211> LENGTH: 18
<212> TYPE: PRT
<213> ORGANISM: artificial sequence
<220> FEATURE:
<223> OTHER INFORMATION: EV71 VP fragment

<400> SEQUENCE: 15

Tyr Pro Thr Phe Gly Glu His Lys Gln Glu Lys Asp Leu Glu Tyr Gly
1               5                   10                  15

Ala Cys
```

```
<210> SEQ ID NO 16
<211> LENGTH: 15
<212> TYPE: PRT
<213> ORGANISM: artificial sequence
<220> FEATURE:
<223> OTHER INFORMATION: EV71 VP fragment

<400> SEQUENCE: 16

Asp Thr Gly Glu Val Pro Ala Leu Gln Ala Ala Glu Ile Gly Ala
1               5                   10                  15
```

```
<210> SEQ ID NO 17
<211> LENGTH: 15
<212> TYPE: PRT
<213> ORGANISM: artificial sequence
<220> FEATURE:
<223> OTHER INFORMATION: EV71 VP fragment

<400> SEQUENCE: 17

Ala Gly Gly Thr Gly Thr Glu Asp Ser His Pro Pro Tyr Lys Gln
1               5                   10                  15
```

```
<210> SEQ ID NO 18
<211> LENGTH: 539
<212> TYPE: PRT
<213> ORGANISM: Bordetella pertussis

<400> SEQUENCE: 18

Asp Trp Asn Asn Gln Ser Ile Val Lys Thr Gly Glu Arg Gln His Gly
1               5                   10                  15

Ile His Ile Gln Gly Ser Asp Pro Gly Gly Val Arg Thr Ala Ser Gly
                20                  25                  30

Thr Thr Ile Lys Val Ser Gly Arg Gln Ala Gln Gly Ile Leu Leu Glu
        35                  40                  45

Asn Pro Ala Ala Glu Leu Gln Phe Arg Asn Gly Ser Val Thr Ser Ser
    50                  55                  60
```

-continued

```
Gly Gln Leu Ser Asp Asp Gly Ile Arg Arg Phe Leu Gly Thr Val Thr
65                  70                  75                  80

Val Lys Ala Gly Lys Leu Val Ala Asp His Ala Thr Leu Ala Asn Val
                85                  90                  95

Gly Asp Thr Trp Asp Asp Asp Gly Ile Ala Leu Tyr Val Ala Gly Glu
            100                 105                 110

Gln Ala Gln Ala Ser Ile Ala Asp Ser Thr Leu Gln Gly Ala Gly Gly
        115                 120                 125

Val Gln Ile Glu Arg Gly Ala Asn Val Thr Val Gln Arg Ser Ala Ile
        130                 135                 140

Val Asp Gly Gly Leu His Ile Gly Ala Leu Gln Ser Leu Gln Pro Glu
145                 150                 155                 160

Asp Leu Pro Pro Ser Arg Val Val Leu Arg Asp Thr Asn Val Thr Ala
                165                 170                 175

Val Pro Ala Ser Gly Ala Pro Ala Ala Val Ser Val Leu Gly Ala Ser
            180                 185                 190

Glu Leu Thr Leu Asp Gly Gly His Ile Thr Gly Gly Arg Ala Ala Gly
        195                 200                 205

Val Ala Ala Met Gln Gly Ala Val Val His Leu Gln Arg Ala Thr Ile
        210                 215                 220

Arg Arg Gly Asp Ala Pro Ala Gly Gly Ala Val Pro Gly Gly Ala Val
225                 230                 235                 240

Pro Gly Gly Ala Val Pro Gly Gly Phe Gly Pro Gly Gly Phe Gly Pro
            245                 250                 255

Val Leu Asp Gly Trp Tyr Gly Val Asp Val Ser Gly Ser Ser Val Glu
        260                 265                 270

Leu Ala Gln Ser Ile Val Glu Ala Pro Glu Leu Gly Ala Ala Ile Arg
        275                 280                 285

Val Gly Arg Gly Ala Arg Val Thr Val Ser Gly Gly Ser Leu Ser Ala
        290                 295                 300

Pro His Gly Asn Val Ile Glu Thr Gly Gly Ala Arg Arg Phe Ala Pro
305                 310                 315                 320

Gln Ala Ala Pro Leu Ser Ile Thr Leu Gln Ala Gly Ala His Ala Gln
            325                 330                 335

Gly Lys Ala Leu Leu Tyr Arg Val Leu Pro Glu Pro Val Lys Leu Thr
        340                 345                 350

Leu Thr Gly Gly Ala Asp Ala Gln Gly Asp Ile Val Ala Thr Glu Leu
        355                 360                 365

Pro Ser Ile Pro Gly Thr Ser Ile Gly Pro Leu Asp Val Ala Leu Ala
        370                 375                 380

Ser Gln Ala Arg Trp Thr Gly Ala Thr Arg Ala Val Asp Ser Leu Ser
385                 390                 395                 400

Ile Asp Asn Ala Thr Trp Val Met Thr Asp Asn Ser Asn Val Gly Ala
            405                 410                 415

Leu Arg Leu Ala Ser Asp Gly Ser Val Asp Phe Gln Gln Pro Ala Glu
        420                 425                 430

Ala Gly Arg Phe Lys Val Leu Thr Val Asn Thr Leu Ala Gly Ser Gly
        435                 440                 445

Leu Phe Arg Met Asn Val Phe Ala Asp Leu Gly Leu Ser Asp Lys Leu
        450                 455                 460

Val Val Met Gln Asp Ala Ser Gly Gln His Arg Leu Trp Val Arg Asn
465                 470                 475                 480

Ser Gly Ser Glu Pro Ala Ser Ala Asn Thr Leu Leu Leu Val Gln Thr
```

```
                385            490             495

Pro Leu Gly Ser Ala Ala Thr Phe Thr Leu Ala Asn Lys Asp Gly Lys
            500             505             510

Val Asp Ile Gly Thr Tyr Arg Tyr Arg Leu Ala Ala Asn Gly Asn Gly
            515             520             525

Gln Trp Ser Leu Val Gly Ala Lys Ala Pro Pro
    530             535

<210> SEQ ID NO 19
<211> LENGTH: 577
<212> TYPE: PRT
<213> ORGANISM: artificial sequence
<220> FEATURE:
<223> OTHER INFORMATION: p69-His

<400> SEQUENCE: 19

Met His His His His His His Gly Gly Gly Ser Gly Gly Gly Ser Gly
1               5               10              15

Gly Gly Ser Glu Asn Leu Tyr Phe Gln Gly Asp Trp Asn Asn Gln Ser
            20              25              30

Ile Val Lys Thr Gly Glu Arg Gln His Gly Ile His Ile Gln Gly Ser
            35              40              45

Asp Pro Gly Gly Val Arg Thr Ala Ser Gly Thr Thr Ile Lys Val Ser
    50              55              60

Gly Arg Gln Ala Gln Gly Ile Leu Leu Glu Asn Pro Ala Ala Glu Leu
65              70              75              80

Gln Phe Arg Asn Gly Ser Val Thr Ser Ser Gly Gln Leu Ser Asp Asp
            85              90              95

Gly Ile Arg Arg Phe Leu Gly Thr Val Thr Val Lys Ala Gly Lys Leu
            100             105             110

Val Ala Asp His Ala Thr Leu Ala Asn Val Gly Asp Thr Trp Asp Asp
            115             120             125

Asp Gly Ile Ala Leu Tyr Val Ala Gly Glu Gln Ala Gln Ala Ser Ile
    130             135             140

Ala Asp Ser Thr Leu Gln Gly Ala Gly Gly Val Gln Ile Glu Arg Gly
145             150             155             160

Ala Asn Val Thr Val Gln Arg Ser Ala Ile Val Asp Gly Gly Leu His
            165             170             175

Ile Gly Ala Leu Gln Ser Leu Gln Pro Glu Asp Leu Pro Pro Ser Arg
            180             185             190

Val Val Leu Arg Asp Thr Asn Val Thr Ala Val Pro Ala Ser Gly Ala
            195             200             205

Pro Ala Ala Val Ser Val Leu Gly Ala Ser Glu Leu Thr Leu Asp Gly
    210             215             220

Gly His Ile Thr Gly Gly Arg Ala Ala Gly Val Ala Ala Met Gln Gly
225             230             235             240

Ala Val Val His Leu Gln Arg Ala Thr Ile Arg Arg Gly Asp Ala Pro
            245             250             255

Ala Gly Gly Ala Val Pro Gly Gly Ala Val Pro Gly Gly Ala Val Pro
            260             265             270

Gly Gly Phe Gly Pro Gly Gly Phe Gly Pro Val Leu Asp Gly Trp Tyr
            275             280             285

Gly Val Asp Val Ser Gly Ser Ser Val Glu Leu Ala Gln Ser Ile Val
    290             295             300

Glu Ala Pro Glu Leu Gly Ala Ala Ile Arg Val Gly Arg Gly Ala Arg
```

-continued

```
305             310             315             320

Val Thr Val Ser Gly Gly Ser Leu Ser Ala Pro His Gly Asn Val Ile
                325             330             335

Glu Thr Gly Gly Ala Arg Arg Phe Ala Pro Gln Ala Ala Pro Leu Ser
            340             345             350

Ile Thr Leu Gln Ala Gly Ala His Ala Gln Gly Lys Ala Leu Leu Tyr
        355             360             365

Arg Val Leu Pro Glu Pro Val Lys Leu Thr Leu Thr Gly Gly Ala Asp
        370             375             380

Ala Gln Gly Asp Ile Val Ala Thr Glu Leu Pro Ser Ile Pro Gly Thr
385             390             395             400

Ser Ile Gly Pro Leu Asp Val Ala Leu Ala Ser Gln Ala Arg Trp Thr
            405             410             415

Gly Ala Thr Arg Ala Val Asp Ser Leu Ser Ile Asp Asn Ala Thr Trp
        420             425             430

Val Met Thr Asp Asn Ser Asn Val Gly Ala Leu Arg Leu Ala Ser Asp
        435             440             445

Gly Ser Val Asp Phe Gln Gln Pro Ala Glu Ala Gly Arg Phe Lys Val
    450             455             460

Leu Thr Val Asn Thr Leu Ala Gly Ser Gly Leu Phe Arg Met Asn Val
465             470             475             480

Phe Ala Asp Leu Gly Leu Ser Asp Lys Leu Val Val Met Gln Asp Ala
            485             490             495

Ser Gly Gln His Arg Leu Trp Val Arg Asn Ser Gly Ser Glu Pro Ala
        500             505             510

Ser Ala Asn Thr Leu Leu Leu Val Gln Thr Pro Leu Gly Ser Ala Ala
        515             520             525

Thr Phe Thr Leu Ala Asn Lys Asp Gly Lys Val Asp Ile Gly Thr Tyr
    530             535             540

Arg Tyr Arg Leu Ala Ala Asn Gly Asn Gly Gln Trp Ser Leu Val Gly
545             550             555             560

Ala Lys Ala Pro Pro Gly Gly Gly Ser Gly Gly Gly Ser Gly Gly Gly
            565             570             575

Ser
```

<210> SEQ ID NO 20
<211> LENGTH: 611
<212> TYPE: PRT
<213> ORGANISM: artificial sequence
<220> FEATURE:
<223> OTHER INFORMATION: p69-mCRAMP

<400> SEQUENCE: 20

```
Met His His His His His His Gly Gly Gly Ser Gly Gly Gly Ser Gly
1               5               10              15

Gly Gly Ser Glu Asn Leu Tyr Phe Gln Gly Asp Trp Asn Asn Gln Ser
            20              25              30

Ile Val Lys Thr Gly Glu Arg Gln His Gly Ile His Ile Gln Gly Ser
        35              40              45

Asp Pro Gly Gly Val Arg Thr Ala Ser Gly Thr Thr Ile Lys Val Ser
    50              55              60

Gly Arg Gln Ala Gln Gly Ile Leu Leu Glu Asn Pro Ala Ala Glu Leu
65              70              75              80

Gln Phe Arg Asn Gly Ser Val Thr Ser Ser Gly Gln Leu Ser Asp Asp
                85              90              95
```

```
Gly Ile Arg Arg Phe Leu Gly Thr Val Thr Val Lys Ala Gly Lys Leu
            100             105             110

Val Ala Asp His Ala Thr Leu Ala Asn Val Gly Asp Thr Trp Asp Asp
            115             120             125

Asp Gly Ile Ala Leu Tyr Val Ala Gly Glu Gln Ala Gln Ala Ser Ile
            130             135             140

Ala Asp Ser Thr Leu Gln Gly Ala Gly Gly Val Gln Ile Glu Arg Gly
145             150             155             160

Ala Asn Val Thr Val Gln Arg Ser Ala Ile Val Asp Gly Gly Leu His
            165             170             175

Ile Gly Ala Leu Gln Ser Leu Gln Pro Glu Asp Leu Pro Pro Ser Arg
            180             185             190

Val Val Leu Arg Asp Thr Asn Val Thr Ala Val Pro Ala Ser Gly Ala
            195             200             205

Pro Ala Ala Val Ser Val Leu Gly Ala Ser Glu Leu Thr Leu Asp Gly
            210             215             220

Gly His Ile Thr Gly Gly Arg Ala Ala Gly Val Ala Ala Met Gln Gly
225             230             235             240

Ala Val Val His Leu Gln Arg Ala Thr Ile Arg Arg Gly Asp Ala Pro
            245             250             255

Ala Gly Gly Ala Val Pro Gly Gly Ala Val Pro Gly Gly Ala Val Pro
            260             265             270

Gly Gly Phe Gly Pro Gly Gly Phe Gly Pro Val Leu Asp Gly Trp Tyr
            275             280             285

Gly Val Asp Val Ser Gly Ser Ser Val Glu Leu Ala Gln Ser Ile Val
            290             295             300

Glu Ala Pro Glu Leu Gly Ala Ala Ile Arg Val Gly Arg Gly Ala Arg
305             310             315             320

Val Thr Val Ser Gly Gly Ser Leu Ser Ala Pro His Gly Asn Val Ile
            325             330             335

Glu Thr Gly Gly Ala Arg Arg Phe Ala Pro Gln Ala Ala Pro Leu Ser
            340             345             350

Ile Thr Leu Gln Ala Gly Ala His Ala Gln Gly Lys Ala Leu Leu Tyr
            355             360             365

Arg Val Leu Pro Glu Pro Val Lys Leu Thr Leu Thr Gly Gly Ala Asp
            370             375             380

Ala Gln Gly Asp Ile Val Ala Thr Glu Leu Pro Ser Ile Pro Gly Thr
385             390             395             400

Ser Ile Gly Pro Leu Asp Val Ala Leu Ala Ser Gln Ala Arg Trp Thr
            405             410             415

Gly Ala Thr Arg Ala Val Asp Ser Leu Ser Ile Asp Asn Ala Thr Trp
            420             425             430

Val Met Thr Asp Asn Ser Asn Val Gly Ala Leu Arg Leu Ala Ser Asp
            435             440             445

Gly Ser Val Asp Phe Gln Gln Pro Ala Glu Ala Gly Arg Phe Lys Val
            450             455             460

Leu Thr Val Asn Thr Leu Ala Gly Ser Gly Leu Phe Arg Met Asn Val
465             470             475             480

Phe Ala Asp Leu Gly Leu Ser Asp Lys Leu Val Val Met Gln Asp Ala
            485             490             495

Ser Gly Gln His Arg Leu Trp Val Arg Asn Ser Gly Ser Glu Pro Ala
            500             505             510
```

-continued

```
Ser Ala Asn Thr Leu Leu Leu Val Gln Thr Pro Leu Gly Ser Ala Ala
        515                 520                 525

Thr Phe Thr Leu Ala Asn Lys Asp Gly Lys Val Asp Ile Gly Thr Tyr
        530                 535                 540

Arg Tyr Arg Leu Ala Ala Asn Gly Asn Gly Gln Trp Ser Leu Val Gly
545                 550                 555                 560

Ala Lys Ala Pro Pro Gly Gly Gly Ser Gly Gly Gly Ser Gly Gly Gly
                565                 570                 575

Ser Gly Leu Leu Arg Lys Gly Gly Glu Lys Ile Gly Glu Lys Leu Lys
                580                 585                 590

Lys Ile Gly Gln Lys Ile Lys Asn Phe Phe Gln Lys Leu Val Pro Gln
                595                 600                 605

Pro Glu Gln
        610
```

<210> SEQ ID NO 21
<211> LENGTH: 611
<212> TYPE: PRT
<213> ORGANISM: artificial sequence
<220> FEATURE:
<223> OTHER INFORMATION: p69-mCRAMP scrambled

<400> SEQUENCE: 21

```
Met His His His His His His Gly Gly Gly Ser Gly Gly Gly Ser Gly
1                   5                   10                  15

Gly Gly Ser Glu Asn Leu Tyr Phe Gln Gly Asp Trp Asn Asn Gln Ser
                20                  25                  30

Ile Val Lys Thr Gly Glu Arg Gln His Gly Ile His Ile Gln Gly Ser
                35                  40                  45

Asp Pro Gly Gly Val Arg Thr Ala Ser Gly Thr Thr Ile Lys Val Ser
        50                  55                  60

Gly Arg Gln Ala Gln Gly Ile Leu Leu Glu Asn Pro Ala Ala Glu Leu
65                  70                  75                  80

Gln Phe Arg Asn Gly Ser Val Thr Ser Ser Gly Gln Leu Ser Asp Asp
                85                  90                  95

Gly Ile Arg Arg Phe Leu Gly Thr Val Thr Val Lys Ala Gly Lys Leu
                100                 105                 110

Val Ala Asp His Ala Thr Leu Ala Asn Val Gly Asp Thr Trp Asp Asp
        115                 120                 125

Asp Gly Ile Ala Leu Tyr Val Ala Gly Glu Gln Ala Gln Ala Ser Ile
        130                 135                 140

Ala Asp Ser Thr Leu Gln Gly Ala Gly Gly Val Gln Ile Glu Arg Gly
145                 150                 155                 160

Ala Asn Val Thr Val Gln Arg Ser Ala Ile Val Asp Gly Gly Leu His
                165                 170                 175

Ile Gly Ala Leu Gln Ser Leu Gln Pro Glu Asp Leu Pro Pro Ser Arg
                180                 185                 190

Val Val Leu Arg Asp Thr Asn Val Thr Ala Val Pro Ala Ser Gly Ala
                195                 200                 205

Pro Ala Ala Val Ser Val Leu Gly Ala Ser Glu Leu Thr Leu Asp Gly
        210                 215                 220

Gly His Ile Thr Gly Gly Arg Ala Ala Gly Val Ala Ala Met Gln Gly
225                 230                 235                 240

Ala Val Val His Leu Gln Arg Ala Thr Ile Arg Arg Gly Asp Ala Pro
                245                 250                 255
```

```
Ala Gly Gly Ala Val Pro Gly Gly Ala Val Pro Gly Gly Ala Val Pro
            260             265             270

Gly Gly Phe Gly Pro Gly Gly Phe Gly Pro Val Leu Asp Gly Trp Tyr
            275             280             285

Gly Val Asp Val Ser Gly Ser Ser Val Glu Leu Ala Gln Ser Ile Val
            290             295             300

Glu Ala Pro Glu Leu Gly Ala Ala Ile Arg Val Gly Arg Gly Ala Arg
305             310             315             320

Val Thr Val Ser Gly Gly Ser Leu Ser Ala Pro His Gly Asn Val Ile
            325             330             335

Glu Thr Gly Gly Ala Arg Arg Phe Ala Pro Gln Ala Ala Pro Leu Ser
            340             345             350

Ile Thr Leu Gln Ala Gly Ala His Ala Gln Gly Lys Ala Leu Leu Tyr
            355             360             365

Arg Val Leu Pro Glu Pro Val Lys Leu Thr Leu Thr Gly Gly Ala Asp
            370             375             380

Ala Gln Gly Asp Ile Val Ala Thr Glu Leu Pro Ser Ile Pro Gly Thr
385             390             395             400

Ser Ile Gly Pro Leu Asp Val Ala Leu Ala Ser Gln Ala Arg Trp Thr
            405             410             415

Gly Ala Thr Arg Ala Val Asp Ser Leu Ser Ile Asp Asn Ala Thr Trp
            420             425             430

Val Met Thr Asp Asn Ser Asn Val Gly Ala Leu Arg Leu Ala Ser Asp
            435             440             445

Gly Ser Val Asp Phe Gln Gln Pro Ala Glu Ala Gly Arg Phe Lys Val
            450             455             460

Leu Thr Val Asn Thr Leu Ala Gly Ser Gly Leu Phe Arg Met Asn Val
465             470             475             480

Phe Ala Asp Leu Gly Leu Ser Asp Lys Leu Val Val Met Gln Asp Ala
            485             490             495

Ser Gly Gln His Arg Leu Trp Val Arg Asn Ser Gly Ser Glu Pro Ala
            500             505             510

Ser Ala Asn Thr Leu Leu Leu Val Gln Thr Pro Leu Gly Ser Ala Ala
            515             520             525

Thr Phe Thr Leu Ala Asn Lys Asp Gly Lys Val Asp Ile Gly Thr Tyr
            530             535             540

Arg Tyr Arg Leu Ala Ala Asn Gly Asn Gly Gln Trp Ser Leu Val Gly
545             550             555             560

Ala Lys Ala Pro Pro Gly Gly Gly Ser Gly Gly Gly Ser Gly Gly Gly
            565             570             575

Ser Gly Lys Gln Leu Glu Lys Asn Ile Pro Gly Lys Lys Leu Pro Ile
            580             585             590

Leu Lys Arg Gln Lys Phe Glu Leu Gly Gly Gln Gln Glu Val Lys Gly
            595             600             605

Phe Ile Lys
    610
```

<210> SEQ ID NO 22
<211> LENGTH: 614
<212> TYPE: PRT
<213> ORGANISM: artificial sequence
<220> FEATURE:
<223> OTHER INFORMATION: P69-LL37

<400> SEQUENCE: 22

-continued

Met His His His His His Gly Gly Gly Ser Gly Gly Gly Ser Gly
1               5                   10                  15

Gly Gly Ser Glu Asn Leu Tyr Phe Gln Gly Asp Trp Asn Asn Gln Ser
            20                  25                  30

Ile Val Lys Thr Gly Glu Arg Gln His Gly Ile His Ile Gln Gly Ser
            35                  40                  45

Asp Pro Gly Gly Val Arg Thr Ala Ser Gly Thr Thr Ile Lys Val Ser
        50                  55                  60

Gly Arg Gln Ala Gln Gly Ile Leu Leu Glu Asn Pro Ala Ala Glu Leu
65                  70                  75                  80

Gln Phe Arg Asn Gly Ser Val Thr Ser Ser Gly Gln Leu Ser Asp Asp
                85                  90                  95

Gly Ile Arg Arg Phe Leu Gly Thr Val Thr Val Lys Ala Gly Lys Leu
            100                 105                 110

Val Ala Asp His Ala Thr Leu Ala Asn Val Gly Asp Thr Trp Asp Asp
            115                 120                 125

Asp Gly Ile Ala Leu Tyr Val Ala Gly Glu Gln Ala Gln Ala Ser Ile
        130                 135                 140

Ala Asp Ser Thr Leu Gln Gly Ala Gly Gly Val Gln Ile Glu Arg Gly
145                 150                 155                 160

Ala Asn Val Thr Val Gln Arg Ser Ala Ile Val Asp Gly Gly Leu His
                165                 170                 175

Ile Gly Ala Leu Gln Ser Leu Gln Pro Glu Asp Leu Pro Pro Ser Arg
            180                 185                 190

Val Val Leu Arg Asp Thr Asn Val Thr Ala Val Pro Ala Ser Gly Ala
            195                 200                 205

Pro Ala Ala Val Ser Val Leu Gly Ala Ser Glu Leu Thr Leu Asp Gly
        210                 215                 220

Gly His Ile Thr Gly Gly Arg Ala Ala Gly Val Ala Ala Met Gln Gly
225                 230                 235                 240

Ala Val Val His Leu Gln Arg Ala Thr Ile Arg Arg Gly Asp Ala Pro
                245                 250                 255

Ala Gly Gly Ala Val Pro Gly Gly Ala Val Pro Gly Gly Ala Val Pro
            260                 265                 270

Gly Gly Phe Gly Pro Gly Gly Phe Gly Pro Val Leu Asp Gly Trp Tyr
            275                 280                 285

Gly Val Asp Val Ser Gly Ser Ser Val Glu Leu Ala Gln Ser Ile Val
        290                 295                 300

Glu Ala Pro Glu Leu Gly Ala Ala Ile Arg Val Gly Arg Gly Ala Arg
305                 310                 315                 320

Val Thr Val Ser Gly Gly Ser Leu Ser Ala Pro His Gly Asn Val Ile
                325                 330                 335

Glu Thr Gly Gly Ala Arg Arg Phe Ala Pro Gln Ala Ala Pro Leu Ser
            340                 345                 350

Ile Thr Leu Gln Ala Gly Ala His Ala Gln Gly Lys Ala Leu Leu Tyr
            355                 360                 365

Arg Val Leu Pro Glu Pro Val Lys Leu Thr Leu Thr Gly Gly Ala Asp
        370                 375                 380

Ala Gln Gly Asp Ile Val Ala Thr Glu Leu Pro Ser Ile Pro Gly Thr
385                 390                 395                 400

Ser Ile Gly Pro Leu Asp Val Ala Leu Ala Ser Gln Ala Arg Trp Thr
                405                 410                 415

Gly Ala Thr Arg Ala Val Asp Ser Leu Ser Ile Asp Asn Ala Thr Trp

```
              420              425              430
Val Met Thr Asp Asn Ser Asn Val Gly Ala Leu Arg Leu Ala Ser Asp
          435              440              445
Gly Ser Val Asp Phe Gln Gln Pro Ala Glu Ala Gly Arg Phe Lys Val
          450              455              460
Leu Thr Val Asn Thr Leu Ala Gly Ser Gly Leu Phe Arg Met Asn Val
465              470              475              480
Phe Ala Asp Leu Gly Leu Ser Asp Lys Leu Val Val Met Gln Asp Ala
              485              490              495
Ser Gly Gln His Arg Leu Trp Val Arg Asn Ser Gly Ser Glu Pro Ala
              500              505              510
Ser Ala Asn Thr Leu Leu Leu Val Gln Thr Pro Leu Gly Ser Ala Ala
              515              520              525
Thr Phe Thr Leu Ala Asn Lys Asp Gly Lys Val Asp Ile Gly Thr Tyr
          530              535              540
Arg Tyr Arg Leu Ala Ala Asn Gly Asn Gly Gln Trp Ser Leu Val Gly
545              550              555              560
Ala Lys Ala Pro Pro Gly Gly Gly Ser Gly Gly Gly Ser Gly Gly Gly
              565              570              575
Ser Leu Leu Gly Asp Phe Phe Arg Lys Ser Lys Glu Lys Ile Gly Lys
              580              585              590
Glu Phe Lys Arg Ile Val Gln Arg Ile Lys Asp Phe Leu Arg Asn Leu
              595              600              605
Val Pro Arg Thr Glu Ser
          610
```

```
<210> SEQ ID NO 23
<211> LENGTH: 340
<212> TYPE: PRT
<213> ORGANISM: artificial sequence
<220> FEATURE:
<223> OTHER INFORMATION: VP-1 His

<400> SEQUENCE: 23

Met His His His His His His Gly Gly Gly Ser Gly Gly Gly Ser Gly
1               5               10              15
Gly Gly Ser Glu Asn Leu Tyr Phe Gln Gly Thr Gly Gly Asp Arg Val
              20              25              30
Ala Asp Val Ile Glu Ser Ser Ile Gly Asp Ser Val Ser Arg Ala Leu
          35              40              45
Thr His Ala Leu Pro Ala Pro Thr Gly Gln Asn Thr Gln Val Ser Ser
          50              55              60
His Arg Leu Asp Thr Gly Arg Val Pro Ala Leu Gln Ala Ala Glu Ile
65              70              75              80
Gly Ala Ser Ser Asn Ala Ser Asp Glu Ser Met Ile Glu Thr Arg Cys
              85              90              95
Val Leu Asn Ser His Ser Thr Ala Glu Thr Thr Leu Asp Ser Phe Phe
          100             105             110
Ser Arg Ala Gly Leu Val Gly Glu Ile Asp Leu Pro Leu Glu Gly Thr
          115             120             125
Thr Asn Pro Asn Gly Tyr Ala Asn Trp Asp Ile Asp Ile Thr Gly Tyr
          130             135             140
Ala Gln Met Arg Arg Lys Val Glu Leu Phe Thr Tyr Met Arg Phe Asp
145             150             155             160
Ala Glu Phe Thr Phe Val Ala Cys Thr Pro Thr Gly Glu Val Val Pro
```

-continued

```
                  165                 170                 175
Gln Leu Leu Gln Tyr Met Phe Val Pro Pro Gly Ala Pro Lys Pro Asp
             180                 185                 190

Ser Arg Glu Ser Leu Ala Trp Gln Thr Ala Thr Asn Pro Ser Val Phe
         195                 200                 205

Val Lys Leu Ser Asp Pro Pro Ala Gln Val Ser Val Pro Phe Met Ser
     210                 215                 220

Pro Ala Ser Ala Tyr Gln Trp Phe Tyr Asp Gly Tyr Pro Thr Phe Gly
 225                 230                 235                 240

Glu His Lys Gln Glu Lys Asp Leu Glu Tyr Gly Ala Cys Pro Asn Asn
                 245                 250                 255

Met Met Gly Thr Phe Ser Val Arg Thr Val Gly Thr Ser Lys Ser Lys
             260                 265                 270

Tyr Pro Leu Val Val Arg Ile Tyr Met Arg Met Lys His Val Arg Ala
         275                 280                 285

Trp Ile Pro Arg Pro Met Arg Asn Gln Asn Tyr Leu Phe Lys Ala Asn
     290                 295                 300

Pro Asn Tyr Ala Gly Asn Ser Ile Lys Pro Thr Gly Ala Ser Arg Thr
 305                 310                 315                 320

Ala Ile Thr Thr Leu Leu Glu Ser Gly Gly Gly Ser Gly Gly Gly Ser
             325                 330                 335

Gly Gly Gly Ser
             340

<210> SEQ ID NO 24
<211> LENGTH: 374
<212> TYPE: PRT
<213> ORGANISM: artificial sequence
<220> FEATURE:
<223> OTHER INFORMATION: VP-1 mCRAMP

<400> SEQUENCE: 24

Met His His His His His His Gly Gly Gly Ser Gly Gly Gly Ser Gly
1               5                   10                  15

Gly Gly Ser Glu Asn Leu Tyr Phe Gln Gly Thr Gly Gly Asp Arg Val
             20                  25                  30

Ala Asp Val Ile Glu Ser Ser Ile Gly Asp Ser Val Ser Arg Ala Leu
         35                  40                  45

Thr His Ala Leu Pro Ala Pro Thr Gly Gln Asn Thr Gln Val Ser Ser
     50                  55                  60

His Arg Leu Asp Thr Gly Arg Val Pro Ala Leu Gln Ala Ala Glu Ile
 65                  70                  75                  80

Gly Ala Ser Ser Asn Ala Ser Asp Glu Ser Met Ile Glu Thr Arg Cys
                 85                  90                  95

Val Leu Asn Ser His Ser Thr Ala Glu Thr Thr Leu Asp Ser Phe Phe
             100                 105                 110

Ser Arg Ala Gly Leu Val Gly Glu Ile Asp Leu Pro Leu Glu Gly Thr
         115                 120                 125

Thr Asn Pro Asn Gly Tyr Ala Asn Trp Asp Ile Asp Ile Thr Gly Tyr
     130                 135                 140

Ala Gln Met Arg Arg Lys Val Glu Leu Phe Thr Tyr Met Arg Phe Asp
 145                 150                 155                 160

Ala Glu Phe Thr Phe Val Ala Cys Thr Pro Thr Gly Glu Val Val Pro
             165                 170                 175

Gln Leu Leu Gln Tyr Met Phe Val Pro Pro Gly Ala Pro Lys Pro Asp
```

-continued

```
                    180             185                 190

Ser Arg Glu Ser Leu Ala Trp Gln Thr Ala Thr Asn Pro Ser Val Phe
            195             200                 205

Val Lys Leu Ser Asp Pro Pro Ala Gln Val Ser Val Pro Phe Met Ser
            210             215                 220

Pro Ala Ser Ala Tyr Gln Trp Phe Tyr Asp Gly Tyr Pro Thr Phe Gly
    225                 230             235                 240

Glu His Lys Gln Glu Lys Asp Leu Glu Tyr Gly Ala Cys Pro Asn Asn
                    245             250                 255

Met Met Gly Thr Phe Ser Val Arg Thr Val Gly Thr Ser Lys Ser Lys
                    260             265                 270

Tyr Pro Leu Val Val Arg Ile Tyr Met Arg Met Lys His Val Arg Ala
            275             280                 285

Trp Ile Pro Arg Pro Met Arg Asn Gln Asn Tyr Leu Phe Lys Ala Asn
            290             295                 300

Pro Asn Tyr Ala Gly Asn Ser Ile Lys Pro Thr Gly Ala Ser Arg Thr
    305                 310             315                 320

Ala Ile Thr Thr Leu Leu Glu Ser Gly Gly Gly Ser Gly Gly Gly Ser
                    325             330                 335

Gly Gly Gly Ser Gly Leu Leu Arg Lys Gly Gly Glu Lys Ile Gly Glu
                    340             345                 350

Lys Leu Lys Lys Ile Gly Gln Lys Ile Lys Asn Phe Phe Gln Lys Leu
            355             360                 365

Val Pro Gln Pro Glu Gln
        370
```

```
<210> SEQ ID NO 25
<211> LENGTH: 377
<212> TYPE: PRT
<213> ORGANISM: artificial sequence
<220> FEATURE:
<223> OTHER INFORMATION: VP-1 LL37

<400> SEQUENCE: 25

Met His His His His His His Gly Gly Gly Ser Gly Gly Gly Ser Gly
    1               5                   10                  15

Gly Gly Ser Glu Asn Leu Tyr Phe Gln Gly Thr Gly Gly Asp Arg Val
                    20              25                  30

Ala Asp Val Ile Glu Ser Ser Ile Gly Asp Ser Val Ser Arg Ala Leu
            35              40                  45

Thr His Ala Leu Pro Ala Pro Thr Gly Gln Asn Thr Gln Val Ser Ser
            50              55                  60

His Arg Leu Asp Thr Gly Arg Val Pro Ala Leu Gln Ala Ala Glu Ile
    65                  70              75                  80

Gly Ala Ser Ser Asn Ala Ser Asp Glu Ser Met Ile Glu Thr Arg Cys
                    85              90                  95

Val Leu Asn Ser His Ser Thr Ala Glu Thr Thr Leu Asp Ser Phe Phe
                    100             105                 110

Ser Arg Ala Gly Leu Val Gly Glu Ile Asp Leu Pro Leu Glu Gly Thr
            115             120                 125

Thr Asn Pro Asn Gly Tyr Ala Asn Trp Asp Ile Asp Ile Thr Gly Tyr
            130             135                 140

Ala Gln Met Arg Arg Lys Val Glu Leu Phe Thr Tyr Met Arg Phe Asp
    145                 150             155                 160

Ala Glu Phe Thr Phe Val Ala Cys Thr Pro Thr Gly Glu Val Val Pro
```

```
              165              170              175
Gln Leu Leu Gln Tyr Met Phe Val Pro Pro Gly Ala Pro Lys Pro Asp
         180              185              190

Ser Arg Glu Ser Leu Ala Trp Gln Thr Ala Thr Asn Pro Ser Val Phe
         195              200              205

Val Lys Leu Ser Asp Pro Pro Ala Gln Val Ser Val Pro Phe Met Ser
     210              215              220

Pro Ala Ser Ala Tyr Gln Trp Phe Tyr Asp Gly Tyr Pro Thr Phe Gly
225              230              235              240

Glu His Lys Gln Glu Lys Asp Leu Glu Tyr Gly Ala Cys Pro Asn Asn
         245              250              255

Met Met Gly Thr Phe Ser Val Arg Thr Val Gly Thr Ser Lys Ser Lys
         260              265              270

Tyr Pro Leu Val Val Arg Ile Tyr Met Arg Met Lys His Val Arg Ala
         275              280              285

Trp Ile Pro Arg Pro Met Arg Asn Gln Asn Tyr Leu Phe Lys Ala Asn
         290              295              300

Pro Asn Tyr Ala Gly Asn Ser Ile Lys Pro Thr Gly Ala Ser Arg Thr
305              310              315              320

Ala Ile Thr Thr Leu Leu Glu Ser Gly Gly Gly Ser Gly Gly Gly Ser
         325              330              335

Gly Gly Gly Ser Leu Leu Gly Asp Phe Phe Arg Lys Ser Lys Glu Lys
         340              345              350

Ile Gly Lys Glu Phe Lys Arg Ile Val Gln Arg Ile Lys Asp Phe Leu
         355              360              365

Arg Asn Leu Val Pro Arg Thr Glu Ser
     370              375

<210> SEQ ID NO 26
<211> LENGTH: 18
<212> TYPE: PRT
<213> ORGANISM: artificial sequence
<220> FEATURE:
<223> OTHER INFORMATION: VP fragment EV71

<400> SEQUENCE: 26

Tyr Pro Thr Phe Gly Glu His Lys Gln Glu Lys Asp Leu Glu Tyr Gly
1               5               10              15

Ala Cys

<210> SEQ ID NO 27
<211> LENGTH: 15
<212> TYPE: PRT
<213> ORGANISM: artificial sequence
<220> FEATURE:
<223> OTHER INFORMATION: VP fragment EV71

<400> SEQUENCE: 27

Asp Thr Gly Glu Val Pro Ala Leu Gln Ala Ala Glu Ile Gly Ala
1               5               10              15

<210> SEQ ID NO 28
<211> LENGTH: 15
<212> TYPE: PRT
<213> ORGANISM: artificial sequence
<220> FEATURE:
<223> OTHER INFORMATION: VP fragment EV71

<400> SEQUENCE: 28
```

-continued

```
Ala Gly Gly Thr Gly Thr Glu Asp Ser His Pro Pro Tyr Lys Gln
1               5                   10                  15

<210> SEQ ID NO 29
<211> LENGTH: 61
<212> TYPE: PRT
<213> ORGANISM: artificial sequence
<220> FEATURE:
<223> OTHER INFORMATION: fusion protein

<400> SEQUENCE: 29

Asp Thr Gly Glu Val Pro Ala Leu Gln Ala Ala Glu Ile Gly Ala Gly
1               5                   10                  15

Gly Gly Ser Gly Gly Gly Ser Gly Gly Gly Ser Gly Leu Leu Arg Lys
            20                  25                  30

Gly Gly Glu Lys Ile Gly Glu Lys Leu Lys Lys Ile Gly Gln Lys Ile
        35                  40                  45

Lys Asn Phe Phe Gln Lys Leu Val Pro Gln Pro Glu Gln
    50                  55                  60

<210> SEQ ID NO 30
<211> LENGTH: 64
<212> TYPE: PRT
<213> ORGANISM: artificial sequence
<220> FEATURE:
<223> OTHER INFORMATION: fusion protein

<400> SEQUENCE: 30

Tyr Pro Thr Phe Gly Glu His Lys Gln Glu Lys Asp Leu Glu Tyr Gly
1               5                   10                  15

Ala Cys Gly Gly Gly Ser Gly Gly Gly Ser Gly Gly Gly Ser Gly Leu
            20                  25                  30

Leu Arg Lys Gly Gly Glu Lys Ile Gly Glu Lys Leu Lys Lys Ile Gly
        35                  40                  45

Gln Lys Ile Lys Asn Phe Phe Gln Lys Leu Val Pro Gln Pro Glu Gln
    50                  55                  60

<210> SEQ ID NO 31
<211> LENGTH: 61
<212> TYPE: PRT
<213> ORGANISM: artificial sequence
<220> FEATURE:
<223> OTHER INFORMATION: fusion protein

<400> SEQUENCE: 31

Ala Gly Gly Thr Gly Thr Glu Asp Ser His Pro Pro Tyr Lys Gln Gly
1               5                   10                  15

Gly Gly Ser Gly Gly Gly Ser Gly Gly Gly Ser Gly Leu Leu Arg Lys
            20                  25                  30

Gly Gly Glu Lys Ile Gly Glu Lys Leu Lys Lys Ile Gly Gln Lys Ile
        35                  40                  45

Lys Asn Phe Phe Gln Lys Leu Val Pro Gln Pro Glu Gln
    50                  55                  60

<210> SEQ ID NO 32
<211> LENGTH: 55
<212> TYPE: PRT
<213> ORGANISM: artificial sequence
<220> FEATURE:
<223> OTHER INFORMATION: fusion protein

<400> SEQUENCE: 32
```

```
His His His His His His Asp Thr Gly Glu Val Pro Ala Leu Gln Ala
1               5                   10                  15

Ala Glu Ile Gly Ala Gly Leu Leu Arg Lys Gly Gly Glu Lys Ile Gly
            20                  25                  30

Glu Lys Leu Lys Lys Ile Gly Gln Lys Ile Lys Asn Phe Phe Gln Lys
        35                  40                  45

Leu Val Pro Gln Pro Glu Gln
    50                  55

<210> SEQ ID NO 33
<211> LENGTH: 58
<212> TYPE: PRT
<213> ORGANISM: artificial sequence
<220> FEATURE:
<223> OTHER INFORMATION: fusion protein

<400> SEQUENCE: 33

His His His His His His Tyr Pro Thr Phe Gly Glu His Lys Gln Glu
1               5                   10                  15

Lys Asp Leu Glu Tyr Gly Ala Cys Gly Leu Leu Arg Lys Gly Gly Glu
            20                  25                  30

Lys Ile Gly Glu Lys Leu Lys Lys Ile Gly Gln Lys Ile Lys Asn Phe
        35                  40                  45

Phe Gln Lys Leu Val Pro Gln Pro Glu Gln
    50                  55

<210> SEQ ID NO 34
<211> LENGTH: 55
<212> TYPE: PRT
<213> ORGANISM: artificial sequence
<220> FEATURE:
<223> OTHER INFORMATION: fusion protein

<400> SEQUENCE: 34

His His His His His His Ala Gly Gly Thr Gly Thr Glu Asp Ser His
1               5                   10                  15

Pro Pro Tyr Lys Gln Gly Leu Leu Arg Lys Gly Gly Glu Lys Ile Gly
            20                  25                  30

Glu Lys Leu Lys Lys Ile Gly Gln Lys Ile Lys Asn Phe Phe Gln Lys
        35                  40                  45

Leu Val Pro Gln Pro Glu Gln
    50                  55

<210> SEQ ID NO 35
<211> LENGTH: 49
<212> TYPE: PRT
<213> ORGANISM: artificial sequence
<220> FEATURE:
<223> OTHER INFORMATION: fusion protein

<400> SEQUENCE: 35

Asp Thr Gly Glu Val Pro Ala Leu Gln Ala Ala Glu Ile Gly Ala Gly
1               5                   10                  15

Leu Leu Arg Lys Gly Gly Glu Lys Ile Gly Glu Lys Leu Lys Lys Ile
            20                  25                  30

Gly Gln Lys Ile Lys Asn Phe Phe Gln Lys Leu Val Pro Gln Pro Glu
        35                  40                  45

Gln

<210> SEQ ID NO 36
```

```
<211> LENGTH: 52
<212> TYPE: PRT
<213> ORGANISM: artificial sequence
<220> FEATURE:
<223> OTHER INFORMATION: fusion protein

<400> SEQUENCE: 36

Tyr Pro Thr Phe Gly Glu His Lys Gln Glu Lys Asp Leu Glu Tyr Gly
1               5                   10                  15

Ala Cys Gly Leu Leu Arg Lys Gly Gly Glu Lys Ile Gly Glu Lys Leu
            20                  25                  30

Lys Lys Ile Gly Gln Lys Ile Lys Asn Phe Phe Gln Lys Leu Val Pro
        35                  40                  45

Gln Pro Glu Gln
    50

<210> SEQ ID NO 37
<211> LENGTH: 49
<212> TYPE: PRT
<213> ORGANISM: artificial sequence
<220> FEATURE:
<223> OTHER INFORMATION: fusion protein

<400> SEQUENCE: 37

Ala Gly Gly Thr Gly Thr Glu Asp Ser His Pro Pro Tyr Lys Gln Gly
1               5                   10                  15

Leu Leu Arg Lys Gly Gly Glu Lys Ile Gly Glu Lys Leu Lys Lys Ile
            20                  25                  30

Gly Gln Lys Ile Lys Asn Phe Phe Gln Lys Leu Val Pro Gln Pro Glu
        35                  40                  45

Gln

<210> SEQ ID NO 38
<211> LENGTH: 392
<212> TYPE: PRT
<213> ORGANISM: Neisseria meningitidis (group B)

<400> SEQUENCE: 38

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Tyr Gln Leu Gln Leu Thr Glu Ala Gln Ala Ala Asn Gly
        35                  40                  45

Gly Ala Ser Gly Gln Val Lys Val Thr Lys Val Thr Lys Ala Lys Ser
    50                  55                  60

Arg Ile Arg Thr Lys Ile Ser Asp Phe Gly Ser Phe Ile Gly Phe Lys
65                  70                  75                  80

Gly Ser Glu Asp Leu Gly Asp Gly Leu Lys Ala Val Trp Gln Leu Glu
                85                  90                  95

Gln Asp Val Ser Val Ala Gly Gly Gly Ala Thr Gln Trp Gly Asn Arg
            100                 105                 110

Glu Ser Phe Ile Gly Leu Ala Gly Glu Phe Gly Thr Leu Arg Ala Gly
        115                 120                 125

Arg Val Ala Asn Gln Phe Asp Asp Ala Ser Gln Ala Ile Asp Pro Trp
    130                 135                 140

Asp Ser Asn Asn Asp Val Ala Ser Gln Leu Gly Ile Phe Lys Arg His
145                 150                 155                 160
```

-continued

```
Asp Asp Met Pro Val Ser Val Arg Tyr Asp Ser Pro Glu Phe Ser Gly
            165                 170                 175

Phe Ser Gly Ser Val Gln Phe Val Pro Ile Gln Asn Ser Lys Ser Ala
            180                 185                 190

Tyr Thr Pro Ala Tyr Tyr Thr Lys Asp Thr Asn Asn Asn Leu Thr Leu
            195                 200                 205

Val Pro Ala Val Val Gly Lys Pro Gly Ser Asp Val Tyr Tyr Ala Gly
        210                 215                 220

Leu Asn Tyr Lys Asn Gly Gly Phe Ala Gly Asn Tyr Ala Phe Lys Tyr
225                 230                 235                 240

Ala Arg His Ala Asn Val Gly Arg Asn Ala Phe Glu Leu Phe Leu Ile
            245                 250                 255

Gly Ser Gly Ser Asp Gln Ala Lys Gly Thr Asp Pro Leu Lys Asn His
            260                 265                 270

Gln Val His Arg Leu Thr Gly Gly Tyr Glu Glu Gly Gly Leu Asn Leu
            275                 280                 285

Ala Leu Ala Ala Gln Leu Asp Leu Ser Glu Asn Gly Asp Lys Thr Lys
        290                 295                 300

Asn Ser Thr Thr Glu Ile Ala Ala Thr Ala Ser Tyr Arg Phe Gly Asn
305                 310                 315                 320

Ala Val Pro Arg Ile Ser Tyr Ala His Gly Phe Asp Phe Ile Glu Arg
            325                 330                 335

Gly Lys Lys Gly Glu Asn Thr Ser Tyr Asp Gln Ile Ile Ala Gly Val
            340                 345                 350

Asp Tyr Asp Phe Ser Lys Arg Thr Ser Ala Ile Val Ser Gly Ala Trp
            355                 360                 365

Leu Lys Arg Asn Thr Gly Ile Gly Asn Tyr Thr Gln Ile Asn Ala Ala
        370                 375                 380

Ser Val Gly Leu Arg His Lys Phe
385                 390
```

```
<210> SEQ ID NO 39
<211> LENGTH: 331
<212> TYPE: PRT
<213> ORGANISM: Neisseria meningitidis (group B)

<400> SEQUENCE: 39

Met Lys Lys Ser Leu Ile Ala Leu Thr Leu Ala Ala Leu Pro Val Ala
1               5                   10                  15

Ala Met Ala Asp Val Thr Leu Tyr Gly Thr Ile Lys Ala Gly Val Glu
            20                  25                  30

Thr Ser Arg Ser Val Phe His Gln Asn Gly Gln Val Thr Glu Val Thr
            35                  40                  45

Thr Ala Thr Gly Ile Val Asp Leu Gly Ser Lys Ile Gly Phe Lys Gly
        50                  55                  60

Gln Glu Asp Leu Gly Asn Gly Leu Lys Ala Ile Trp Gln Val Glu Gln
65                  70                  75                  80

Lys Ala Ser Ile Ala Gly Thr Asp Ser Gly Trp Gly Asn Arg Gln Ser
            85                  90                  95

Phe Ile Gly Leu Lys Gly Gly Phe Gly Lys Leu Arg Val Gly Arg Leu
            100                 105                 110

Asn Ser Val Leu Lys Asp Thr Gly Asp Ile Asn Pro Trp Asp Ser Lys
            115                 120                 125

Ser Asp Tyr Leu Gly Val Asn Lys Ile Ala Glu Pro Glu Ala Arg Leu
        130                 135                 140
```

-continued

```
Ile Ser Val Arg Tyr Asp Ser Pro Glu Phe Ala Gly Leu Ser Gly Ser
145                 150                 155                 160

Val Gln Tyr Ala Leu Asn Asp Asn Ala Gly Arg His Asn Ser Glu Ser
                165                 170                 175

Tyr His Ala Gly Phe Asn Tyr Lys Asn Gly Gly Phe Phe Val Gln Tyr
            180                 185                 190

Gly Gly Ala Tyr Lys Arg His His Gln Val Gln Glu Gly Leu Asn Ile
        195                 200                 205

Glu Lys Tyr Gln Ile His Arg Leu Val Ser Gly Tyr Asp Asn Asp Ala
    210                 215                 220

Leu Tyr Ala Ser Val Ala Val Gln Gln Gln Asp Ala Lys Leu Thr Asp
225                 230                 235                 240

Ala Ser Asn Ser His Asn Ser Gln Thr Glu Val Ala Ala Thr Leu Ala
                245                 250                 255

Tyr Arg Phe Gly Asn Val Thr Pro Arg Val Ser Tyr Ala His Gly Phe
            260                 265                 270

Lys Gly Leu Val Asp Asp Ala Asp Ile Gly Asn Glu Tyr Asp Gln Val
        275                 280                 285

Val Val Gly Ala Glu Tyr Asp Phe Ser Lys Arg Thr Ser Ala Leu Val
    290                 295                 300

Ser Ala Gly Trp Leu Gln Glu Gly Lys Gly Glu Asn Lys Phe Val Ala
305                 310                 315                 320

Thr Ala Gly Gly Val Gly Leu Arg His Lys Phe
                325                 330
```

```
<210> SEQ ID NO 40
<211> LENGTH: 495
<212> TYPE: PRT
<213> ORGANISM: Neisseria meningitidis (group B)

<400> SEQUENCE: 40
```

```
Met Leu Lys Lys Ile Lys Lys Ala Leu Phe Gln Pro Lys Lys Phe Phe
1               5                   10                  15

Gln Asp Ser Met Trp Leu Thr Thr Ser Pro Phe Tyr Leu Thr Pro Pro
            20                  25                  30

Arg Asn Asn Leu Phe Val Ile Ser Asn Leu Gly Gln Leu Asn Gln Val
        35                  40                  45

Gln Ser Leu Ile Lys Ile Gln Lys Leu Thr Asn Asn Leu Leu Val Ile
    50                  55                  60

Leu Tyr Thr Ser Lys Asn Leu Lys Met Pro Lys Leu Val His Gln Ser
65                  70                  75                  80

Ala Asn Lys Asn Leu Phe Glu Ser Ile Tyr Leu Phe Glu Leu Pro Arg
                85                  90                  95

Ser Pro Asn Asn Ile Thr Pro Lys Lys Leu Leu Tyr Ile Tyr Arg Ser
            100                 105                 110

Tyr Lys Lys Ile Leu Asn Ile Ile Gln Pro Ala His Leu Tyr Met Leu
        115                 120                 125

Ser Phe Thr Gly His Tyr Ser Tyr Leu Ile Ser Ile Ala Lys Lys Lys
    130                 135                 140

Asn Ile Thr Thr His Leu Ile Asp Glu Gly Thr Gly Thr Tyr Ala Pro
145                 150                 155                 160

Leu Leu Glu Ser Phe Ser Tyr His Pro Thr Lys Leu Glu Arg Tyr Leu
                165                 170                 175

Ile Gly Asn Asn Leu Asn Ile Lys Gly Tyr Ile Asp His Phe Asp Ile
```

-continued

```
                180                185                190

Leu His Val Pro Phe Pro Glu Tyr Ala Lys Lys Ile Phe Asn Ala Lys
         195                200                205

Lys Tyr Asn Arg Phe Phe Ala His Ala Gly Gly Ile Ser Ile Asn Asn
         210                215                220

Asn Ile Ala Asn Leu Gln Lys Lys Tyr Gln Ile Ser Lys Asn Asp Tyr
225                230                235                240

Ile Phe Val Ser Gln Arg Tyr Pro Ile Ser Asp Asp Leu Tyr Tyr Lys
                245                250                255

Ser Ile Val Glu Ile Leu Asn Ser Ile Ser Leu Gln Ile Lys Gly Lys
                260                265                270

Ile Phe Ile Lys Leu His Pro Lys Glu Met Gly Asn Asn Tyr Val Met
         275                280                285

Ser Leu Phe Leu Asn Met Val Glu Ile Asn Pro Arg Leu Val Val Ile
         290                295                300

Asn Glu Pro Pro Phe Leu Ile Glu Pro Leu Ile Tyr Leu Thr Asn Pro
305                310                315                320

Lys Gly Ile Ile Gly Leu Ala Ser Ser Ser Leu Ile Tyr Thr Pro Leu
                325                330                335

Leu Ser Pro Ser Thr Gln Cys Leu Ser Ile Gly Glu Leu Ile Ile Asn
         340                345                350

Leu Ile Gln Lys Tyr Ser Met Val Glu Asn Thr Glu Met Ile Gln Glu
         355                360                365

His Leu Glu Ile Ile Lys Lys Phe Asn Phe Ile Asn Ile Leu Asn Asp
         370                375                380

Leu Asn Gly Val Ile Ser Asn Pro Leu Phe Lys Thr Glu Glu Thr Phe
385                390                395                400

Glu Thr Leu Leu Lys Ser Ala Glu Phe Ala Tyr Lys Ser Lys Asn Tyr
                405                410                415

Phe Gln Ala Ile Phe Tyr Trp Gln Leu Ala Ser Lys Asn Asn Ile Thr
         420                425                430

Leu Leu Gly His Lys Ala Leu Trp Tyr Tyr Asn Ala Leu Tyr Asn Val
         435                440                445

Lys Gln Ile Tyr Lys Met Glu Tyr Ser Asp Ile Phe Tyr Ile Asp Asn
         450                455                460

Ile Ser Val Asp Phe His Ser Lys Asp Lys Leu Thr Trp Glu Lys Ile
465                470                475                480

Lys His Tyr Tyr Tyr Ser Ala Asp Asn Arg Ile Gly Arg Asp Arg
                485                490                495
```

```
<210> SEQ ID NO 41
<211> LENGTH: 1231
<212> TYPE: PRT
<213> ORGANISM: artificial sequence
<220> FEATURE:
<223> OTHER INFORMATION: spike protein

<400> SEQUENCE: 41

Met Phe Val Phe Leu Val Leu Leu Pro Leu Val Ser Ser Gln Cys Val
1                5                10                15

Asn Leu Thr Thr Arg Thr Gln Leu Pro Pro Ala Tyr Thr Asn Ser Phe
                20                25                30

Thr Arg Gly Val Tyr Tyr Pro Asp Lys Val Phe Arg Ser Ser Val Leu
         35                40                45

His Ser Thr Gln Asp Leu Phe Leu Pro Phe Phe Ser Asn Val Thr Trp
```

-continued

```
                 50                   55                   60

Phe His Ala Ile His Val Ser Gly Thr Asn Gly Thr Lys Arg Phe Asp
65                   70                   75                   80

Asn Pro Val Leu Pro Phe Asn Asp Gly Val Tyr Phe Ala Ser Thr Glu
                     85                   90                   95

Lys Ser Asn Ile Ile Arg Gly Trp Ile Phe Gly Thr Thr Leu Asp Ser
                100                  105                  110

Lys Thr Gln Ser Leu Leu Ile Val Asn Asn Ala Thr Asn Val Val Ile
            115                  120                  125

Lys Val Cys Glu Phe Gln Phe Cys Asn Asp Pro Phe Leu Gly Val Tyr
        130                  135                  140

Tyr His Lys Asn Asn Lys Ser Trp Met Glu Ser Glu Phe Arg Val Tyr
145                  150                  155                  160

Ser Ser Ala Asn Asn Cys Thr Phe Glu Tyr Val Ser Gln Pro Phe Leu
                165                  170                  175

Met Asp Leu Glu Gly Lys Gln Gly Asn Phe Lys Asn Leu Arg Glu Phe
            180                  185                  190

Val Phe Lys Asn Ile Asp Gly Tyr Phe Lys Ile Tyr Ser Lys His Thr
        195                  200                  205

Pro Ile Asn Leu Val Arg Asp Leu Pro Gln Gly Phe Ser Ala Leu Glu
    210                  215                  220

Pro Leu Val Asp Leu Pro Ile Gly Ile Asn Ile Thr Arg Phe Gln Thr
225                  230                  235                  240

Leu Leu Ala Leu His Arg Ser Tyr Leu Thr Pro Gly Asp Ser Ser Ser
                245                  250                  255

Gly Trp Thr Ala Gly Ala Ala Ala Tyr Tyr Val Gly Tyr Leu Gln Pro
            260                  265                  270

Arg Thr Phe Leu Leu Lys Tyr Asn Glu Asn Gly Thr Ile Thr Asp Ala
        275                  280                  285

Val Asp Cys Ala Leu Asp Pro Leu Ser Glu Thr Lys Cys Thr Leu Lys
    290                  295                  300

Ser Phe Thr Val Glu Lys Gly Ile Tyr Gln Thr Ser Asn Phe Arg Val
305                  310                  315                  320

Gln Pro Thr Glu Ser Ile Val Arg Phe Pro Asn Ile Thr Asn Leu Cys
                325                  330                  335

Pro Phe Gly Glu Val Phe Asn Ala Thr Arg Phe Ala Ser Val Tyr Ala
            340                  345                  350

Trp Asn Arg Lys Arg Ile Ser Asn Cys Val Ala Asp Tyr Ser Val Leu
        355                  360                  365

Tyr Asn Ser Ala Ser Phe Ser Thr Phe Lys Cys Tyr Gly Val Ser Pro
    370                  375                  380

Thr Lys Leu Asn Asp Leu Cys Phe Thr Asn Val Tyr Ala Asp Ser Phe
385                  390                  395                  400

Val Ile Arg Gly Asp Glu Val Arg Gln Ile Ala Pro Gly Gln Thr Gly
            405                  410                  415

Lys Ile Ala Asp Tyr Asn Tyr Lys Leu Pro Asp Asp Phe Thr Gly Cys
            420                  425                  430

Val Ile Ala Trp Asn Ser Asn Asn Leu Asp Ser Lys Val Gly Gly Asn
        435                  440                  445

Tyr Asn Tyr Leu Tyr Arg Leu Phe Arg Lys Ser Asn Leu Lys Pro Phe
    450                  455                  460

Glu Arg Asp Ile Ser Thr Glu Ile Tyr Gln Ala Gly Ser Thr Pro Cys
465                  470                  475                  480
```

```
Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
                530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
                595                 600                 605

Ala Val Leu Tyr Gln Asp Val Asn Cys Thr Glu Val Pro Val Ala Ile
                610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
                660                 665                 670

Ser Tyr Gln Thr Gln Thr Asn Ser Pro Arg Gly Ser Ala Val Ala Ser
                675                 680                 685

Gln Ser Ile Ile Ala Tyr Thr Met Ser Leu Gly Ala Glu Asn Ser Val
                690                 695                 700

Ala Tyr Ser Asn Asn Ser Ile Ala Ile Pro Thr Asn Phe Thr Ile Ser
705                 710                 715                 720

Val Thr Thr Glu Ile Leu Pro Val Ser Met Thr Lys Thr Ser Val Asp
                725                 730                 735

Cys Thr Met Tyr Ile Cys Gly Asp Ser Thr Glu Cys Ser Asn Leu Leu
                740                 745                 750

Leu Gln Tyr Gly Ser Phe Cys Thr Gln Leu Asn Arg Ala Leu Thr Gly
                755                 760                 765

Ile Ala Val Glu Gln Asp Lys Asn Thr Gln Glu Val Phe Ala Gln Val
                770                 775                 780

Lys Gln Ile Tyr Lys Thr Pro Pro Ile Lys Asp Phe Gly Gly Phe Asn
785                 790                 795                 800

Phe Ser Gln Ile Leu Pro Asp Pro Ser Lys Pro Ser Lys Arg Ser Phe
                805                 810                 815

Ile Glu Asp Leu Leu Phe Asn Lys Val Thr Leu Ala Asp Ala Gly Phe
                820                 825                 830

Ile Lys Gln Tyr Gly Asp Cys Leu Gly Asp Ile Ala Ala Arg Asp Leu
                835                 840                 845

Ile Cys Ala Gln Lys Phe Asn Gly Leu Thr Val Leu Pro Pro Leu Leu
                850                 855                 860

Thr Asp Glu Met Ile Ala Gln Tyr Thr Ser Ala Leu Leu Ala Gly Thr
865                 870                 875                 880

Ile Thr Ser Gly Trp Thr Phe Gly Ala Gly Ala Ala Leu Gln Ile Pro
                885                 890                 895
```

-continued

```
Phe Ala Met Gln Met Ala Tyr Arg Phe Asn Gly Ile Gly Val Thr Gln
        900                 905                 910

Asn Val Leu Tyr Glu Asn Gln Lys Leu Ile Ala Asn Gln Phe Asn Ser
        915                 920                 925

Ala Ile Gly Lys Ile Gln Asp Ser Leu Ser Ser Thr Ala Ser Ala Leu
        930                 935                 940

Gly Lys Leu Gln Asp Val Val Asn Gln Asn Ala Gln Ala Leu Asn Thr
945                 950                 955                 960

Leu Val Lys Gln Leu Ser Ser Asn Phe Gly Ala Ile Ser Ser Val Leu
                965                 970                 975

Asn Asp Ile Leu Ser Arg Leu Asp Pro Pro Glu Ala Glu Val Gln Ile
            980                 985                 990

Asp Arg Leu Ile Thr Gly Arg Leu  Gln Ser Leu Gln Thr  Tyr Val Thr
        995                 1000                1005

Gln Gln  Leu Ile Arg Ala Ala  Glu Ile Arg Ala Ser  Ala Asn Leu
    1010                1015                1020

Ala Ala  Thr Lys Met Ser Glu  Cys Val Leu Gly Gln  Ser Lys Arg
    1025                1030                1035

Val Asp  Phe Cys Gly Lys Gly  Tyr His Leu Met Ser  Phe Pro Gln
    1040                1045                1050

Ser Ala  Pro His Gly Val Val  Phe Leu His Val Thr  Tyr Val Pro
    1055                1060                1065

Ala Gln  Glu Lys Asn Phe Thr  Thr Ala Pro Ala Ile  Cys His Asp
    1070                1075                1080

Gly Lys  Ala His Phe Pro Arg  Glu Gly Val Phe Val  Ser Asn Gly
    1085                1090                1095

Thr His  Trp Phe Val Thr Gln  Arg Asn Phe Tyr Glu  Pro Gln Ile
    1100                1105                1110

Ile Thr  Thr Asp Asn Thr Phe  Val Ser Gly Asn Cys  Asp Val Val
    1115                1120                1125

Ile Gly  Ile Val Asn Asn Thr  Val Tyr Asp Pro Leu  Gln Pro Glu
    1130                1135                1140

Leu Asp  Ser Phe Lys Glu Glu  Leu Asp Lys Tyr Phe  Lys Asn His
    1145                1150                1155

Thr Ser  Pro Asp Val Asp Leu  Gly Asp Ile Ser Gly  Ile Asn Ala
    1160                1165                1170

Ser Val  Val Asn Ile Gln Lys  Glu Ile Asp Arg Leu  Asn Glu Val
    1175                1180                1185

Ala Lys  Asn Leu Asn Glu Ser  Leu Ile Asp Leu Glu  Gly Arg Ser
    1190                1195                1200

Gly Gly  Tyr Ile Pro Glu Ala  Pro Arg Asp Gly Gln  Ala Tyr Val
    1205                1210                1215

Arg Lys  Asp Gly Glu Trp Val  Leu Leu Ser Thr Phe  Leu
    1220                1225                1230

<210> SEQ ID NO 42
<211> LENGTH: 1333
<212> TYPE: PRT
<213> ORGANISM: artificial sequence
<220> FEATURE:
<223> OTHER INFORMATION: spike protein plus mCRAMP

<400> SEQUENCE: 42

Met Phe Val Phe Leu Val Leu Leu Pro Leu Val Ser Ser Gln Cys Val
1               5                   10                  15
```

-continued

```
Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
            35              40              45

His Ser Thr Gln Asp Leu Phe Leu Pro Phe Phe Ser Asn Val Thr Trp
    50              55              60

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
            85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
            115             120             125

Lys Val Cys Glu Phe Gln Phe Cys Asn Asp Pro Phe Leu Gly Val Tyr
    130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
            195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
            275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
```

-continued

```
               435                   440                   445
Tyr Asn Tyr Leu Tyr Arg Leu Phe Arg Lys Ser Asn Leu Lys Pro Phe
    450                   455                   460
Glu Arg Asp Ile Ser Thr Glu Ile Tyr Gln Ala Gly Ser Thr Pro Cys
465                   470                   475                   480
Asn Gly Val Glu Gly Phe Asn Cys Tyr Phe Pro Leu Gln Ser Tyr Gly
                    485                   490                   495
Phe Gln Pro Thr Asn Gly Val Gly Tyr Gln Pro Tyr Arg Val Val Val
                500                   505                   510
Leu Ser Phe Glu Leu Leu His Ala Pro Ala Thr Val Cys Gly Pro Lys
                515                   520                   525
Lys Ser Thr Asn Leu Val Lys Asn Lys Cys Val Asn Phe Asn Phe Asn
    530                   535                   540
Gly Leu Thr Gly Thr Gly Val Leu Thr Glu Ser Asn Lys Lys Phe Leu
545                   550                   555                   560
Pro Phe Gln Gln Phe Gly Arg Asp Ile Ala Asp Thr Thr Asp Ala Val
                565                   570                   575
Arg Asp Pro Gln Thr Leu Glu Ile Leu Asp Ile Thr Pro Cys Ser Phe
                580                   585                   590
Gly Gly Val Ser Val Ile Thr Pro Gly Thr Asn Thr Ser Asn Gln Val
                595                   600                   605
Ala Val Leu Tyr Gln Gly Val Asn Cys Thr Glu Val Pro Val Ala Ile
    610                   615                   620
His Ala Asp Gln Leu Thr Pro Thr Trp Arg Val Tyr Ser Thr Gly Ser
625                   630                   635                   640
Asn Val Phe Gln Thr Arg Ala Gly Cys Leu Ile Gly Ala Glu His Val
                645                   650                   655
Asn Asn Ser Tyr Glu Cys Asp Ile Pro Ile Gly Ala Gly Ile Cys Ala
                660                   665                   670
Ser Tyr Gln Thr Gln Thr Asn Ser Pro Gly Ser Ala Ser Ser Val Ala
                675                   680                   685
Ser Gln Ser Ile Ile Ala Tyr Thr Met Ser Leu Gly Ala Glu Asn Ser
    690                   695                   700
Val Ala Tyr Ser Asn Asn Ser Ile Ala Ile Pro Thr Asn Phe Thr Ile
705                   710                   715                   720
Ser Val Thr Thr Glu Ile Leu Pro Val Ser Met Thr Lys Thr Ser Val
                725                   730                   735
Asp Cys Thr Met Tyr Ile Cys Gly Asp Ser Thr Glu Cys Ser Asn Leu
                740                   745                   750
Leu Leu Gln Tyr Gly Ser Phe Cys Thr Gln Leu Asn Arg Ala Leu Thr
                755                   760                   765
Gly Ile Ala Val Glu Gln Asp Lys Asn Thr Gln Glu Val Phe Ala Gln
    770                   775                   780
Val Lys Gln Ile Tyr Lys Thr Pro Pro Ile Lys Asp Phe Gly Gly Phe
785                   790                   795                   800
Asn Phe Ser Gln Ile Leu Pro Asp Pro Ser Lys Pro Ser Lys Arg Ser
                    805                   810                   815
Pro Ile Glu Asp Leu Leu Phe Asn Lys Val Thr Leu Ala Asp Ala Gly
                820                   825                   830
Phe Ile Lys Gln Tyr Gly Asp Cys Leu Gly Asp Ile Ala Ala Arg Asp
                835                   840                   845
Leu Ile Cys Ala Gln Lys Phe Asn Gly Leu Thr Val Leu Pro Pro Leu
    850                   855                   860
```

-continued

```
Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Pro Ala Leu Gln Ile
                    885                 890                 895

Pro Phe Pro Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
            915                 920                 925

Ser Ala Ile Gly Lys Ile Gln Asp Ser Leu Ser Ser Thr Pro Ser Ala
            930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
                980                 985                 990

Ile Asp Arg Leu Ile Thr Gly Arg  Leu Gln Ser Leu Gln  Thr Tyr Val
                995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Gly Ser  Gly Tyr Ile Pro Glu  Ala Pro Arg
    1205                1210                1215

Asp Gly  Gln Ala Tyr Val Arg  Lys Asp Gly Glu Trp  Val Leu Leu
    1220                1225                1230

Ser Thr  Phe Leu Gly Arg Ser  Leu Glu Val Leu Phe  Gln Gly Pro
    1235                1240                1245

Gly His  His His His His His  His His Ser Ala Trp  Ser His Pro
    1250                1255                1260
```

-continued

```
Gln Phe  Glu Lys Gly Gly Gly  Ser Gly Gly Gly  Ser  Gly Gly Ser
    1265              1270              1275

Ala Trp  Ser His Pro Gln Phe  Glu Lys Gly Gly Gly  Ser Gly Gly
    1280              1285              1290

Gly Ser  Gly Gly Gly Ser Gly  Leu Leu Arg Lys Gly  Gly Glu Lys
    1295              1300              1305

Ile Gly  Glu Lys Leu Lys Lys  Ile Gly Gln Lys Ile  Lys Asn Phe
    1310              1315              1320

Phe Gln  Lys Leu Val Pro Gln  Pro Glu Gln
    1325              1330

<210> SEQ ID NO 43
<211> LENGTH: 1288
<212> TYPE: PRT
<213> ORGANISM: artificial sequence
<220> FEATURE:
<223> OTHER INFORMATION: spike protein

<400> SEQUENCE: 43

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
        20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
            85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
            165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
            245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285
```

-continued

```
Val Asp Cys Ala Leu Asp Pro Leu Ser Glu Thr Lys Cys Thr Leu Lys
290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
                325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365

Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
                405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
        435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
            515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gly Ser Ala Ser Ser Val Ala
            675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
```

```
705                 710                 715                 720
Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
                740                 745                 750

Leu Leu Gln Tyr Gly Ser Phe Cys Thr Gln Leu Asn Arg Ala Leu Thr
                755                 760                 765

Gly Ile Ala Val Glu Gln Asp Lys Asn Thr Gln Glu Val Phe Ala Gln
                770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Pro Ile Glu Asp Leu Leu Phe Asn Lys Val Thr Leu Ala Asp Ala Gly
                820                 825                 830

Phe Ile Lys Gln Tyr Gly Asp Cys Leu Gly Asp Ile Ala Ala Arg Asp
                835                 840                 845

Leu Ile Cys Ala Gln Lys Phe Asn Gly Leu Thr Val Leu Pro Pro Leu
        850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Pro Ala Leu Gln Ile
                885                 890                 895

Pro Phe Pro Met Gln Met Ala Tyr Arg Phe Asn Gly Ile Gly Val Thr
                900                 905                 910

Gln Asn Val Leu Tyr Glu Asn Gln Lys Leu Ile Ala Asn Gln Phe Asn
                915                 920                 925

Ser Ala Ile Gly Lys Ile Gln Asp Ser Leu Ser Ser Thr Pro Ser Ala
        930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
                980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125
```

-continued

```
Val Ile  Gly Ile Val Asn Asn  Thr Val Tyr Asp Pro  Leu Gln Pro
    1130             1135              1140

Glu Leu  Asp Ser Phe Lys Glu  Glu Leu Asp Lys Tyr  Phe Lys Asn
    1145             1150              1155

His Thr  Ser Pro Asp Val Asp  Leu Gly Asp Ile Ser  Gly Ile Asn
    1160             1165              1170

Ala Ser  Val Val Asn Ile Gln  Lys Glu Ile Asp Arg  Leu Asn Glu
    1175             1180              1185

Val Ala  Lys Asn Leu Asn Glu  Ser Leu Ile Asp Leu  Gln Glu Leu
    1190             1195              1200

Gly Lys  Tyr Glu Gln Gly Ser  Gly Tyr Ile Pro Glu  Ala Pro Arg
    1205             1210              1215

Asp Gly  Gln Ala Tyr Val Arg  Lys Asp Gly Glu Trp  Val Leu Leu
    1220             1225              1230

Ser Thr  Phe Leu Gly Arg Ser  Leu Glu Val Leu Phe  Gln Gly Pro
    1235             1240              1245

Gly His  His His His His His  His His Ser Ala Trp  Ser His Pro
    1250             1255              1260

Gln Phe  Glu Lys Gly Gly Gly  Ser Gly Gly Gly Gly  Ser Gly Gly
    1265             1270              1275

Ser Ala  Trp Ser His Pro Gln  Phe Glu Lys
    1280             1285

<210> SEQ ID NO 44
<211> LENGTH: 1237
<212> TYPE: PRT
<213> ORGANISM: artificial sequence
<220> FEATURE:
<223> OTHER INFORMATION: spike protein

<400> SEQUENCE: 44

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190
```

-continued

```
Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
        210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
                260                 265                 270

Arg Thr Phe Leu Leu Lys Tyr Asn Glu Asn Gly Thr Ile Thr Asp Ala
                275                 280                 285

Val Asp Cys Ala Leu Asp Pro Leu Ser Glu Thr Lys Cys Thr Leu Lys
        290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
                340                 345                 350

Trp Asn Arg Lys Arg Ile Ser Asn Cys Val Ala Asp Tyr Ser Val Leu
                355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
                420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
                500                 505                 510

Leu Ser Phe Glu Leu Leu His Ala Pro Ala Thr Val Cys Gly Pro Lys
                515                 520                 525

Lys Ser Thr Asn Leu Val Lys Asn Lys Cys Val Asn Phe Asn Phe Asn
        530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
                580                 585                 590

Gly Gly Val Ser Val Ile Thr Pro Gly Thr Asn Thr Ser Asn Gln Val
        595                 600                 605
```

```
Ala Val Leu Tyr Gln Gly Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gly Ser Ala Ser Ser Val Ala
    675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
    755             760             765

Gly Ile Ala Val Glu Gln Asp Lys Asn Thr Gln Glu Val Phe Ala Gln
    770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Pro Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
    835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Pro Ala Leu Gln Ile
            885             890             895

Pro Phe Pro Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
    915             920             925

Ser Ala Ile Gly Lys Ile Gln Asp Ser Leu Ser Ser Thr Pro Ser Ala
    930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Pro Pro Glu Ala Glu Val Gln
            980             985             990

Ile Asp Arg Leu Ile Thr Gly Arg  Leu Gln Ser Leu Gln  Thr Tyr Val
            995             1000             1005

Thr Gln  Gln Leu Ile Arg Ala  Ala Glu Ile Arg Ala  Ser Ala Asn
    1010             1015             1020

Leu Ala  Ala Thr Lys Met Ser  Glu Cys Val Leu Gly  Gln Ser Lys
```

```
      1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Gly Ser  Gly Tyr Ile Pro Glu  Ala Pro Arg
    1205                1210                1215

Asp Gly  Gln Ala Tyr Val Arg  Lys Asp Gly Glu Trp  Val Leu Leu
    1220                1225                1230

Ser Thr  Phe Leu
    1235

<210> SEQ ID NO 45
<211> LENGTH: 1283
<212> TYPE: PRT
<213> ORGANISM: artificial sequence
<220> FEATURE:
<223> OTHER INFORMATION: spike - mCRAMP

<400> SEQUENCE: 45

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
```

```
              130                   135                   140

Tyr His Lys Asn Asn Lys Ser Trp Met Glu Ser Glu Phe Arg Val Tyr
145                   150                   155                   160

Ser Ser Ala Asn Asn Cys Thr Phe Glu Tyr Val Ser Gln Pro Phe Leu
                  165                   170                   175

Met Asp Leu Glu Gly Lys Gln Gly Asn Phe Lys Asn Leu Arg Glu Phe
                  180                   185                   190

Val Phe Lys Asn Ile Asp Gly Tyr Phe Lys Ile Tyr Ser Lys His Thr
                  195                   200                   205

Pro Ile Asn Leu Val Arg Asp Leu Pro Gln Gly Phe Ser Ala Leu Glu
              210                   215                   220

Pro Leu Val Asp Leu Pro Ile Gly Ile Asn Ile Thr Arg Phe Gln Thr
225                   230                   235                   240

Leu Leu Ala Leu His Arg Ser Tyr Leu Thr Pro Gly Asp Ser Ser Ser
                  245                   250                   255

Gly Trp Thr Ala Gly Ala Ala Ala Tyr Tyr Val Gly Tyr Leu Gln Pro
                  260                   265                   270

Arg Thr Phe Leu Leu Lys Tyr Asn Glu Asn Gly Thr Ile Thr Asp Ala
                  275                   280                   285

Val Asp Cys Ala Leu Asp Pro Leu Ser Glu Thr Lys Cys Thr Leu Lys
              290                   295                   300

Ser Phe Thr Val Glu Lys Gly Ile Tyr Gln Thr Ser Asn Phe Arg Val
305                   310                   315                   320

Gln Pro Thr Glu Ser Ile Val Arg Phe Pro Asn Ile Thr Asn Leu Cys
                  325                   330                   335

Pro Phe Gly Glu Val Phe Asn Ala Thr Arg Phe Ala Ser Val Tyr Ala
                  340                   345                   350

Trp Asn Arg Lys Arg Ile Ser Asn Cys Val Ala Asp Tyr Ser Val Leu
                  355                   360                   365

Tyr Asn Ser Ala Ser Phe Ser Thr Phe Lys Cys Tyr Gly Val Ser Pro
              370                   375                   380

Thr Lys Leu Asn Asp Leu Cys Phe Thr Asn Val Tyr Ala Asp Ser Phe
385                   390                   395                   400

Val Ile Arg Gly Asp Glu Val Arg Gln Ile Ala Pro Gly Gln Thr Gly
                  405                   410                   415

Lys Ile Ala Asp Tyr Asn Tyr Lys Leu Pro Asp Asp Phe Thr Gly Cys
                  420                   425                   430

Val Ile Ala Trp Asn Ser Asn Asn Leu Asp Ser Lys Val Gly Gly Asn
                  435                   440                   445

Tyr Asn Tyr Leu Tyr Arg Leu Phe Arg Lys Ser Asn Leu Lys Pro Phe
              450                   455                   460

Glu Arg Asp Ile Ser Thr Glu Ile Tyr Gln Ala Gly Ser Thr Pro Cys
465                   470                   475                   480

Asn Gly Val Glu Gly Phe Asn Cys Tyr Phe Pro Leu Gln Ser Tyr Gly
                  485                   490                   495

Phe Gln Pro Thr Asn Gly Val Gly Tyr Gln Pro Tyr Arg Val Val Val
                  500                   505                   510

Leu Ser Phe Glu Leu Leu His Ala Pro Ala Thr Val Cys Gly Pro Lys
                  515                   520                   525

Lys Ser Thr Asn Leu Val Lys Asn Lys Cys Val Asn Phe Asn Phe Asn
              530                   535                   540

Gly Leu Thr Gly Thr Gly Val Leu Thr Glu Ser Asn Lys Lys Phe Leu
545                   550                   555                   560
```

```
Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Gly Val Asn Cys Thr Glu Val Pro Val Ala Ile
        610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Gly Ser Ala Ser Ser Val Ala
        675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
            755             760             765

Gly Ile Ala Val Glu Gln Asp Lys Asn Thr Gln Glu Val Phe Ala Gln
    770             775             780

Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Pro Ile Glu Asp Leu Leu Phe Asn Lys Val Thr Leu Ala Asp Ala Gly
            820             825             830

Phe Ile Lys Gln Tyr Gly Asp Cys Leu Gly Asp Ile Ala Ala Arg Asp
            835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Pro Ala Leu Gln Ile
            885             890             895

Pro Phe Pro Met Gln Met Ala Tyr Arg Phe Asn Gly Ile Gly Val Thr
            900             905             910

Gln Asn Val Leu Tyr Glu Asn Gln Lys Leu Ile Ala Asn Gln Phe Asn
            915             920             925

Ser Ala Ile Gly Lys Ile Gln Asp Ser Leu Ser Ser Thr Pro Ser Ala
        930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975
```

Leu Asn Asp Ile Leu Ser Arg Leu Asp Pro Pro Glu Ala Glu Val Gln
                980                 985                 990

Ile Asp Arg Leu Ile Thr Gly Arg  Leu Gln Ser Leu Gln  Thr Tyr Val
        995                 1000                1005

Thr Gln  Gln Leu Ile Arg Ala  Ala Glu Ile Arg Ala  Ser Ala Asn
    1010                1015                1020

Leu Ala  Ala Thr Lys Met Ser  Glu Cys Val Leu Gly  Gln Ser Lys
    1025                1030                1035

Arg Val  Asp Phe Cys Gly Lys  Gly Tyr His Leu Met  Ser Phe Pro
    1040                1045                1050

Gln Ser  Ala Pro His Gly Val  Val Phe Leu His Val  Thr Tyr Val
    1055                1060                1065

Pro Ala  Gln Glu Lys Asn Phe  Thr Thr Ala Pro Ala  Ile Cys His
    1070                1075                1080

Asp Gly  Lys Ala His Phe Pro  Arg Glu Gly Val Phe  Val Ser Asn
    1085                1090                1095

Gly Thr  His Trp Phe Val Thr  Gln Arg Asn Phe Tyr  Glu Pro Gln
    1100                1105                1110

Ile Ile  Thr Thr Asp Asn Thr  Phe Val Ser Gly Asn  Cys Asp Val
    1115                1120                1125

Val Ile  Gly Ile Val Asn Asn  Thr Val Tyr Asp Pro  Leu Gln Pro
    1130                1135                1140

Glu Leu  Asp Ser Phe Lys Glu  Glu Leu Asp Lys Tyr  Phe Lys Asn
    1145                1150                1155

His Thr  Ser Pro Asp Val Asp  Leu Gly Asp Ile Ser  Gly Ile Asn
    1160                1165                1170

Ala Ser  Val Val Asn Ile Gln  Lys Glu Ile Asp Arg  Leu Asn Glu
    1175                1180                1185

Val Ala  Lys Asn Leu Asn Glu  Ser Leu Ile Asp Leu  Gln Glu Leu
    1190                1195                1200

Gly Lys  Tyr Glu Gln Gly Ser  Gly Tyr Ile Pro Glu  Ala Pro Arg
    1205                1210                1215

Asp Gly  Gln Ala Tyr Val Arg  Lys Asp Gly Glu Trp  Val Leu Leu
    1220                1225                1230

Ser Thr  Phe Leu Gly Gly Gly  Ser Gly Gly Gly Ser  Gly Gly Gly
    1235                1240                1245

Ser Gly  Leu Leu Arg Lys Gly  Gly Glu Lys Ile Gly  Glu Lys Leu
    1250                1255                1260

Lys Lys  Ile Gly Gln Lys Ile  Lys Asn Phe Phe Gln  Lys Leu Val
    1265                1270                1275

Pro Gln  Pro Glu Gln
    1280

<210> SEQ ID NO 46
<211> LENGTH: 3696
<212> TYPE: DNA
<213> ORGANISM: artificial sequence
<220> FEATURE:
<223> OTHER INFORMATION: coding sequence spike protein

<400> SEQUENCE: 46
atgtttgttt ttcttgtttt attgccacta gtctctagtc agtgtgttaa tcttacaacc     60
agaactcaat taccccctgc atacactaat tctttcacac gtggtgttta ttaccctgac    120
aaagttttca gatcctcagt tttacattca actcaggact tgttcttacc tttcttttcc    180

-continued

```
aatgttactt ggttccatgc tatacatgtc tctgggacca atggtactaa gaggtttgat      240
aaccctgtcc taccatttaa tgatggtgtt tattttgctt ccactgagaa gtctaacata      300
ataagaggct ggatttttgg tactacttta gattcgaaga cccagtccct acttattgtt      360
aataacgcta ctaatgttgt tattaaagtc tgtgaatttc aattttgtaa tgatccattt      420
ttgggtgttt attaccacaa aaacaacaaa agttggatgg aaagtgagtt cagagtttat      480
tctagtgcga ataattgcac ttttgaatat gtctctcagc ctttttctat ggaccttgaa      540
ggaaaacagg gtaatttcaa aaatcttagg gaatttgtgt ttaagaatat tgatggttat      600
tttaaaatat attctaagca cacgcctatt aatttagtgc gtgatctccc tcagggtttt      660
tcggctttag aaccattggt agatttgcca ataggtatta acatcactag gtttcaaact      720
ttacttgctt tacatagaag ttatttgact cctggtgatt cttcttcagg ttggacagct      780
ggtgctgcag cttattatgt gggttatctt caacctagga ctttttctatt aaaatataat     840 gaaaatggaa ccattacaga tgctgtagac tgtgcacttg accctctctc agaaacaaag      900
tgtacgttga aatccttcac tgtagaaaaa ggaatctatc aaacttctaa ctttagagtc      960
caaccaacag aatctattgt tagatttcct aatattacaa acttgtgccc ttttggtgaa     1020 gttttttaacg ccaccagatt tgcatctgtt tatgcttgga acaggaagag aatcagcaac     1080
tgtgttgctg attattctgt cctatataat tccgcatcat tttccacttt taagtgttat     1140
ggagtgtctc ctactaaatt aaatgatctc tgctttacta atgtctatgc agattcattt     1200
gtaattagag gtgatgaagt cagacaaatc gctccagggc aaactggaaa gattgctgat     1260
tataattata aattaccaga tgattttaca ggctgcgtta tagcttggaa ttctaacaat     1320
cttgattcta aggttggtgg taattataat tacctgtata gattgtttag gaagtctaat     1380
ctcaaacctt ttgagagaga tatttcaact gaaatctatc aggccggtag cacaccttgt     1440
aatggtgttg aaggttttaa ttgttacttt cctttacaat catatggttt ccaacccact     1500
aatggtgttg gttaccaacc atacagagta gtagtacttt cttttgaact ctacatgca      1560 ccagcaactg tttgtggacc taaaaagtct actaatttgg ttaaaaacaa atgtgtcaat     1620
ttcaacttca atggtttaac aggcacaggt gttcttactg agtctaacaa aaagtttctg     1680
cctttccaac aatttggcag agacattgct gacactactg atgctgtccg tgatccacag     1740
acacttgaga ttcttgacat tacaccatgt tcttttggtg gtgtcagtgt tataacacca     1800
ggaacaaata cttctaacca ggttgctgtt ctttatcagg atgttaactg cacagaagtc     1860
cctgttgcta ttcatgcaga tcaacttact cctacttggc gtgtttattc tacaggttct     1920 aatgttttttc aaacacgtgc aggctgttta ataggggctg aacatgtcaa caactcatat     1980
gagtgtgaca tacccattgg tgcaggtata tgcgctagtt atcagactca gactaattct     2040
cctcgtgggt ctgctgtagc tagtcaatcc atcattgcct acactatgtc acttggtgca     2100
gaaaattcag ttgcttactc taataactct attgccatac ccacaaattt tactattagt     2160
gttaccacag aaattctacc agtgtctatg accaagacat cagtagattg tacaatgtac     2220
atttgtggtg attcaactga atgcagcaat cttttgttgc aatatggcag ttttttgtaca     2280 caattaaacc gtgctttaac tggaatagct gttgaacaag acaaaaacac ccaagaagtt     2340
tttgcacaag tcaaacaaat ttacaaaaca ccaccaatta agatttttgg tggttttaat     2400
ttttcacaaa tattaccaga tccatcaaaa ccaagcaaga ggtcattcat tgaagatcta     2460
cttttcaaca aagtgacact tgcagatgct ggcttcatca acaatatatg gtgattgcctt     2520 ggtgatattg ctgctagaga cctcatttgt gcacaaaagt ttaacggcct tactgttttg     2580
```

-continued

```
ccacctttgc tcacagatga aatgattgct caatacactt ctgcactgtt agcgggtaca      2640
atcacttctg gttggacctt tggtgcaggt gcagcattac aaataccatt tgcaatgcaa      2700
atggcttata ggtttaatgg tattggagtt acacagaatg ttctctatga gaaccaaaaa      2760
ttgattgcca accaatttaa tagtgctatt ggcaaaattc aagactcact ttcttccaca      2820
gcaagtgcac ttggaaaact tcaagatgtg gtcaaccaaa atgcacaagc tttaaacacg      2880
cttgttaaac aacttagctc caattttggt gcaatttcaa gtgtttttaaa tgatatcctt      2940 tcacgtcttg acccacctga ggctgaagtg caaattgata ggttgatcac aggcagactt      3000
caaagtttgc agacatatgt gactcaacaa ttaattagag ctgcagaaat cagagcttct      3060
gctaatcttg ctgctactaa aatgtcagag tgtgtacttg gacaatcaaa aagagttgat      3120
ttttgtggaa agggctatca tcttatgtcc ttccctcagt cagcacctca tggtgtagtc      3180
ttcttgcatg tgacttatgt ccctgcacaa gaaaagaact tcacaactgc tcctgccatt      3240
tgtcatgatg gaaaagcaca ctttcctcgt gaaggtgtct ttgtttcaaa tggcacacac      3300
tggtttgtaa cacaaaggaa tttttatgaa ccacaaatca ttactacaga caacacattt      3360
gtgtctggta actgtgatgt tgtaatagga attgtcaaca cacagtttaa tgatcctttg      3420
caacctgaat tagactcatt caaggaggag ttagataaat attttaagaa tcatacatca      3480
ccagatgttg atttaggtga catctctggc attaatgctt cagttgtaaa cattcaaaaa      3540
gaaattgacc gcctcaatga ggttgccaag aatttaaatg aatctctcat cgatctcgaa      3600
ggaaggtcag gcggctacat ccccgaggcc cccagggacg gccaggccta cgtgaggaag      3660
gacggcgagt gggtgctgct gagcaccttc ctgtag                              3696
```

<210> SEQ ID NO 47
<211> LENGTH: 4002
<212> TYPE: DNA
<213> ORGANISM: artificial sequence
<220> FEATURE:
<223> OTHER INFORMATION: coding sequence spike protein + mCRAMP

<400> SEQUENCE: 47

```
atgtttgttt ttcttgtttt attgccacta gtctctagtc agtgtgttaa tcttacaacc        60
agaactcaat taccccctgc atacactaat tctttcacac gtggtgttta ttaccctgac       120 aaagtttttca gatcctcagt tttacattca actcaggact tgttcttacc tttcttttcc       180
aatgttactt ggttccatgc tatacatgtc tctgggacca atggtactaa gaggtttgat       240
aaccctgtcc taccatttaa tgatggtgtt tattttgctt ccactgagaa gtctaacata       300
ataagaggct ggattttttgg tactactttta gattcgaaga cccagtccct acttattgtt       360
aataacgcta ctaatgttgt tattaaagtc tgtgaatttc aattttgtaa tgatccattt       420
ttgggtgttt attaccacaa aaacaacaaa agttggatgg aaagtgagtt cagagtttat       480
tctagtgcga ataattgcac ttttgaatat gtctctcagc ctttttcttat ggaccttgaa       540 ggaaaacagg gtaatttcaa aaatcttagg gaatttgtgt ttaagaatat tgatggttat       600
tttaaaatat attctaagca cacgcctatt aatttagtgc gtgatctccc tcagggtttt       660
tcggctttag aaccattggt agatttgcca ataggtatta acatcactag gtttcaaact       720
ttacttgctt tacatagaag ttatttgact cctggtgatt cttcttcagg ttggacagct       780
ggtgctgcag cttattatgt gggttatctt caacctagga ctttttctatt aaaatataat       840 gaaaatggaa ccattacaga tgctgtagac tgtgcacttg accctctctc agaaacaaag       900
```

-continued

```
tgtacgttga aatccttcac tgtagaaaaa ggaatctatc aaacttctaa cttttagagtc      960 caaccaacag aatctattgt tagatttcct aatattacaa acttgtgccc ttttggtgaa      1020 gttttttaacg ccaccagatt tgcatctgtt tatgcttgga acaggaagag aatcagcaac     1080
tgtgttgctg attattctgt cctatataat tccgcatcat tttccacttt taagtgttat      1140
ggagtgtctc ctactaaatt aaatgatctc tgctttacta atgtctatgc agattcattt      1200
gtaattagag gtgatgaagt cagacaaatc gctccagggc aaactggaaa gattgctgat      1260
tataattata aattaccaga tgattttaca ggctgcgtta tagcttggaa ttctaacaat      1320
cttgattcta aggttggtgg taattataat tacctgtata gattgtttag gaagtctaat      1380
ctcaaacctt ttgagagaga tatttcaact gaaatctatc aggccggtag cacaccttgt      1440
aatggtgttg aaggttttaa ttgttacttt cctttacaat catatggttt ccaacccact      1500
aatggtgttg gttaccaacc atacagagta gtagtacttt cttttgaact tctacatgca      1560
ccagcaactg tttgtggacc taaaaagtct actaatttgg ttaaaaacaa atgtgtcaat      1620
ttcaacttca atggtttaac aggcacaggt gttcttactg agtctaacaa aaagtttctg      1680
cctttccaac aatttggcag agacattgct gacactactg atgctgtccg tgatccacag      1740
acacttgaga ttcttgacat tacaccatgt tcttttggtg gtgtcagtgt tataacacca      1800
ggaacaaata cttctaacca ggttgctgtt ctttatcagg gtgttaactg cacagaagtc      1860
cctgttgcta ttcatgcaga tcaacttact cctacttggc gtgtttattc tacaggttct      1920
aatgtttttc aaacacgtgc aggctgttta ataggggctg aacatgtcaa caactcatat      1980
gagtgtgaca tacccattgg tgcaggtata tgcgctagtt atcagactca gactaattct      2040
cctgggtcgg catctagtgt agctagtcaa tccatcattg cctacactat gtcacttggt      2100
gcagaaaatt cagttgctta ctctaataac tctattgcca tacccacaaa ttttactatt      2160
agtgttacca cagaaattct accagtgtct atgaccaaga catcagtaga ttgtacaatg      2220
tacatttgtg gtgattcaac tgaatgcagc aatcttttgt tgcaatatgg cagttttttgt      2280 acacaattaa accgtgcttt aactggaata gctgttgaac aagacaaaaa cacccaagaa      2340
gtttttgcac aagtcaaaca aatttacaaa acaccaccaa ttaaagattt tggtggtttt      2400 aattttttcac aaatattacc agatccatca aaaccaagca agaggtcacc tattgaagat      2460
ctacttttca caaagtgac acttgcagat gctggcttca tcaaacaata tggtgattgc       2520
cttggtgata ttgctgctag agacctcatt tgtgcacaaa agtttaacgg ccttactgtt      2580
ttgccacctt tgctcacaga tgaaatgatt gctcaataca cttctgcact gttagcgggt      2640
acaatcactt ctggttggac ctttggtgca ggtcctgcat tacaaatacc atttcctatg      2700
caaatggctt ataggtttaa tggtattgga gttacacaga tgttctctta tgagaaccaa      2760
aaattgattg ccaaccaatt taatagtgct attggcaaaa ttcaagactc actttcttcc      2820
acaccaagtg cacttggaaa acttcaagat gtggtcaacc aaaatgcaca agctttaaac      2880
acgcttgtta acaacttag ctccaatttt ggtgcaattt caagtgtttt aaatgatatc       2940
ctttcacgtc ttgacccacc tgaggctgaa gtgcaaattg ataggttgat cacaggcaga      3000
cttcaaagtt tgcagacata tgtgactcaa caattaatta gagctgcaga aatcagagct      3060
tctgctaatc ttgctgctac taaaatgtca gagtgtgtac ttggacaatc aaaaagagtt      3120 gattttttgtg aaagggcta tcatcttatg tccttccctc agtcagcacc tcatggtgta      3180
gtcttcttgc atgtgactta tgtccctgca caagaaaaga acttcacaac tgctcctgcc      3240
atttgtcatg atggaaaagc acactttcct cgtgaaggtg tctttgtttc aaatggcaca      3300
```

```
cactggtttg taacacaaag gaattttat  gaaccacaaa tcattactac agacaacaca    3360
tttgtgtctg gtaactgtga tgttgtaata ggaattgtca acaacacagt ttatgatcct    3420
ttgcaacctg aattagactc attcaaggag gagttagata aatattttaa gaatcataca    3480
tcaccagatg ttgatttagg tgacatctct ggcattaatg cttcagttgt aaacattcaa    3540
aaagaaattg accgcctcaa tgaggttgcc aagaatttaa atgaatctct catcgatctc    3600
caagaacttg gaaagtatga gcaggggtca ggctacatcc ccgaggcccc cagggacggc    3660
caggcctacg tgaggaagga cggcgagtgg gtgctgctga gcaccttcct gggcaggagc    3720
ctggaggtgc tgttccaggg ccccggccat catcatcatc atcatcatca tagcgcttgg    3780
agccacccgc agttcgaaaa aggtggaggt tctggcggtg gatcgggagg ttcagcgtgg    3840
agccacccgc agttcgagaa aggtggaggt tctggcggtg gatcgggtgg aggttctgga    3900
cttctccgca aggtgggga  gaagattggt gaaaagctta agaaaattgg ccagaaaatt    3960
aagaattttt ttcagaaact tgtacctcag ccagagcagt ag                       4002
```

```
<210> SEQ ID NO 48
<211> LENGTH: 3867
<212> TYPE: DNA
<213> ORGANISM: artificial sequence
<220> FEATURE:
<223> OTHER INFORMATION: sequence encodiing spike protein with tags

<400> SEQUENCE: 48
atgtttgttt ttcttgtttt attgccacta gtctctagtc agtgtgttaa tcttacaacc      60
agaactcaat taccccctgc atacactaat tctttcacac gtggtgttta ttaccctgac     120
aaagttttca gatcctcagt tttacattca actcaggact tgttcttacc tttcttttcc     180
aatgttactt ggttccatgc tatacatgtc tctgggacca atggtactaa gaggtttgat     240
aaccctgtcc taccatttaa tgatggtgtt tattttgctt ccactgagaa gtctaacata     300
ataagaggct ggattttttgg tactacttta gattcgaaga cccagtccct acttattgtt     360
aataacgcta ctaatgttgt tattaaagtc tgtgaatttc aattttgtaa tgatccattt     420
ttgggtgttt attaccacaa aaacaacaaa agttggatgg aaagtgagtt cagagtttat     480
tctagtgcga ataattgcac ttttgaatat gtctctcagc ctttttcttat ggaccttgaa     540 ggaaaacagg gtaatttcaa aaatcttagg gaatttgtgt ttaagaatat tgatggttat     600
tttaaaatat attctaagca cacgcctatt aatttagtgc gtgatctccc tcagggtttt     660
tcggctttag aaccattggt agatttgcca ataggtatta acatcactag gtttcaaact     720
ttacttgctt tacatagaag ttatttgact cctggtgatt cttcttcagg ttggacagct     780
ggtgctgcag cttattatgt gggttatctt caacctagga ctttttctatt aaaatataat     840 gaaaatggaa ccattacaga tgctgtagac tgtgcacttg accctctctc agaaacaaag     900
tgtacgttga atccttcac  tgtagaaaaa ggaatctatc aaacttctaa ctttagagtc     960
caaccaacag aatctattgt tagatttcct aatattacaa acttgtgccc ttttggtgaa    1020
gtttttaacg ccaccagatt tgcatctgtt tatgcttgga acaggaagag aatcagcaac    1080
tgtgttgctg attattctgt cctatataat tccgcatcat tttccacttt taagtgttat    1140
ggagtgtctc ctactaaatt aaatgatctc tgctttacta atgtctatgc agattcattt    1200
gtaattagag gtgatgaagt cagacaaatc gctccaggc  aaactggaaa gattgctgat    1260
tataattata aattaccaga tgattttaca ggctgcgtta tagcttggaa ttctaacaat    1320
```

-continued

```
cttgattcta aggttggtgg taattataat tacctgtata gattgtttag gaagtctaat    1380
ctcaaacctt ttgagagaga tatttcaact gaaatctatc aggccggtag cacaccttgt    1440
aatggtgttg aaggtttaa ttgttacttt cctttacaat catatggttt ccaacccact     1500
aatggtgttg gttaccaacc atacagagta gtagtacttt cttttgaact tctacatgca     1560
ccagcaactg tttgtggacc taaaaagtct actaatttgg ttaaaaacaa atgtgtcaat     1620
ttcaacttca atggtttaac aggcacaggt gttcttactg agtctaacaa aaagtttctg     1680
cctttccaac aatttggcag agacattgct gacactactg atgctgtccg tgatccacag     1740
acacttgaga ttcttgacat tacaccatgt tcttttggtg gtgtcagtgt tataacacca     1800
ggaacaaata cttctaacca ggttgctgtt ctttatcagg atgttaactg cacagaagtc     1860
cctgttgcta ttcatgcaga tcaacttact cctacttggc gtgtttattc tacaggttct    1920 aatgttttc aaacacgtgc aggctgttta ataggggctg aacatgtcaa caactcatat      1980
gagtgtgaca tacccattgg tgcaggtata tgcgctagtt atcagactca gactaattct     2040
cctgggtcgg catctagtgt agctagtcaa tccatcattg cctacactat gtcacttggt     2100
gcagaaaatt cagttgctta ctctaataac tctattgcca tacccacaaa ttttactatt     2160
agtgttacca cagaaattct accagtgtct atgaccaaga catcagtaga ttgtacaatg     2220
tacatttgtg gtgattcaac tgaatgcagc aatcttttgt tgcaatatgg cagttttttgt   2280 acacaattaa accgtgcttt aactggaata gctgttgaac aagacaaaaa cacccaagaa     2340
gtttttgcac aagtcaaaca aatttacaaa acaccaccaa ttaaagattt tggtggtttt    2400
aatttttcac aaatattacc agatccatca aaaccaagca agaggtcacc tattgaagat     2460
ctacttttca caaagtgac acttgcagat gctggcttca tcaaacaata tggtgattgc      2520
cttggtgata ttgctgctag agacctcatt tgtgcacaaa agtttaacgg ccttactgtt    2580
ttgccacctt tgctcacaga tgaaatgatt gctcaataca cttctgcact gttagcgggt     2640
acaatcactt ctggttggac ctttggtgca ggtcctgcat tacaaatacc atttcctatg     2700
caaatggctt ataggtttaa tggtattgga gttacacaga atgttctcta tgagaaccaa     2760
aaattgattg ccaaccaatt taatagtgct attggcaaaa ttcaagactc actttcttcc    2820
acaccaagtg cacttggaaa acttcaagat gtggtcaacc aaaatgcaca agctttaaac     2880
acgcttgtta acaacttag ctccaatttt ggtgcaattt caagtgtttt aaatgatatc      2940
ctttcacgtc ttgacccacc tgaggctgaa gtgcaaattg ataggttgat cacaggcaga     3000
cttcaaagtt tgcagacata tgtgactcaa caattaatta gagctgcaga aatcagagct     3060
tctgctaatc ttgctgctac taaaatgtca gagtgtgtac ttggacaatc aaaaagagtt     3120
gatttttgtg gaaagggcta tcatcttatg tccttccctc agtcagcacc tcatggtgta     3180
gtcttcttgc atgtgactta tgtccctgca caagaaaaga acttcacaac tgctcctgcc     3240
atttgtcatg atggaaaagc acactttcct cgtgaaggtg tctttgtttc aaatggcaca     3300
cactggtttg taacacaaag gaattttat gaaccacaaa tcattactac agacaacaca      3360
tttgtgtctg gtaactgtga tgttgtaata ggaattgtca acaacacagt ttatgatcct     3420
ttgcaacctg aattagactc attcaaggag gagttagata atatttttaa gaatcataca     3480
tcaccagatg ttgatttagg tgacatctct ggcattaatg cttcagttgt aaacattcaa     3540
aaagaaattg accgcctcaa tgaggttgcc aagaatttaa atgaatctct catcgatctc     3600
caagaacttg gaaagtatga gcaggggtca ggctacatcc ccgaggcccc cagggacggc     3660
caggcctacg tgaggaagga cggcgagtgg gtgctgctga gcaccttcct gggcaggagc     3720
```

-continued

```
ctggaggtgc tgttccaggg ccccggccat catcatcatc atcatcatca tagcgcttgg     3780
agccacccgc agttcgaaaa aggtggaggt tctggcggcg gtggatcggg aggttcagcg     3840
tggagccacc cgcagttcga gaaatag                                         3867

<210> SEQ ID NO 49
<211> LENGTH: 3714
<212> TYPE: DNA
<213> ORGANISM: artificial sequence
<220> FEATURE:
<223> OTHER INFORMATION: spike protein

<400> SEQUENCE: 49
atgtttgttt ttcttgtttt attgccacta gtctctagtc agtgtgttaa tcttacaacc       60
agaactcaat taccccctgc atacactaat tctttcacac gtggtgttta ttaccctgac      120
aaagttttca gatcctcagt tttacattca actcaggact tgttcttacc tttcttttcc      180
aatgttactt ggttccatgc tatacatgtc tctgggacca atggtactaa gaggtttgat      240
aaccctgtcc taccatttaa tgatggtgtt tattttgctt ccactgagaa gtctaacata      300
ataagaggct ggattttttgg tactacttta gattcgaaga cccagtccct acttattgtt      360
aataacgcta ctaatgttgt tattaaagtc tgtgaatttc aattttgtaa tgatccattt      420
ttgggtgttt attaccacaa aaacaacaaa agttggatgg aaagtgagtt cagagtttat      480
tctagtgcga ataattgcac ttttgaatat gtctctcagc ctttcttat ggaccttgaa       540 ggaaaacagg gtaatttcaa aaatcttagg gaatttgtgt ttaagaatat tgatggttat      600
tttaaaatat attctaagca cacgcctatt aatttagtgc gtgatctccc tcagggtttt      660
tcggctttag aaccattggt agatttgcca ataggtatta acatcactag gtttcaaact      720
ttacttgctt tacatagaag ttatttgact cctggtgatt cttcttcagg ttggacagct      780
ggtgctgcag cttattatgt gggttatctt caacctagga ctttttctatt aaaatataat     840 gaaaatggaa ccattacaga tgctgtagac tgtgcacttg accctctctc agaaacaaag       900
tgtacgttga atccttcac tgtagaaaaa ggaatctatc aaacttctaa ctttagagtc        960
caaccaacag aatctattgt tagatttcct aatattacaa acttgtgccc ttttggtgaa      1020
gtttttaacg ccaccagatt tgcatctgtt tatgcttgga acaggaagag aatcagcaac      1080
tgtgttgctg attattctgt cctatataat tccgcatcat tttccacttt taagtgttat      1140
ggagtgtctc ctactaaatt aaatgatctc tgctttacta atgtctatgc agattcattt      1200
gtaattagag gtgatgaagt cagacaaatc gctccagggc aaactggaaa gattgctgat      1260
tataattata attaccagga tgattttaca ggctgcgtta tagcttggaa ttctaacaat      1320
cttgattcta aggttggtgg taattataat tacctgtata gattgtttag gaagtctaat      1380
ctcaaacctt ttgagagaga tatttcaact gaaatctatc aggccggtag cacaccttgt      1440
aatggtgttg aaggttttaa ttgttacttt cctttacaat catatggttt ccaacccact      1500
aatggtgttg gttaccaacc atacagagta gtagtacttt cttttgaact ctacatgca      1560 ccagcaactg tttgtggacc taaaaagtct actaatttgg ttaaaaacaa atgtgtcaat      1620
ttcaacttca atggtttaac aggcacaggt gttcttactg agtctaacaa aaagtttctg      1680
cctttccaac aatttggcag agacattgct gacactactg atgctgtccg tgatccacag      1740
acacttgaga ttcttgacat tacaccatgt tcttttggtg gtgtcagtgt tataacacca      1800
ggaacaaata cttctaacca ggttgctgtt ctttatcagg gtgttaactg cacagaagtc      1860
```

```
cctgttgcta ttcatgcaga tcaacttact cctacttggc gtgtttattc tacaggttct      1920 aatgttttc aaacacgtgc aggctgttta atagggggtg aacatgtcaa caactcatat       1980
gagtgtgaca tacccattgg tgcaggtata tgcgctagtt atcagactca gactaattct     2040
cctgggtcgg catctagtgt agctagtcaa tccatcattg cctacactat gtcacttggt     2100
gcagaaaatt cagttgctta ctctaataac tctattgcca tacccacaaa ttttactatt     2160
agtgttacca cagaaattct accagtgtct atgaccaaga catcagtaga ttgtacaatg     2220
tacatttgtg gtgattcaac tgaatgcagc aatcttttgt tgcaatatgg cagtttttgt     2280
acacaattaa accgtgcttt aactggaata gctgttgaac aagacaaaaa cacccaagaa     2340 gttttttgcac aagtcaaaca aatttacaaa acaccaccaa ttaaagattt tggtggtttt    2400 aattttttcac aaatattacc agatccatca aaaccaagca agaggtcacc tattgaagat    2460
ctacttttca acaaagtgac acttgcagat gctggcttca tcaaacaata tggtgattgc     2520
cttggtgata ttgctgctag agacctcatt tgtgcacaaa agtttaacgg ccttactgtt     2580
ttgccaccat tgctcacaga tgaaatgatt gctcaataca cttctgcact gttagcgggt    2640
acaatcactt ctggttggac ctttggtgca ggtcctgcat tacaaatacc atttcctatg    2700
caaatggctt ataggtttaa tggtattgga gttacacaga atgttctcta tgagaaccaa     2760
aaattgattg ccaaccaatt taatagtgct attggcaaaa ttcaagactc actttcttcc    2820
acaccaagtg cacttggaaa acttcaagat gtggtcaacc aaaatgcaca agctttaaac   2880
acgcttgtta aacaacttag ctccaatttt ggtgcaattt caagtgtttt aaatgatatc     2940
ctttcacgtc ttgacccacc tgaggctgaa gtgcaaattg ataggttgat cacaggcaga    3000
cttcaaagtt tgcagacata tgtgactcaa caattaatta gagctgcaga aatcagagct    3060
tctgctaatc ttgctgctac taaaatgtca gagtgtgtac ttggacaatc aaaaagagtt    3120 gattttgtg gaaagggcta tcatcttatg tccttccctc agtcagcacc tcatggtgta      3180
gtcttcttgc atgtgactta tgtccctgca caagaaaaga acttcacaac tgctcctgcc     3240
atttgtcatg atggaaaagc acactttcct cgtgaaggtg tctttgtttc aaatggcaca     3300
cactggtttg taacacaaag gaatttttat gaaccacaaa tcattactac agacaacaca    3360
tttgtgtctg gtaactgtga tgttgtaata ggaattgtca acaacacagt ttatgatcct     3420
ttgcaacctg aattagactc attcaaggag gagttagata atatttttaa gaatcataca     3480
tcaccagatg ttgatttagg tgacatctct ggcattaatg cttcagttgt aaacattcaa     3540
aaagaaattg accgcctcaa tgaggttgcc aagaatttaa atgaatctct catcgatctc     3600
caagaacttg gaaagtatga gcaggggtca ggctacatcc ccgaggcccc cagggacggc     3660
caggcctacg tgaggaagga cggcgagtgg gtgctgctga gcaccttcct gtag           3714
```

<210> SEQ ID NO 50
<211> LENGTH: 3852
<212> TYPE: DNA
<213> ORGANISM: artificial sequence
<220> FEATURE:
<223> OTHER INFORMATION: spike protein with mCRAMP

<400> SEQUENCE: 50

```
atgtttgttt ttcttgtttt attgccacta gtctctagtc agtgtgttaa tcttacaacc         60
agaactcaat taccccctgc atacactaat tctttcacac gtggtgttta ttaccctgac         120
aaagttttca gatcctcagt tttacattca actcaggact tgttcttacc tttcttttcc         180
aatgttactt ggttccatgc tatacatgtc tctgggacca atggtactaa gaggtttgat        240
```

```
aaccctgtcc taccatttaa tgatggtgtt tattttgctt ccactgagaa gtctaacata    300
ataagaggct ggatttttgg tactacttta gattcgaaga cccagtccct acttattgtt    360
aataacgcta ctaatgttgt tattaaagtc tgtgaatttc aattttgtaa tgatccattt    420
ttgggtgttt attaccacaa aaacaacaaa agttggatgg aaagtgagtt cagagtttat    480
tctagtgcga ataattgcac ttttgaatat gtctctcagc cttttcttat ggaccttgaa    540
ggaaaacagg gtaatttcaa aaatcttagg gaatttgtgt ttaagaatat tgatggttat    600
tttaaaatat attctaagca cacgcctatt aatttagtgc gtgatctccc tcagggtttt    660
tcggctttag aaccattggt agatttgcca ataggtatta acatcactag gtttcaaact    720
ttacttgctt tacatagaag ttatttgact cctggtgatt cttcttcagg ttggacagct    780
ggtgctgcag cttattatgt gggttatctt caacctagga cttttctatt aaaatataat    840
gaaaatggaa ccattacaga tgctgtagac tgtgcacttg accctctctc agaaacaaag    900
tgtacgttga aatccttcac tgtagaaaaa ggaatctatc aaacttctaa ctttagagtc    960
caaccaacag aatctattgt tagatttcct aatattacaa acttgtgccc ttttggtgaa   1020 gttttttaacg ccaccagatt tgcatctgtt tatgcttgga acaggaagag aatcagcaac   1080
tgtgttgctg attattctgt cctatataat tccgcatcat tttccacttt taagtgttat   1140
ggagtgtctc ctactaaatt aaatgatctc tgctttacta atgtctatgc agattcattt   1200
gtaattagag gtgatgaagt cagacaaatc gctccagggc aaactggaaa gattgctgat   1260
tataattata aattaccaga tgattttaca ggctgcgtta tagcttggaa ttctaacaat   1320
cttgattcta aggttggtgg taattataat tacctgtata gattgtttag gaagtctaat   1380
ctcaaacctt ttgagagaga tatttcaact gaaatctatc aggccggtag cacaccttgt   1440
aatggtgttg aaggttttaa ttgttacttt cctttacaat catatggttt ccaacccact   1500
aatggtgttg gttaccaacc atacagagta gtagtacttt cttttgaact tctacatgca   1560
ccagcaactg tttgtggacc taaaaagtct actaatttgg ttaaaaacaa atgtgtcaat   1620
ttcaacttca atggtttaac aggcacaggt gttcttactg agtctaacaa aaagtttctg   1680
cctttccaac aatttggcag agacattgct gacactactg atgctgtccg tgatccacag   1740
acacttgaga ttcttgacat tacaccatgt tcttttggtg gtgtcagtgt tataacacca   1800
ggaacaaata cttctaacca ggttgctgtt ctttatcagg gtgttaactg cacagaagtc   1860
cctgttgcta ttcatgcaga tcaacttact cctacttggc gtgtttattc tacaggttct   1920
aatgtttttc aaacacgtgc aggctgttta ataggggctg aacatgtcaa caactcatat   1980
gagtgtgaca tacccattgg tgcaggtata tgcgctagtt atcagactca gactaattct   2040
cctgggtcgg catctagtgt agctagtcaa tccatcattg cctacactat gtcacttggt   2100
gcagaaaatt cagttgctta ctctaataac tctattgcca tacccacaaa ttttactatt   2160
agtgttacca cagaaattct accagtgtct atgaccaaga catcagtaga ttgtacaatg   2220
tacatttgtg gtgattcaac tgaatgcagc aatcttttgt tgcaatatgg cagttttttgt   2280 acacaattaa accgtgcttt aactggaata gctgttgaac aagacaaaaa cacccaagaa   2340
gtttttgcac aagtcaaaca aatttacaaa acaccaccaa ttaaagattt tggtggtttt   2400
aatttttcac aaatattacc agatccatca aaaccaagca agaggtcacc tattgaagat   2460
ctacttttca caaagtgac acttgcagat gctggcttca tcaaacaata tggtgattgc   2520
cttggtgata ttgctgctag agacctcatt tgtgcacaaa agtttaacgg ccttactgtt   2580
```

```
ttgccacctt tgctcacaga tgaaatgatt gctcaataca cttctgcact gttagcgggt   2640
acaatcactt ctggttggac ctttggtgca ggtcctgcat tacaaatacc atttcctatg   2700
caaatggctt ataggtttaa tggtattgga gttacacaga atgttctcta tgagaaccaa   2760
aaattgattg ccaaccaatt taatagtgct attggcaaaa ttcaagactc actttcttcc   2820
acaccaagtg cacttggaaa acttcaagat gtggtcaacc aaaatgcaca agctttaaac   2880
acgcttgtta aacaacttag ctccaatttt ggtgcaattt caagtgtttt aaatgatatc   2940 cttcacgtc ttgacccacc tgaggctgaa gtgcaaattg ataggttgat cacaggcaga   3000
cttcaaagtt tgcagacata tgtgactcaa caattaatta gagctgcaga aatcagagct   3060
tctgctaatc ttgctgctac taaaatgtca gagtgtgtac ttggacaatc aaaaagagtt   3120
gatttttgtg gaaagggcta tcatcttatg tccttccctc agtcagcacc tcatggtgta   3180
gtcttcttgc atgtgactta tgtccctgca caagaaaaga acttcacaac tgctcctgcc   3240
atttgtcatg atggaaaagc acactttcct cgtgaaggtg tctttgtttc aaatggcaca   3300
cactggtttg taacacaaag gaatttttat gaaccacaaa tcattactac agacaacaca   3360
tttgtgtctg gtaactgtga tgttgtaata ggaattgtca acaacacagt ttatgatcct   3420
ttgcaacctg aattagactc attcaaggag gagttagata aatattttaa gaatcataca   3480
tcaccagatg ttgatttagg tgacatctct ggcattaatg cttcagttgt aaacattcaa   3540
aaagaaattg accgcctcaa tgaggttgcc aagaatttaa atgaatctct catcgatctc   3600
caagaacttg gaaagtatga gcaggggtca ggctacatcc ccgaggcccc cagggacggc   3660
caggcctacg tgaggaagga cggcgagtgg gtgctgctga gcaccttcct gggtggaggt   3720
tctggcggtg gatcgggtgg aggttctgga cttctccgca aaggtgggga gaagattggt   3780
gaaaagctta agaaaattgg ccagaaaatt aagaattttt ttcagaaact tgtacctcag   3840
ccagagcagt ag                                                       3852
```